United States Patent
Aesaert et al.

(10) Patent No.: US 12,077,788 B2
(45) Date of Patent: Sep. 3, 2024

(54) PRODUCTION OF A MIXTURE OF NEUTRAL NON-FUCOSYLATED OLIGOSACCHARIDES BY A CELL

(71) Applicant: INBIOSE N.V., Zwijnaarde (BE)

(72) Inventors: Sofie Aesaert, Zwijnaarde (BE); Joeri Beauprez, Zwijnaarde (BE); Pieter Coussement, Zwijnaarde (BE); Thomas Decoene, Zwijnaarde (BE); Nausicaä Lannoo, Zwijnaarde (BE); Gert Peters, Zwijnaarde (BE); Kristof Vandewalle, Zwijnaarde (BE); Annelies Vercauteren, Zwijnaarde (BE)

(73) Assignee: INBIOSE N.V., Zwijnaarde (BE)

( * ) Notice: Subject to any disclaimer, the term of this patent is extended or adjusted under 35 U.S.C. 154(b) by 0 days.

(21) Appl. No.: 18/040,629

(22) PCT Filed: Aug. 10, 2021

(86) PCT No.: PCT/EP2021/072265
§ 371 (c)(1),
(2) Date: Feb. 3, 2023

(87) PCT Pub. No.: WO2022/034071
PCT Pub. Date: Feb. 17, 2022

(65) Prior Publication Data
US 2023/0265399 A1 Aug. 24, 2023

(30) Foreign Application Priority Data

| Aug. 10, 2020 | (EP) | 20190198 |
| Aug. 10, 2020 | (EP) | 20190200 |
| Aug. 10, 2020 | (EP) | 20190201 |
| Aug. 10, 2020 | (EP) | 20190202 |
| Aug. 10, 2020 | (EP) | 20190203 |
| Aug. 10, 2020 | (EP) | 20190204 |
| Aug. 10, 2020 | (EP) | 20190205 |
| Aug. 10, 2020 | (EP) | 20190206 |
| Aug. 10, 2020 | (EP) | 20190207 |
| Aug. 10, 2020 | (EP) | 20190208 |
| Apr. 16, 2021 | (EP) | 21168997 |
| Jul. 16, 2021 | (EP) | 21186202 |
| Jul. 16, 2021 | (EP) | 21186203 |

(51) Int. Cl.
| C12N 9/10 | (2006.01) |
| C12N 1/00 | (2006.01) |
| C12N 1/20 | (2006.01) |
| C12N 5/00 | (2006.01) |
| C12N 15/52 | (2006.01) |
| C12N 15/70 | (2006.01) |
| C12P 7/58 | (2006.01) |
| C12P 19/12 | (2006.01) |
| C12P 19/18 | (2006.01) |
| C12P 19/26 | (2006.01) |

(52) U.S. Cl.
CPC ............ *C12N 9/1048* (2013.01); *C12N 1/00* (2013.01); *C12N 1/20* (2013.01); *C12N 5/00* (2013.01); *C12N 9/1029* (2013.01); *C12N 9/1051* (2013.01); *C12N 9/1096* (2013.01); *C12N 15/52* (2013.01); *C12N 15/70* (2013.01); *C12P 7/58* (2013.01); *C12P 19/12* (2013.01); *C12P 19/18* (2013.01); *C12P 19/26* (2013.01); *C12Y 203/01004* (2013.01); *C12Y 204/00* (2013.01); *C12Y 206/01016* (2013.01); *C12N 2500/34* (2013.01)

(58) Field of Classification Search
CPC .......... C12N 9/1048; C12N 1/00; C12N 1/20; C12N 5/00; C12N 9/1029; C12N 9/1096; C12N 15/52; C12N 15/70; C12N 2500/34; C12P 7/58; C12P 19/12; C12P 19/18; C12P 19/26; C12P 19/00; C12Y 203/01004; C12Y 204/00; C12Y 206/01016; C12Y 204/01
See application file for complete search history.

(56) References Cited

U.S. PATENT DOCUMENTS

| 11,293,042 B2 * | 4/2022 | Pedersen ........ C12Y 204/01086 |
| 2009/0082307 A1 | 3/2009 | Samain et al. |
| 2011/0014661 A1 | 1/2011 | Samain |
| 2017/0306373 A1 | 10/2017 | Heidtman et al. |

FOREIGN PATENT DOCUMENTS

| EP | 2722394 A1 | 4/2014 |
| EP | 2971030 B1 | 10/2018 |
| EP | 3177325 B1 | 4/2020 |

(Continued)

OTHER PUBLICATIONS

Spahn et al., A Markov chain model for N-linked protein glycosylation—towards a low-parameter tool for model-driven glycoengineering. Metabol. Eng., 2016, vol. 33: 52-56 (Year: 2016).*
Benedetti et al., Network inference from glycoproteomics data reveals new reactions in the IgG glycosylation pathway. Nat. Commun., 2017, vol. 8:1483, pp. 1-15. (Year: 2017).*
Devos et al., Practical limits of function prediction. Proteins: Structure, Function, and Genetics. 2000, vol. 41: 98-107. 2000 (Year: 2000).*

(Continued)

*Primary Examiner* — Ganapathirama Raghu
(74) *Attorney, Agent, or Firm* — TraskBritt

(57) ABSTRACT

The disclosure is in the technical field of synthetic biology and metabolic engineering. More particularly, the disclosure is in the technical field of cultivation or fermentation of metabolically engineered cells. The disclosure describes a cell metabolically engineered for production of a mixture of at least four different neutral non-fucosylated oligosaccharides. Furthermore, the disclosure provides a method for the production of a mixture of at least four different neutral non-fucosylated oligosaccharides by a cell as well as the purification of at least one of the oligosaccharides from the cultivation.

27 Claims, No Drawings

(56) References Cited

FOREIGN PATENT DOCUMENTS

| WO | 00/29603 A2 | 5/2000 |
| WO | 2006/034225 A2 | 3/2006 |
| WO | 2007/101862 A1 | 9/2007 |
| WO | 2011/035884 A1 | 3/2011 |
| WO | 2012/007481 A2 | 1/2012 |
| WO | 2012/156897 A1 | 11/2012 |
| WO | 2014/152137 A2 | 9/2014 |
| WO | 2014/153253 A1 | 9/2014 |
| WO | 2015/175801 A1 | 11/2015 |
| WO | 2016/091268 A2 | 6/2016 |
| WO | 2017/101958 A1 | 6/2017 |
| WO | 2019/020707 A1 | 1/2019 |

OTHER PUBLICATIONS

Pettit et al., Identification, Characterization, and Utilization of Glycosyltransferases. PhD., Thesis, 2011, pp. 1-288, The Ohio State University (Year: 2011).*

Whisstock et al., Prediction of protein function from protein sequence. Q. Rev. Biophysics., 2003, vol. 36 (3): 307-340. (Year: 2003).*

Bode et al., Making Human Milk Oligosaccharides Available for Research and Application—Approaches, Challenges and Future Opportunities", In: 11 Prebiotics and Probiotics in Human Milk", (Jan. 1, 2017), pp. 251-293.

European Communication pursuant to Article 94(3) EPC for European Application No. 20190203.8, dated Feb. 10, 2022, 5 pages.

European Communication pursuant to Article 94(3) EPC for European Application No. 20190205.3, dated Dec. 22, 2022, 5 pages.

European Extended Search Report and Opinion for European Application No. 20190203.8, dated Feb. 9, 2021, 7 pages.

European Extended Search Report and Opinion for European Application No. 20190205.3, dated Feb. 10, 2021, 8 pages.

International Search Report for International Application No. PCT/EP2021/072265, dated Dec. 22, 2021, 4 pages.

International Written Opinion for International Application No. PCT/EP2021/072265, dated Dec. 22, 2021, 7 pages.

Priem, et al., "A New Fermentation Process Allows Large-Scale Production of Human Milk Oligosaccharides by Metabolically Engineered Bacteria," Glycobiology, vol. 12, No. 4, pp. 235-240 (Aug. 2001).

Zhang et al., Microbial production of sialic acid and sialylated human milk oligosaccharides: Advances and perspectives, Biotechnology Advances, vol. 37, No. 5 (Sep. 1, 2019), pp. 787-800.

Faijes et al. "Enzymatic and cell factory approaches to the production of human milk oligosaccharides", Biotechnology Advances, vol. 37, No. 5, Sep. 1, 2019, pp. 667-697, XP085733160.

Han et al. "Biotechnological production of human milk oligosaccharides", Biotechnology Advances, vol. 30, No. 6, Nov. 1, 2012, pp. 1268-1278, XP055074947.

Samain et al. "Production of O-acetylated and sulfated chitooligosaccharides by recombinant *Escherichia coli* strains harboring different combinations of nod genes" Journal of Biotechnology, vol. 72, Issues 1-2 (Jun. 1999) pp. 33-47.

Baumgartner et al. "Synthesis of fucosylated lacto-N-tetraose using whole-cell biotransformation" Bioorganic & Midicianl chemistry 23, 6799-6806 (published Oct. 9, 2015).

Baumgartner: Biotechnologische Darstellung und strukturelle Charakterisierung fucosylierter Oligosaccharide. PhD thesis, Institut fur Mikrobiologie der Universitat Stuttgart—published: 2016.

Bode "The functional biology of human milk oligosaccharides" Early Hum. Dev. vol. 91, Issue 11 (Nov. 2015) pp. 619-622.

Bosmann "Bacterial Glycoproteins: Identification and Properties of GL Ycoprotein Glycosyltransferases in *Escherichia coli*" Biochim. Biophys. Acta, 252 (May 27, 1971) 369-387.

Cote et al. "The Glycosyltransferases of LPS Core: A Review of Four Heptosyltransferase Enzymes in Context" Int. J. Mal. Sci., 18, 2256 (Published: Oct. 27, 2017) 17 Pages.

Coutinho et al. "An Evolving Hierarchical Family Classification for Glycosyltransferases" J. Mol. Biol, vol. 328, Issue 2 (Apr. 25, 2003) pp. 307-317 (Abstact Only).

Donovan et al. "Review: Optimizing inducer and culture conditions for expression of foreign proteins under the control of the lac promoter" Journal of Industrial Microbiology (1996) 16, 145-154 (accepted Dec. 6, 1995).

*Escherichia coli* and *Salmonella*: Cellular and Molecular Biology, published in 1996.

*Escherichia coli* strain JM109 chromosome, complete genome. National Library of Medicine, National Center for Biotechnology Information.

Essentials of GL Ycobiology; edited by A. Varki, R. Cummings, J. Esko, H. Freeze, G. Hart and J. Marth, 1999, Cold Spring Harbor Laboratory Press, New York; pp. 5-10, 32-33, 69-70, 85-100, and 253-257.

FDA—GRAS Notice GRN No. 659 with supplement—Lacto-Nneotetraose—published: 2016.

FDA—GRAS Notice GRN No. 833—Lacto-N-neotetraose—published: 2019.

Forrest et al "The structural basis of secondary active transport mechanisms" Biochimica et Biophysica Acta 1807 (Feb. 2011) 167-188.

Genome Annotation, Genes annotated on *Escherichia coli* DH 1, National Library of Medicine, National Center for Biotechnology Information.

Glick et al. "Metabolic Load and Heterologous Gene Expression" Biotechnology Advances, vol. 13, No. 2, pp. 247-261, Published in 1995.

GRAS notification 923, published Feb. 2, 2021.

Jeffries "Glycosylation as a strategy to improve antibody-based Therapeutics" Nature Reviews Drug Discovery, vol. 8 (Mar. 2009) 226-234.

Kanda et al. "Comparison of Cell Lines for Stable Production of Fucose-Negative Antibodies With Enhanced ADCC" Biotechnology and Bioengineering, vol. 94(4), Accepted Jan. 9, 2006: 680-688.

Leipold et al. "Glycosyltransferases Involved in Biosynthesis of the Outer Core Region of *Escherichia coli* Lipopolysaccharides Exhibit Broader Substrate Specificities Than Is Predicted from Lipopolysaccharide Structures" The Journal of Biological Chemistry, vol. 282, No. 37, pp. 26786-26792, (Sep. 14, 2007).

Ludger N-glycan nomenclature; 2019.

Malphettes et al. "Highly Efficient Deletion of FUTB in CHO Cell lines Using Zinc-Finger Nucleases Yields Cells That Produce Completely Nonfucosylated Antibodies" Biotechnology and Bioengineering, vol. 106(5), (Aug. 1, 2010) 774-738.

Moraes et al. "Membrane transport metabolons" Biochim. Biophys. Acta, vol. 1818, Issue 11, Nov. 2012, pp. 2687-2706.

Notice of Opposition Proceedings filed by Opponent Chr. Hansen HMO GmbH for European Patent No. EP3954778, dated Jun. 25, 2024, 34 pages.

Notice of Opposition Proceedings filed by Opponent Glycom A/S for European Patent No. EP3954778, dated Jul. 3, 2024, 49 pages.

Notice of Opposition Proceedings filed by Opponent Oetke Cornelia for European Patent No. EP3954778, dated Jul. 4, 2024, 24 pages.

Peng et al. "Chemical Structure and Composition of Major Glycans Covalently Linked to Therapeutic Monoclonal Antibodies by Middle-Down Nuclear Magnetic Resonance" Anal Chem, vol. 90(18), Sep. 18, 2018, 11016-11024.

Reily et al "Glycosylation in health and disease" Reily et al., Nat. Rev. Nephrol. vol. 15 (Jun. 2019) pp. 346-366.

Saier et al. "The Transporter Classification Database(TCDB): recent advances" Nucleic Acids Research, 2016, vol. 44, Database issue (Jan. 4, 2016) D372-D379.

Ten Bruggencate et al. "Functional role and mechanisms of sialyllactose and other sialylated milk oligosaccharides" Nutrition Reviews, vol. 72(6):377-389—published: 2014.

Urashima et al. "Human Milk Oligosaccharides as Essential Tools for Basic and Application Studies on Galectins" Trends in Glycoscience and Glycotechnology, vol. 30, No. 172, (Jan.-May 2018) pp. SE51-SE65.

Varki "Biological roles of glycans" Glycobiology, vol. 27, No. 1 (Accepted Aug. 16, 2016) pp. 3-49.

Walsh et al. "From lab bench to formulated ingredient: Characterization, production, and commercialization of human milk oligosaccharides" Journal of Functional Foods, vol. 72, 2020, 104052—published: Jun. 16, 2020.

Wang et al. "Antibody glycoengineering strategies in mammalian cells" Biotechnology and Bioengineering, vol. 115 (Accepted Feb. 13, 2018) 1378-1393.

Yamane-Ohnuki et al. "Establishment of FUT8 Knockout Chinese Hamster Ovary Cells: An Ideal Host Cell Line for Producing Completely Defucosylated Antibodies With Enhanced Antibody-Dependent Cellular Cytotoxicity" Biotechnology and Bioengineering, vol. 87(5), Accepted Mar. 29, 2004: 614-622.

Yavuz et al. "Glycomimicry: display of fucosylation on the Lipo-oligosaccharide of recombinant *Escherichia coli* K12" Glycoconj J., 28:39-47, (Published online Feb. 1, 2011).

\* cited by examiner

PRODUCTION OF A MIXTURE OF NEUTRAL NON-FUCOSYLATED OLIGOSACCHARIDES BY A CELL

CROSS-REFERENCE TO RELATED APPLICATIONS

This application is a national phase entry under 35 U.S.C. § 371 of International Patent Application PCT/EP2021/072265, filed Aug. 10, 2021, designating the United States of America and published as International Patent Publication WO 2022/034071 A1 on Feb. 17, 2022, which claims the benefit under Article 8 of the Patent Cooperation Treaty to European Patent Application Serial Nos. EP 21186203.2, filed Jul. 16, 2021; EP 21186202.4, filed Jul. 16, 2021; EP 21168997.1, filed Apr. 16, 2021; EP 20190208.7, filed Aug. 10, 2020; EP 20190207.9, filed Aug. 10, 2020; EP 20190206.1, filed Aug. 10, 2020; EP 20190205.3, filed Aug. 10, 2020; EP 20190204.6, filed Aug. 10, 2020; EP 20190202.0, filed Aug. 10, 2020; EP 20190201.2, filed Aug. 10, 2020; EP 20190200.4, filed Aug. 10, 2020; EP 20190198.0, filed Aug. 10, 2020; and EP 20190203.8, filed Aug. 10, 2020.

TECHNICAL FIELD

The disclosure is in the technical field of synthetic biology and metabolic engineering. More particularly, the disclosure is in the technical field of cultivation or fermentation of metabolically engineered cells. The disclosure describes a cell metabolically engineered for production of a mixture of at least four different neutral non-fucosylated oligosaccharides. Furthermore, the disclosure provides a method for the production of a mixture of at least four different neutral non-fucosylated oligosaccharides by a cell as well as the purification of at least one of the oligosaccharides from the cultivation.

BACKGROUND

Oligosaccharides, often present as glyco-conjugated forms to proteins and lipids, are involved in many vital phenomena such as differentiation, development and biological recognition processes related to the development and progress of fertilization, embryogenesis, inflammation, metastasis and host pathogen adhesion. Oligosaccharides can also be present as unconjugated glycans in body fluids and human milk wherein they also modulate important developmental and immunological processes (Bode, Early Hum. Dev. 1-4 (2015); Reily et al., Nat. Rev. Nephrol. 15, 346-366 (2019); Varki, Glycobiology 27, 3-49 (2017)). There is large scientific and commercial interest in oligosaccharide mixtures due to the wide functional spectrum of oligosaccharides. Yet, the availability of oligosaccharide mixtures is limited as production relies on chemical or chemo-enzymatic synthesis or on purification from natural sources such as, e.g., animal milk. Chemical synthesis methods are laborious and time-consuming and because of the large number of steps involved they are difficult to scale-up. Enzymatic approaches using glycosyltransferases offer many advantages above chemical synthesis. Glycosyltransferases catalyze the transfer of a sugar moiety from an activated nucleotide-sugar donor onto saccharide or non-saccharide acceptors (Coutinho et al., J. Mol. Biol. 328 (2003) 307-317). These glycosyltransferases are the source for biotechnologists to synthesize oligosaccharides and are used both in (chemo)enzymatic approaches as well as in cell-based production systems. However, stereospecificity and regioselectivity of glycosyltransferases are still a formidable challenge. In addition, chemo-enzymatic approaches need to regenerate in situ nucleotide-sugar donors. Cellular production of oligosaccharides needs tight control of spatiotemporal availability of adequate levels of nucleotide-sugar donors in proximity of complementary glycosyltransferases. Due to these difficulties, current methods often result in the synthesis of a single oligosaccharide instead of an oligosaccharide mixture.

BRIEF SUMMARY

It is an object of the disclosure to provide for tools and methods by means of which an oligosaccharide mixture comprising at least four different neutral non-fucosylated oligosaccharides can be produced by a cell, preferably a single cell, in an efficient, time and cost-effective way and if needed, continuous process.

According to the disclosure, this and other objects are achieved by providing a cell and a method for the production of an oligosaccharide mixture comprising at least four different neutral non-fucosylated oligosaccharides wherein the cell is genetically modified for the production of the oligosaccharides.

Surprisingly, it has now been found that it is possible to produce oligosaccharide mixtures comprising at least four different neutral non-fucosylated oligosaccharides by a single cell. The disclosure provides a metabolically engineered cell and a method for the production of an oligosaccharide mixture comprising at least four different neutral non-fucosylated oligosaccharides. The method comprises the steps of providing a cell which expresses at least two glycosyltransferases and is capable to synthesize (a) nucleotide-sugar(s) that is/are donor(s) for the glycosyltransferases cultivating the cell under conditions permissive for producing the oligosaccharide mixture. The disclosure also provides methods to separate at least one, preferably all, of the oligosaccharides from the neutral non-fucosylated oligosaccharide mixture. Furthermore, the disclosure provides a cell metabolically engineered for production of an oligosaccharide mixture comprising at least four different neutral non-fucosylated oligosaccharides.

Definitions

The words used in this specification to describe the disclosure and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The various embodiments and aspects of embodiments of the disclosure disclosed herein are to be understood not only in the order and context specifically described in this specification, but to include any order and any combination thereof. Whenever the context requires, all words used in the singular number shall be deemed to include the plural and vice versa. Unless defined otherwise, all technical and scientific terms used herein generally have the same meaning as commonly understood by one of ordinary skill in the art to which this disclosure belongs. Generally, the nomenclature used herein and the laboratory procedures in cell culture, molecular genetics, organic chemistry and nucleic acid chemistry and hybridization described herein are those well-known and commonly employed in the art. Standard techniques are used for nucleic acid and peptide synthesis. Generally, purification steps are performed according to the manufacturer's specifications.

In the specification, there have been disclosed embodiments of the disclosure, and although specific terms are employed, the terms are used in a descriptive sense only and not for purposes of limitation, the scope of the disclosure being set forth in the following claims. It must be understood that the illustrated embodiments have been set forth only for the purposes of example and that it should not be taken as limiting the disclosure. It will be apparent to those skilled in the art that alterations, other embodiments, improvements, details and uses can be made consistent with the letter and spirit of the disclosure herein and within the scope of this disclosure, which is limited only by the claims, construed in accordance with the patent law, including the doctrine of equivalents. In the claims which follow, reference characters used to designate claim steps are provided for convenience of description only, and are not intended to imply any particular order for performing the steps.

In this document and in its claims, the verb "to comprise" and its conjugations is used in its non-limiting sense to mean that items following the word are included, but items not specifically mentioned are not excluded. Throughout the application, the verb "to comprise" may be replaced by "to consist" or "to consist essentially of" and vice versa. In addition the verb "to consist" may be replaced by "to consist essentially of" meaning that a composition as defined herein may comprise additional component(s) than the ones specifically identified, the additional component(s) not altering the unique characteristic of the disclosure. In addition, reference to an element by the indefinite article "a" or "an" does not exclude the possibility that more than one of the elements is present, unless the context clearly requires that there be one and only one of the elements. The indefinite article "a" or "an" thus usually means "at least one." Throughout the application, unless explicitly stated otherwise, the articles "a" and "an" are preferably replaced by "at least two," more preferably by "at least three," even more preferably by "at least four," even more preferably by "at least five," even more preferably by "at least six," most preferably by "at least seven."

Each embodiment as identified herein may be combined together unless otherwise indicated. All publications, patents, and patent applications mentioned in this specification are herein incorporated by reference to the same extent as if each individual publication, patent, or patent application was specifically and individually indicated to be incorporated by reference. The full content of the priority applications, including EP20190198, EP20190200, EP20190203, EP20190204 and EP20190205, are also incorporated by reference to the same extent as if the priority applications were specifically and individually indicated to be incorporated by reference.

According to the disclosure, the term "polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" according to the disclosure. Moreover, DNAs or RNAs comprising unusual bases, such as inosine, or modified bases, such as tritylated bases, are to be understood to be covered by the term "polynucleotides." It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. The term "polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to the skilled person. The same type of modification may be present in the same or varying degree at several sites in a given polypeptide. Furthermore, a given polypeptide may contain many types of modifications. Modifications can occur anywhere in a polypeptide, including the peptide backbone, the amino acid sidechains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, lipid attachment, sulfation, gamma-carboxylation of glutamic acid residues, hydroxylation and ADP-ribosylation, selenoylation, transfer-RNA mediated addition of amino acids to proteins, such as arginylation, and ubiquitination. Polypeptides may be branched or cyclic, with or without branching. Cyclic, branched and branched circular polypeptides may result from post-translational natural processes and may be made by entirely synthetic methods, as well.

The term "polynucleotide encoding a polypeptide" as used herein encompasses polynucleotides that include a sequence encoding a polypeptide of the disclosure. The term also encompasses polynucleotides that include a single continuous region or discontinuous regions encoding the polypeptide (for example, interrupted by integrated phage or an insertion sequence or editing) together with additional regions that also may contain coding and/or non-coding sequences.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated," as the term is employed herein. Similarly, a "synthetic" sequence, as the term is used herein, means any sequence that has been generated synthetically and not directly isolated from a natural source. "Synthesized," as the term is used herein, means any synthetically generated sequence and not directly isolated from a natural source.

The terms "recombinant" or "transgenic" or "metabolically engineered" or "genetically modified," as used herein with reference to a cell or host cell are used interchangeably and indicates that the cell replicates a heterologous nucleic acid, or expresses a peptide or protein encoded by a heterologous nucleic acid (i.e., a sequence "foreign to the cell" or a sequence "foreign to the location or environment in the cell"). Such cells are described to be transformed with at least one heterologous or exogenous gene, or are described to be transformed by the introduction of at least one heterologous or exogenous gene. Metabolically engineered or recombinant or transgenic cells can contain genes that are not found within the native (non-recombinant) form of the cell. Recombinant cells can also contain genes found in the native form of the cell wherein the genes are modified and re-introduced into the cell by artificial means. The terms also encompass cells that contain a nucleic acid endogenous to the cell that has been modified or its expression or activity has been modified without removing the nucleic acid from the cell; such modifications include those obtained by gene replacement, replacement of a promoter; site-specific mutation; and related techniques. Accordingly, a "recombinant polypeptide" is one which has been produced by a recombinant cell. A "heterologous sequence" or a "heterologous nucleic acid," as used herein, is one that originates from a source foreign to the particular cell (e.g., from a different species), or, if from the same source, is modified from its original form or place in the genome. Thus, a heterologous nucleic acid operably linked to a promoter is from a source different from that from which the promoter was derived, or, if from the same source, is modified from its original form or place in the genome. The heterologous sequence may be stably introduced, e.g., by transfection, transformation, conjugation or transduction, into the genome of the host microorganism cell, wherein techniques may be applied which will depend on the cell and the sequence that is to be introduced. Various techniques are known to a person skilled in the art and are, e.g., disclosed in Sambrook et al., Molecular Cloning: A Laboratory Manual, 2nd Ed., Cold Spring Harbor Laboratory Press, Cold Spring Harbor, N.Y. (1989). The term "mutant" cell or microorganism as used within the context of the disclosure refers to a cell or microorganism which is genetically modified.

The term "endogenous," within the context of the disclosure refers to any polynucleotide, polypeptide or protein sequence which is a natural part of a cell and is occurring at its natural location in the cell chromosome and of which the control of expression has not been altered compared to the natural control mechanism acting on its expression. The term "exogenous" refers to any polynucleotide, polypeptide or protein sequence which originates from outside the cell under study and not a natural part of the cell or which is not occurring at its natural location in the cell chromosome or plasmid.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g., a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e., in the genome of a non-genetically engineered organism) is referred to herein as a "heterologous promoter," even though the promoter may be derived from the same species (or, in some cases, the same organism) as the gene to which it is linked.

The term "modified activity" of a protein or an enzyme relates to a change in activity of the protein or the enzyme compared to the wild type, i.e., natural, activity of the protein or enzyme. The modified activity can either be an abolished, impaired, reduced or delayed activity of the protein or enzyme compared to the wild type activity of the protein or the enzyme but can also be an accelerated or an enhanced activity of the protein or the enzyme compared to the wild type activity of the protein or the enzyme. A modified activity of a protein or an enzyme is obtained by modified expression of the protein or enzyme or is obtained by expression of a modified, i.e., mutant form of the protein or enzyme. A modified activity of an enzyme further relates to a modification in the apparent Michaelis constant Km and/or the apparent maximal velocity (Vmax) of the enzyme.

The term "modified expression" of a gene relates to a change in expression compared to the wild type expression of the gene in any phase of the production process of the encoded protein. The modified expression is either a lower or higher expression compared to the wild type, wherein the term "higher expression" is also defined as "overexpression" of the gene in the case of an endogenous gene or "expression" in the case of a heterologous gene that is not present in the wild type strain. Lower expression or reduced expression is obtained by means of common well-known technologies for a skilled person (such as the usage of siRNA, CrispR, CrispRi, riboswitches, recombineering, homologous recombination, ssDNA mutagenesis, RNAi, miRNA, asRNA, mutating genes, knocking-out genes, transposon mutagenesis, . . . ) which are used to change the genes in such a way that they are less-able (i.e., statistically significantly "less-able" compared to a functional wild-type gene) or completely unable (such as knocked-out genes) to produce functional final products. The term "riboswitch" as used herein is defined to be part of the messenger RNA that folds into intricate structures that block expression by interfering with translation. Binding of an effector molecule induces conformational change(s) permitting regulated expression post-transcriptionally. Next to changing the gene of interest in such a way that lower expression is obtained as described above, lower expression can also be obtained by changing the transcription unit, the promoter, an untranslated region, the ribosome binding site, the Shine Dalgarno sequence or the transcription terminator. Lower expression or reduced expression can for instance be obtained by mutating one or more base pairs in the promoter sequence or changing the promoter sequence fully to a constitutive promoter with a lower expression strength compared to the wild type or an inducible promoter which result in regulated expression or a repressible promoter which results in regulated expression Overexpression or expression is obtained by means of common well-known technologies for a skilled person (such as the usage of artificial transcription factors, de novo design of a promoter sequence, ribosome engineering, introduction or re-introduction of an expression module at euchromatin, usage of high-copy-number plasmids), wherein the gene is part of an "expression cassette" which relates to any sequence in which a promoter sequence, untranslated region sequence (containing either a ribosome binding sequence, Shine Dalgarno or Kozak sequence), a coding sequence and optionally a transcription terminator is present, and leading to the expression of a functional active protein. The expression is either constitutive or regulated.

The term "constitutive expression" is defined as expression that is not regulated by transcription factors other than the subunits of RNA polymerase (e.g., the bacterial sigma factors like $\sigma^{70}$, $\sigma^{54}$, or related σ-factors and the yeast mitochondrial RNA polymerase specificity factor MTF1 that co-associate with the RNA polymerase core enzyme) under certain growth conditions. Non-limiting examples of such transcription factors are CRP, Lad, ArcA, Cra, IclR in *E. coli*, or, Aft2p, Crz1p, Skn7 in *Saccharomyces cerevisiae*, or, DeoR, GntR, Fur in *B. subtilis*. These transcription factors bind on a specific sequence and may block or enhance expression in certain growth conditions. The RNA polymerase is the catalytic machinery for the synthesis of RNA from a DNA template. RNA polymerase binds a specific sequence to initiate transcription, for instance via a sigma factor in prokaryotic hosts or via MTF1 in yeasts. Constitutive expression offers a constant level of expression with no need for induction or repression.

The term "expression by a natural inducer" is defined as a facultative or regulatory expression of a gene that is only expressed upon a certain natural condition of the host (e.g., organism being in labor, or during lactation), as a response to an environmental change (e.g., including but not limited to hormone, heat, cold, light, oxidative or osmotic stress/signaling), or dependent on the position of the developmental stage or the cell cycle of the host cell including but not limited to apoptosis and autophagy.

The term "control sequences" refers to sequences recognized by the cells transcriptional and translational systems, allowing transcription and translation of a polynucleotide sequence to a polypeptide. Such DNA sequences are thus necessary for the expression of an operably linked coding sequence in a particular cell or organism. Such control sequences can be, but are not limited to, promoter sequences, ribosome binding sequences, Shine Dalgarno sequences, Kozak sequences, transcription terminator sequences. The control sequences that are suitable for prokaryotes, for example, include a promoter, optionally an operator sequence, and a ribosome binding site. Eukaryotic cells are known to utilize promoters, polyadenylation signals, and enhancers. DNA for a presequence or secretory leader may be operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it affects the transcription of the sequence; or a ribosome binding site is operably linked to a coding sequence if it is positioned so as to facilitate translation. The control sequences can furthermore be controlled with external chemicals, such as, but not limited to, IPTG, arabinose, lactose, allo-lactose, rhamnose or fucose via an inducible promoter or via a genetic circuit that either induces or represses the transcription or translation of the polynucleotide to a polypeptide.

Generally, "operably linked" means that the DNA sequences being linked are contiguous, and, in the case of a secretory leader, contiguous and in reading phase. However, enhancers do not have to be contiguous.

The term "wild type" refers to the commonly known genetic or phenotypical situation as it occurs in nature.

The term "modified expression of a protein" as used herein refers to i) higher expression or overexpression of an endogenous protein, ii) expression of a heterologous protein or iii) expression and/or overexpression of a variant protein that has a higher activity compared to the wild-type (i.e., native) protein.

As used herein, the term "mammary cell(s)" generally refers to mammary epithelial cell(s), mammary-epithelial luminal cell(s), or mammalian epithelial alveolar cell(s), or any combination thereof. As used herein, the term "mammary-like cell(s)" generally refers to cell(s) having a phenotype/genotype similar (or substantially similar) to natural mammary cell(s) but is/are derived from non-mammary cell source(s). Such mammary-like cell(s) may be engineered to remove at least one undesired genetic component and/or to include at least one predetermined genetic construct that is typical of a mammary cell. Non-limiting examples of mammary-like cell(s) may include mammary epithelial-like cell(s), mammary epithelial luminal-like cell(s), non-mammary cell(s) that exhibits one or more characteristics of a cell of a mammary cell lineage, or any combination thereof. Further non-limiting examples of mammary-like cell(s) may include cell(s) having a phenotype similar (or substantially similar) to natural mammary cell(s), or more particularly a phenotype similar (or substantially similar) to natural mammary epithelial cell(s). A cell with a phenotype or that exhibits at least one characteristic similar to (or substantially similar to) a natural mammary cell or a mammary epithelial cell may comprise a cell (e.g., derived from a mammary cell lineage or a non-mammary cell lineage) that exhibits either naturally, or has been engineered to, be capable of expressing at least one milk component.

As used herein, the term "non-mammary cell(s)" may generally include any cell of non-mammary lineage. In the context of the disclosure, a non-mammary cell can be any mammalian cell capable of being engineered to express at least one milk component. Non-limiting examples of such non-mammary cell(s) include hepatocyte(s), blood cell(s), kidney cell(s), cord blood cell(s), epithelial cell(s), epidermal cell(s), myocyte(s), fibroblast(s), mesenchymal cell(s), or any combination thereof. In some instances, molecular biology and genome editing techniques can be engineered to eliminate, silence, or attenuate myriad genes simultaneously.

Throughout the application, unless explicitly stated otherwise, the expressions "capable of . . . <verb>" and "capable to . . . <verb>" are preferably replaced with the active voice of the verb and vice versa. For example, the expression "capable of expressing" is preferably replaced with "expresses" and vice versa, i.e., "expresses" is preferably replaced with "capable of expressing."

"Variant(s)" as the term is used herein, is a polynucleotide or polypeptide that differs from a reference polynucleotide or polypeptide respectively but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to the persons skilled in the art.

The term "derivative" of a polypeptide, as used herein, is a polypeptide which may contain deletions, additions or substitutions of amino acid residues within the amino acid sequence of the polypeptide, but which result in a silent change, thus producing a functionally equivalent polypeptide. Amino acid substitutions may be made based on similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; planar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Within the context of this disclosure, a derivative polypeptide as used herein, refers to a polypeptide capable of exhibiting a substantially similar in vitro and/or in vivo activity as the original polypeptide as judged by any of a number of criteria, including but not limited to enzymatic activity, and which may be differentially modified during or after translation. Furthermore, non-classical amino acids or chemical amino acid analogues can be introduced as a substitution or addition into the original polypeptide sequence.

In some embodiments, the disclosure contemplates making functional variants by modifying the structure of an enzyme as used in the disclosure. Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide.

The term "functional homolog" as used herein describes those molecules that have sequence similarity (in other words, homology) and also share at least one functional characteristic such as a biochemical activity (Altenhoff et al., PLoS Comput. Biol. 8 (2012) e1002514). Functional homologs will typically give rise to the same characteristics to a similar, but not necessarily the same, degree. Functionally homologous proteins give the same characteristics where the quantitative measurement produced by one homolog is at least 10 percent of the other; more typically, at least 20 percent, between about 30 percent and about 40 percent; for example, between about 50 percent and about 60 percent; between about 70 percent and about 80 percent; or between about 90 percent and about 95 percent; between about 98 percent and about 100 percent, or greater than 100 percent of that produced by the original molecule. Thus, where the molecule has enzymatic activity the functional homolog will have the above-recited percent enzymatic activities compared to the original enzyme. Where the molecule is a DNA-binding molecule (e.g., a polypeptide) the homolog will have the above-recited percentage of binding affinity as measured by weight of bound molecule compared to the original molecule.

A functional homolog and the reference polypeptide may be naturally occurring polypeptides, and the sequence similarity may be due to convergent or divergent evolutionary events. Functional homologs are sometimes referred to as orthologs, where "ortholog," refers to a homologous gene or protein that is the functional equivalent of the referenced gene or protein in another species.

Orthologous genes are homologous genes in different species that originate by vertical descent from a single gene of the last common ancestor, wherein the gene and its main function are conserved. A homologous gene is a gene inherited in two species by a common ancestor.

The term "ortholog" when used in reference to an amino acid or nucleotide/nucleic acid sequence from a given species refers to the same amino acid or nucleotide/nucleic acid sequence from a different species. It should be understood that two sequences are orthologs of each other when they are derived from a common ancestor sequence via linear descent and/or are otherwise closely related in terms of both their sequence and their biological function. Orthologs will usually have a high degree of sequence identity but may not (and often will not) share 100% sequence identity.

Paralogous genes are homologous genes that originate by a gene duplication event. Paralogous genes often belong to the same species, but this is not necessary. Paralogs can be split into in-paralogs (paralogous pairs that arose after a speciation event) and out-paralogs (paralogous pairs that arose before a speciation event). Between species out-paralogs are pairs of paralogs that exist between two organisms due to duplication before speciation. Within species out-paralogs are pairs of paralogs that exist in the same organism, but whose duplication event happened after speciation. Paralogs typically have the same or similar function.

Functional homologs can be identified by analysis of nucleotide and polypeptide sequence alignments. For example, performing a query on a database of nucleotide or polypeptide sequences can identify homologs of the polypeptide of interest like, e.g., a biomass-modulating polypeptide, a glycosyltransferase, a protein involved in nucleotide-activated sugar synthesis or a membrane protein. Sequence analysis can involve BLAST, Reciprocal BLAST, or PSI-BLAST analysis of non-redundant databases using amino acid sequence of a biomass-modulating polypeptide, a glycosyltransferase, a protein involved in nucleotide-activated sugar synthesis or a membrane protein, respectively, as the reference sequence. Amino acid sequence is, in some instances, deduced from the nucleotide sequence. Typically, those polypeptides in the database that have greater than 40 percent sequence identity are candidates for further evaluation for suitability as a biomass-modulating polypeptide, a glycosyltransferase, a protein involved in nucleotide-activated sugar synthesis or a membrane transporter protein, respectively. Amino acid sequence similarity allows for conservative amino acid substitutions, such as substitution of one hydrophobic residue for another or substitution of one polar residue for another or substitution of one acidic amino acid for another or substitution of one basic amino acid for another etc. Preferably, by conservative substitutions is intended combinations such as glycine by alanine and vice versa; valine, isoleucine and leucine by methionine and vice versa; aspartate by glutamate and vice versa; asparagine by glutamine and vice versa; serine by threonine and vice versa; lysine by arginine and vice versa; cysteine by methionine and vice versa; and phenylalanine and tyrosine by tryptophan and vice versa. If desired, manual inspection of such candidates can be carried out in order to narrow the number of candidates to be further evaluated. Manual inspection can be performed by selecting those candidates that appear to have domains present in productivity-modulating polypeptides, e.g., conserved functional domains.

"Fragment," with respect to a polynucleotide, refers to a clone or any part of a polynucleotide molecule, particularly a part of a polynucleotide that retains a usable, functional characteristic of the full-length polynucleotide molecule. Useful fragments include oligonucleotides and polynucleotides that may be used in hybridization or amplification technologies or in the regulation of replication, transcription or translation. A "polynucleotide fragment" refers to any subsequence of a polynucleotide SEQ ID NO (or Genbank NO.), typically, comprising or consisting of at least about 9, 10, 11, 12 consecutive nucleotides, for example at least about 30 nucleotides or at least about 50 nucleotides of any of the polynucleotide sequences provided herein. Exemplary fragments can additionally or alternatively include fragments that comprise, consist essentially of, or consist of a region that encodes a conserved family domain of a polypeptide. Exemplary fragments can additionally or alternatively include fragments that comprise a conserved domain of a polypeptide. As such, a fragment of a polynucleotide SEQ ID NO (or Genbank NO.) preferably means a nucleotide sequence which comprises or consists of the polynucleotide SEQ ID NO (or Genbank NO.) wherein no more than 200, 150, 100, 50 or 25 consecutive nucleotides are missing, preferably no more than 50 consecutive nucleotides are missing, and which retains a usable, functional characteristic (e.g., activity) of the full-length polynucleotide molecule which can be assessed by the skilled person through routine experimentation. Alternatively, a fragment of a polynucleotide SEQ ID NO (or Genbank NO.) preferably means a nucleotide sequence which comprises or consists of an amount of consecutive nucleotides from the polynucleotide SEQ ID NO (or Genbank NO.) and wherein the amount of consecutive nucleotides is at least 50.0%, 60.0%, 70.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 95.5%, 96.0%, 96.5%, 97.0%, 97.5%, 98.0%, 98.5%, 99.0%, 99.5%, 100%, preferably at least 80%, more preferably at least 87%, even more preferably at least 90%, even more preferably at least 95%, most preferably at least 97%, of the full-length of the polynucleotide SEQ ID NO (or Genbank NO.) and retains a usable, functional characteristic (e.g., activity) of the full-length polynucleotide molecule. As such, a fragment of a polynucleotide SEQ ID NO (or Genbank NO.) preferably means a nucleotide sequence which comprises or consists of the polynucleotide SEQ ID NO (or Genbank NO.), wherein an amount of consecutive nucleotides is missing and wherein the amount is no more than 50.0%, 40.0%, 30.0% of the full-length of the polynucleotide SEQ ID NO (or Genbank NO.), preferably no more than 20.0%, 15.0%, 10.0%, 9.0%, 8.0%, 7.0%, 6.0%, 5.0%, 4.5%, 4.0%, 3.5%, 3.0%, 2.5%, 2.0%, 1.5%, 1.0%, 0.5%, more preferably no more than 15%, even more preferably no more than 10%, even more preferably no more than 5%, most preferably no more than 2.5%, of the full-length of the polynucleotide SEQ ID NO (or Genbank NO.) and wherein the fragment retains a usable, functional characteristic (e.g., activity) of the full-length polynucleotide molecule which can be routinely assessed by the skilled person.

Throughout the application, the sequence of a polynucleotide can be represented by a SEQ ID NO or alternatively by a Genbank NO. Therefore, the terms "polynucleotide SEQ ID NO" and "polynucleotide Genbank NO." can be interchangeably used, unless explicitly stated otherwise.

Fragments may additionally or alternatively include subsequences of polypeptides and protein molecules, or a subsequence of the polypeptide. In some cases, the fragment or domain is a subsequence of the polypeptide which performs at least one biological function of the intact polypeptide in substantially the same manner, preferably to a similar extent, as does the intact polypeptide. A "subsequence of the polypeptide" as defined herein refers to a sequence of contiguous amino acid residues derived from the polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, for example at least about 20 amino acid residues in length, for example at least about 30 amino acid residues in length. As such, a fragment of a polypeptide SEQ ID NO (or UniProt ID or Genbank NO.) preferably means a polypeptide sequence which comprises or consists of the polypeptide SEQ ID NO (or UniProt ID or Genbank NO.) wherein no more than 80, 60, 50, 40, 30, 20 or 15 consecutive amino acid residues are missing, preferably no more than 40 consecutive amino acid residues are missing, and performs at least one biological function of the intact polypeptide in substantially the same manner, preferably to a similar or greater extent, as does the intact polypeptide which can be routinely assessed by the skilled person. Alternatively, a fragment of a polypeptide SEQ ID NO (or UniProt ID or Genbank NO.) preferably means a polypeptide sequence which comprises or consists of an amount of consecutive amino acid residues from the polypeptide SEQ ID NO (or UniProt ID or Genbank NO.) and wherein the amount of consecutive amino acid residues is at least 50.0%, 60.0%, 70.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 95.5%, 96.0%, 96.5%, 97.0%, 97.5%, 98.0%, 98.5%, 99.0%, 99.5%, 100%, preferably at least 80%, more preferably at least 87%, even more preferably at least 90%, even more preferably at least 95%, most preferably at least 97% of the full-length of the polypeptide SEQ ID NO (or UniProt ID or Genbank NO.) and which performs at least one biological function of the intact polypeptide in substantially the same manner, preferably to a similar or greater extent, as does the intact polypeptide which can be routinely assessed by the skilled person. As such, a fragment of a polypeptide SEQ ID NO (or UniProt ID or Genbank NO.) preferably means a polypeptide sequence which comprises or consists of the polypeptide SEQ ID NO (or UniProt ID or Genbank NO.), wherein an amount of consecutive amino acid residues is missing and wherein the amount is no more than 50.0%, 40.0%, 30.0% of the full-length of the polypeptide SEQ ID NO (or UniProt ID or Genbank NO.), preferably no more than 20.0%, 15.0%, 10.0%, 9.0%, 8.0%, 7.0%, 6.0%, 5.0%, 4.5%, 4.0%, 3.5%, 3.0%, 2.5%, 2.0%, 1.5%, 1.0%, 0.5%, more preferably no more than 15%, even more preferably no more than 10%, even more preferably no more than 5%, most preferably no more than 2.5%, of the full-length of the polypeptide SEQ ID NO (or UniProt ID or Genbank NO.) and which performs at least one biological function of the intact polypeptide in substantially the same manner, preferably to a similar or greater extent, as does the intact polypeptide which can be routinely assessed by the skilled person.

Throughout the application, the sequence of a polypeptide can be represented by a SEQ ID NO or alternatively by a UniProt ID or Genbank NO. Therefore, the terms "polypeptide SEQ ID NO" and "polypeptide UniProt ID" and "polypeptide Genbank NO." can be interchangeably used, unless explicitly stated otherwise.

Preferentially, a fragment of a polypeptide is a functional fragment that has at least one property or activity of the polypeptide from which it is derived, preferably to a similar or greater extent. A functional fragment can for example, include a functional domain or conserved domain of a polypeptide. It is understood that a polypeptide or a fragment thereof may have conservative amino acid substitutions which have substantially no effect on the polypeptide's activity. By "conservative substitutions" is intended substitutions of one hydrophobic amino acid for another or substitution of one polar amino acid for another or substitution of one acidic amino acid for another or substitution of one basic amino acid for another etc. Preferably, by conservative substitutions is intended combinations such as glycine by alanine and vice versa; valine, isoleucine and leucine by methionine and vice versa; aspartate by glutamate and vice versa; asparagine by glutamine and vice versa; serine by threonine and vice versa; lysine by arginine and vice versa; cysteine by methionine and vice versa; and phenylalanine and tyrosine by tryptophan and vice versa. A domain can be characterized, for example, by a Pfam (El-Gebali et al., Nucleic Acids Res. 47 (2019) D427-D432) or Conserved Domain Database (CDD)(Lu et al., Nucleic Acids Res. 48 (2020) D265-D268) designation. The content of each database is fixed at each release and is not to be changed. When the content of a specific database is changed, this specific database receives a new release version with a new release date. All release versions for each database with their corresponding release dates and specific content as annotated at these specific release dates are available and known to those skilled in the art. The PFAM database used herein was Pfam version 33.1 released on Jun. 11, 2020. Protein sequence information and functional information can be provided by a comprehensive resource for protein sequence and annotation data like, e.g., the Universal Protein Resource (UniProt) (Nucleic Acids Res. 2021, 49(D1), D480-D489). UniProt comprises the expertly and richly curated protein database called the UniProt Knowledgebase (UniProtKB), together with the UniProt Reference Clusters (UniRef) and the UniProt Archive (UniParc). The UniProt identifiers (UniProt ID) are unique for each protein present in the database. UniProt IDs as used herein are the UniProt IDs in the UniProt database version of 5 May 2021. Proteins that do not have a UniProt ID are referred herein using the respective Genbank Accession number (Genbank NO.) as present in the NIH genetic sequence database (Nucleic Acids Res. 2013, 41(D1), D36-D42) version of 5 May 2021.

The term "glycosyltransferase" as used herein refers to an enzyme capable to catalyze the transfer of sugar moieties from activated donor molecules to specific acceptor molecules, forming glycosidic bonds. The as such synthesized oligosaccharides can be of the linear type or of the branched type and can contain multiple monosaccharide building blocks. A classification of glycosyltransferases using nucleotide diphospho-sugar, nucleotide monophospho-sugar and sugar phosphates and related proteins into distinct sequence-based families has been described (Campbell et al., Biochem. J. 326, 929-939 (1997)) and is available on the CAZy (CArbohydrate-Active EnZymes) website.

As used herein the glycosyltransferase can be selected from the list comprising but not limited to: galactosyltransferases (e.g., beta-1,3-galactosyltransferases, beta-1,4-galactosyltransferases, alpha-1,3-galactosyltransferases, alpha-1,4-galactosyltransferases), glucosyltransferases, mannosyltransferases, glucosaminyltransferases, N-acetylglucosaminyltransferases (e.g., beta-1,3-N-acetylglucosaminyltransferases, beta-1,6-N-acetylglucosaminyltransferases), N-acetylgalactosaminyltransferases (e.g., alpha-1,3-N-acetylgalactosaminyltransferases, beta-1,3-N-acetylgalactosaminyltransferases), N-acetylmannosaminyltransferases, xylosyltransferases, rhamnosyltransferases, N-acetylrhamnosyltransferases, UDP-4-amino-4,6-dideoxy-N-acetyl-beta-L-altrosamine transaminases, UDP-N-acetylglucosamine enolpyruvyl transferases and fucosaminyltransferases.

Galactosyltransferases are glycosyltransferases that transfer a galactosyl group (Gal) from a UDP-galactose (UDP-Gal) donor onto a glycan acceptor. Galactosyltransferases comprise beta-1,3-galactosyltransferases, beta-1,4-galactosyltransferases, alpha-1,3-galactosyltransferases and alpha-1,4-galactosyltransferases that transfer a Gal residue from UDP-Gal onto a glycan acceptor via alpha- or beta-glycosidic bonds. Galactosyltransferases can be found but are not limited to the GT2, GT6, GT8, GT25 and GT92 CAZy families. Glucosyltransferases are glycosyltransferases that transfer a glucosyl group (Glc) from a UDP-glucose (UDP-Glc) donor onto a glycan acceptor. Glucosyltransferases comprise alpha-glucosyltransferases, beta-1,2-glucosyltransferases, beta-1,3-glucosyltransferases and beta-1,4-glucosyltransferases that transfer a Glc residue from UDP-Glc onto a glycan acceptor via alpha- or beta-glycosidic bonds. Glucosyltransferases can be found but are not limited to the GT1, GT4 and GT25 CAZy families. Mannosyltransferases are glycosyltransferases that transfer a mannose group (Man) from a GDP-mannose (GDP-Man) donor onto a glycan acceptor. Mannosyltransferases comprise alpha-1,2-mannosyltransferases, alpha-1,3-mannosyltransferases and alpha-1,6-mannosyltransferases that transfer a Man residue from GDP-Man onto a glycan acceptor via alpha-glycosidic bonds. Mannosyltransferases can be found but are not limited to the GT22, GT39, GT62 and GT69 CAZy families. N-acetylglucosaminyltransferases are glycosyltransferases that transfer an N-acetylglucosamine group (GlcNAc) from a UDP-N-acetylglucosamine (UDP-GlcNAc) donor onto a glycan acceptor. N-acetylglucosaminyltransferases can be found but are not limited to GT2 and GT4 CAZy families.

N-acetylgalactosaminyltransferases are glycosyltransferases that transfer an N-acetylgalactosamine group (GalNAc) from a UDP-N-acetylgalactosamine (UDP-GalNAc) donor onto a glycan acceptor. N-acetylgalactosaminyltransferases can be found but are not limited to GT7, GT12 and GT27 CAZy families. N-acetylmannosaminyltransferases are glycosyltransferases that transfer an N-acetylmannosamine group (ManNAc) from a UDP-N-acetylmannosamine (UDP-ManNAc) donor onto a glycan acceptor. Xylosyltransferases are glycosyltransferases that transfer a xylose residue (Xyl) from a UDP-xylose (UDP-Xyl) donor onto a glycan acceptor. Xylosyltransferases can be found but are not limited to GT61 and GT77 CAZy families. Rhamnosyltransferases are glycosyltransferases that transfer a rhamnose residue from a GDP-rhamnose donor onto a glycan acceptor. Rhamnosyltransferases can be found but are not limited to the GT1, GT2 and GT102 CAZy families. N-acetylrhamnosyltransferases are glycosyltransferases that transfer an N-acetylrhamnosamine residue from a UDP-N-acetyl-L-rhamnosamine donor onto a glycan acceptor. UDP-4-amino-4,6-dideoxy-N-acetyl-beta-L-altrosamine transaminases are glycosyltransferases that use a UDP-2-acetamido-2,6-dideoxy-L-arabino-4-hexulose in the biosynthesis of pseudaminic acid, which is a sialic acid-like sugar that is used to modify flagellin. UDP-N-acetylglucosamine enolpyruvyl transferases (murA) are glycosyltransferases that transfer an enolpyruvyl group from phosphoenolpyruvate (PEP) to UDP-N-acetylglucosamine (UDPAG) to form UDP-N-acetylglucosamine enolpyruvate. Fucosaminyltransferases are glycosyltransferases that transfer an N-acetylfucosamine residue from a dTDP-N-acetylfucosamine or a UDP-N-acetylfucosamine donor onto a glycan acceptor.

The terms "nucleotide-sugar," "nucleotide-activated sugar" or "activated sugar" are used herein interchangeably and refer to activated forms of monosaccharides. Examples of activated monosaccharides include but are not limited to UDP-galactose (UDP-Gal), UDP-N-acetylglucosamine (UDP-GlcNAc), UDP-N-acetylgalactosamine (UDP-GalNAc), UDP-N-acetylmannosamine (UDP-ManNAc), GDP-mannose (GDP-Man), UDP-glucose (UDP-Glc), UDP-2-acetamido-2,6-dideoxy-L-arabino-4-hexulose, UDP-2-acetamido-2,6-dideoxy-L-lyxo-4-hexulose, UDP-N-acetyl-L-rhamnosamine (UDP-L-RhaNAc or UDP-2-acetamido-2,6-dideoxy-L-mannose), dTDP-N-acetylfucosamine, UDP-N-acetylfucosamine (UDP-L-FucNAc or UDP-2-acetamido-2,6-dideoxy-L-galactose), UDP-N-acetyl-L-pneumosamine (UDP-L-PneNAC or UDP-2-acetamido-2,6-dideoxy-L-talose), UDP-N-acetylmuramic acid, UDP-N-acetyl-L-quinovosamine (UDP-L-QuiNAc or UDP-2-acetamido-2,6-dideoxy-L-glucose), GDP-L-quinovose, GDP-rhamnose, or UDP-xylose. Nucleotide-sugars act as glycosyl donors in glycosylation reactions. Glycosylation reactions are reactions that are catalyzed by glycosyltransferases.

"Oligosaccharide" as the term is used herein and as generally understood in the state of the art, refers to a saccharide polymer containing a small number, typically three to twenty, of simple sugars, i.e., monosaccharides. The monosaccharides as used herein are reducing sugars. The oligosaccharides can be reducing or non-reducing sugars and have a reducing and a non-reducing end. A reducing sugar is any sugar that is capable of reducing another compound and is oxidized itself, that is, the carbonyl carbon of the sugar is oxidized to a carboxyl group. The oligosaccharide as used in the disclosure can be a linear structure or can include branches. The linkage (e.g., glycosidic linkage, galactosidic linkage, glucosidic linkage, etc.) between two sugar units can be expressed, for example, as 1,4, 1→4, or (1-4), used interchangeably herein. For example, the terms "Gal-b1,4-Glc," "β-Gal-(1→4)-Glc," "Galbeta1-4-Glc" and "Gal-b(1-4)-Glc" have the same meaning, i.e., a beta-glycosidic bond links carbon-1 of galactose (Gal) with the carbon-4 of glucose (Glc). Each monosaccharide can be in the cyclic form (e.g., pyranose of furanose form). Linkages between the individual monosaccharide units may include alpha 1→2, alpha 1→3, alpha 1→4, alpha 1→6, alpha 2→1, alpha 2→3, alpha 2→4, alpha 2→6, beta 1→2, beta 1→3, beta 1→4, beta 1→6, beta 2→1, beta 2→3, beta 2→4, and beta 2→6. An oligosaccharide can contain both alpha- and beta-glycosidic bonds or can contain only beta-glycosidic bonds. Preferably, the oligosaccharide as described herein contains monosaccharides selected from the list as used herein below. Examples of oligosaccharides include but are not limited to mammalian milk oligosaccharides and human milk oligosaccharides. As used herein, "LNB (lacto-N-biose)-based oligosaccharide" refers to an oligosaccharide as defined herein which contains a LNB at its reducing end. As used herein, "LacNAc (N-acetyllactosamine)-based oligosaccharide" refers to an oligosaccharide as defined herein which contains a LacNAc at its reducing end.

The term "monosaccharide" as used herein refers to a sugar that is not decomposable into simpler sugars by hydrolysis, is classed either an aldose or ketose, and contains one or more hydroxyl groups per molecule. Monosaccharides are saccharides containing only one simple sugar. Examples of monosaccharides comprise Hexose, D-Glucopyranose, D-Galactofuranose, D-Galactopyranose, L-Galactopyranose, D-Mannopyranose, D-Allopyranose, L-Altropyranose, D-Gulopyranose, L-Idopyranose, D-Talopyranose, D-Ribofuranose, D-Ribopyranose, D-Arabinofuranose, D-Arabinopyranose, L-Arabinofuranose, L-Arabinopyranose, D-Xylopyranose, D-Lyxopyranose, D-Erythrofuranose, D-Threofuranose, Heptose, L-glycero-D-manno-Heptopyranose (LDmanHep), D-glycero-D-manno-Heptopyranose (DDmanHep), 6-Deoxy-L-altropyranose, 6-Deoxy-D-gulopyranose, 6-Deoxy-D-talopyranose, 6-Deoxy-D-galactopyranose, 6-Deoxy-L-galactopyranose, 6-Deoxy-D-mannopyranose, 6-Deoxy-L-mannopyranose, 6-Deoxy-D-glucopyranose, 2-Deoxy-D-arabino-hexose, 2-Deoxy-D-erythro-pentose, 2,6-Dideoxy-D-arabino-hexopyranose, 3,6-Dideoxy-D-arabino-hexopyranose, 3,6-Dideoxy-L-arabino-hexopyranose, 3,6-Dideoxy-D-xylo-hexopyranose, 3,6-Dideoxy-D-ribo-hexopyranose, 2,6-Dideoxy-D-ribo-hexopyranose, 3,6-Dideoxy-L-xylo-hexopyranose, 2-Amino-2-deoxy-D-glucopyranose, 2-Amino-2-deoxy-D-galactopyranose, 2-Amino-2-deoxy-D-mannopyranose, 2-Amino-2-deoxy-D-allopyranose, 2-Amino-2-deoxy-L-altropyranose, 2-Amino-2-deoxy-D-gulopyranose, 2-Amino-2-deoxy-L-idopyranose, 2-Amino-2-deoxy-D-talopyranose, 2-Acetamido-2-deoxy-D-glucopyranose, 2-Acetamido-2-deoxy-D-galactopyranose, 2-Acetamido-2-deoxy-D-mannopyranose, 2-Acetamido-2-deoxy-D-allopyranose, 2-Acetamido-2-deoxy-L-altropyranose, 2-Acetamido-2-deoxy-D-gulopyranose, 2-Acetamido-2-deoxy-L-idopyranose, 2-Acetamido-2-deoxy-D-talopyranose, 2-Acetamido-2,6-dideoxy-D-galactopyranose, 2-Acetamido-2,6-dideoxy-L-galactopyranose, 2-Acetamido-2,6-dideoxy-L-mannopyranose, 2-Acetamido-2,6-dideoxy-D-glucopyranose, 2-Acetamido-2,6-dideoxy-L-altropyranose, 2-Acetamido-2,6-dideoxy-D-talopyranose, Erythritol, Arabinitol, Xylitol, Ribitol, Glucitol, Galactitol, Mannitol, D-ribo-Hex-2-ulopyranose, D-arabino-Hex-2-ulofuranose (D-fructofuranose), D-arabino-Hex-2-ulopyranose, L-xylo-Hex-2-ulopyranose, D-lyxo-Hex-2-ulopyranose, D-threo-Pent-2-ulopyranose, D-altro-Hept-2-ulopyranose, 3-C-(Hydroxymethyl)-D-erythofuranose, 2,4,6-Trideoxy-2,4-diamino-D-glucopyranose, 6-Deoxy-3-O-methyl-D-glucose, 3-O-Methyl-D-rhamnose, 2,6-Dideoxy-3-methyl-D-ribo-hexose, 2-Amino-3-O—[(R)-1-carboxyethyl]-2-deoxy-D-glucopyranose, 2-Acetamido-3-O—[(R)-carboxyethyl]-2-deoxy-D-glucopyranose, 2-Glycolylamido-3-O—[(R)-1-carboxyethyl]-2-deoxy-D-glucopyranose, glucose, galactose, N-acetylglucosamine, glucosamine, mannose, xylose, N-acetylmannosamine, N-acetylgalactosamine, galactosamine, rhamnose, fructose and polyols.

With the term "polyol" is meant an alcohol containing multiple hydroxyl groups. For example, glycerol, sorbitol, or mannitol.

The term "disaccharide" as used herein refers to a saccharide composed of two monosaccharide units. Examples of di saccharides comprise lactose (Gal-b1,4-Glc), lacto-N-biose (Gal-b1,3-GlcNAc), N-acetyllactosamine (Gal-b1,4-GlcNAc), LacDiNAc (GalNAc-b1,4-GlcNAc), N-acetylgalactosaminylglucose (GalNAc-b1,4-Glc).

As used herein, "mammalian milk oligosaccharide" or MMO refers to neutral non-fucosylated mammalian milk oligosaccharides such as but not limited to lacto-N-triose II, lacto-N-tetraose, lacto-N-neotetraose, lacto-N-hexaose, lacto-N-neohexaose, para-lacto-N-hexaose and/or galactosylated chitosan.

Mammalian milk oligosaccharides comprise oligosaccharides present in milk found in any phase during lactation including colostrum milk from humans and mammals including but not limited to cows (*Bos Taurus*), sheep (*Ovis aries*), goats (*Capra aegagrus hircus*), bactrian camels (*Camelus bactrianus*), horses (*Equus ferus caballus*), pigs (*Sus scropha*), dogs (*Canis lupus familiaris*), ezo brown bears (*Ursus arctos yesoensis*), polar bear (*Ursus maritimus*), Japanese black bears (*Ursus thibetanus japonicus*), striped skunks (*Mephitis mephitis*), hooded seals (*Cystophora cristata*), Asian elephants (*Elephas maximus*), African elephant (*Loxodonta africana*), giant anteater (*Myrmecophaga tridactyla*), common bottlenose dolphins (*Tursiops truncates*), northern minke whales (*Balaenoptera acutorostrata*), tammar wallabies (*Macropus eugenii*), red kangaroos (*Macropus rufus*), common brushtail possum (*Trichosurus vulpecula*), koalas (*Phascolarctos cinereus*), eastern quolls (*Dasyurus viverrinus*), platypus (*Ornithorhynchus anatinus*). Human milk oligosaccharides (HMOs) are also known as human identical milk oligosaccharides which are chemically identical to the human milk oligosaccharides found in human breast milk but which are biotechnologically-produced (e.g., using cell free systems or cells and organisms comprising a bacterium, a fungus, a yeast, a plant, animal, or protozoan cell, preferably genetically engineered cells and organisms). Human identical milk oligosaccharides are marketed under the name HiMO.

As used herein, "lactose-based mammalian milk oligosaccharide (MMO)" refers to a MMO as defined herein which contains a lactose at its reducing end.

A "fucosylated oligosaccharide" as used herein and as generally understood in the state of the art is an oligosaccharide that is carrying a fucose-residue. Such fucosylated oligosaccharide is a saccharide structure comprising at least three monosaccharide subunits linked to each other via glycosidic bonds, wherein at least one of the monosaccharide subunit is a fucose. A fucosylated oligosaccharide can contain more than one fucose residue, e.g., two, three or more. A fucosylated oligosaccharide can be a neutral oligosaccharide or a charged oligosaccharide, e.g., also comprising sialic acid structures. Fucose can be linked to other monosaccharide subunits comprising glucose, galactose, GlcNAc via alpha-glycosidic bonds comprising alpha-1,2 alpha-1,3, alpha-1,4, alpha-1,6 linkages.

Examples comprise 2'-fucosyllactose (2'FL), 3-fucosyllactose (3FL), 4-fucosyllactose (4FL), 6-fucosyllactose (6FL), difucosyllactose (diFL), lactodifucotetraose (LDFT), Lacto-N-fucopentaose I (LNFP I), Lacto-N-fucopentaose II (LNFP II), Lacto-N-fucopentaose III (LNFP III), lacto-N-fucopentaose V (LNFP V), lacto-N-fucopentaose VI (LNFP VI), lacto-N-neofucopentaose I, lacto-N-difucohexaose I (LDFH I), lacto-N-difucohexaose II (LDFH II), Monofucosyllacto-N-hexaose III (MFLNH III), Difucosyllacto-N-hexaose (DFLNHa), difucosyl-lacto-N-neohexaose, 3'-sialyl-3-fucosyllactose, disialomonofucosyllacto-N-neohexaose, monofucosylmonosialyllacto-N-octaose (sialyl Lea), sialyllacto-N-fucohexaose II, disialyllacto-N-fucopentaose II, monofucosyldisialyllacto-N-tetraose.

A "neutral oligosaccharide" as used herein and as generally understood in the state of the art is an oligosaccharide that has no negative charge originating from a carboxylic acid group. Examples of such neutral oligosaccharide comprise 2'-fucosyllactose (2'FL), 3-fucosyllactose (3FL), 2',3-difucosyllactose (diFL), lacto-N-triose II, lacto-N-tetraose, lacto-N-neotetraose, lacto-N-fucopentaose I, lacto-N-neofucopentaose I, lacto-N-fucopentaose II, lacto-N-fucopentaose III, lacto-N-fucopentaose V, lacto-N-fucopentaose VI, lacto-N-neofucopentaose V, lacto-N-difucohexaose I, lacto-N-difucohexaose II, 6'-galactosyllactose, 3'-galactosyllactose, lacto-N-hexaose, lacto-N-neohexaose, para-lacto-N-hexaose, para-lacto-N-neohexaose, difucosyl-lacto-N-hexaose and difucosyl-lacto-N-neohexaose.

A "neutral non-fucosylated oligosaccharide" as used herein and as generally understood in the state of the art is an oligosaccharide that has no negative charge originating from a carboxylic acid group and does not contain a fucose residue. Examples of such neutral non-fucosylated oligosaccharides comprise lacto-N-triose II, lacto-N-tetraose, lacto-N-neotetraose, 6'-galactosyllactose, 3'-galactosyllactose, lacto-N-hexaose, lacto-N-neohexaose, para-lacto-N-hexaose and para-lacto-N-neohexaose.

The terms "LNT II," "LNT-II," "LN3," "lacto-N-triose II," "lacto-N-triose II," "lacto-N-triose," "lacto-N-triose" or "GlcNAcβ1-3Galβ1-4Glc" as used in the disclosure, are used interchangeably.

The terms "LNT," "lacto-N-tetraose," "lacto-N-tetraose" or "Galβ1-3GlcNAcβ1-3Galβ1-4Glc" as used in the disclosure, are used interchangeably.

The terms "LNnT," "lacto-N-neotetraose," "lacto-N-neotetraose," "neo-LNT" or "Galβ1-4GlcNAcβ1-3Galβ1-4Glc" as used in the disclosure, are used interchangeably.

The terms "LNB" and "Lacto-N-biose" are used interchangeably and refer to the disaccharide Gal-b1,3-GlcNAc.

The terms "LacNAc" and "N-acetyllactosamine" are used interchangeably and refer to the disaccharide Gal-b1,4-GlcNAc.

A "galactosylation pathway" as used herein is a biochemical pathway consisting of the enzymes and their respective genes, galactose-1-epimerase, galactokinase, glucokinase, galactose-1-phosphate uridylyltransferase, UDP-glucose 4-epimerase, glucose-1-phosphate uridylyltransferase, and/or glucophosphomutase, combined with a galactosyltransferase leading to an alpha or beta bound galactose on the 2, 3, 4, and/or 6 hydroxyl group of an oligosaccharide.

An "N-acetylglucosamine carbohydrate pathway" as used herein is a biochemical pathway consisting of the enzymes and their respective genes, L-glutamine-D-fructose-6-phosphate aminotransferase, glucosamine-6-phosphate deaminase, phosphoglucosamine mutase, N-acetylglucosamine-6-phosphate deacetylase, glucosamine 6-phosphate N-acetyltransferase, N-acetylglucosamine-1-phosphate uridylyltransferase, glucosamine-1-phosphate acetyltransferase, and/or glucosamine-1-phosphate acetyltransferase, combined with a glycosyltransferase leading to an alpha or beta bound N-acetylglucosamine on the 3, 4, and/or 6 hydroxyl group of an oligosaccharide.

An "N-acetylgalactosaminylation pathway" as used herein is a biochemical pathway comprising at least one of the enzymes and their respective genes chosen from the list comprising L-glutamine-D-fructose-6-phosphate aminotransferase, phosphoglucosamine mutase, N-acetylglucosamine 1-phosphate uridylyltransferase, glucosamine-1-phosphate acetyltransferase, UDP-N-acetylglucosamine 4-epimerase, UDP-glucose 4-epimerase, N-acetylgalactosamine kinase and/or UDP-N-acetylgalactosamine pyrophosphorylase combined with a glycosyltransferase leading to a GalNAc-modified compound comprising a mono-, di- or oligosaccharide having an alpha or beta bound N-acetylgalactosamine on the mono-, di- or oligosaccharide.

A "mannosylation pathway" as used herein is a biochemical pathway comprising at least one of the enzymes and their respective genes chosen from the list comprising mannose-6-phosphate isomerase, phosphomannomutase and/or mannose-1-phosphate guanylyltransferase combined with a glycosyltransferase leading to a mannosylated compound comprising a mono-, di- or oligosaccharide having an alpha or beta bound mannose on the mono-, di- or oligosaccharide.

An "N-acetylmannosaminylation pathway" as used herein is a biochemical pathway comprising at least one of the enzymes and their respective genes chosen from the list comprising L-glutamine-D-fructose-6-phosphate aminotransferase, glucosamine-6-phosphate deaminase, phosphoglucosamine mutase, N-acetylglucosamine-6-phosphate deacetylase, glucosamine 6-phosphate N-acetyltransferase, N-acetylglucosamine-1-phosphate uridyltransferase, glucosamine-1-phosphate acetyltransferase, glucosamine-1-phosphate acetyltransferase, UDP-GlcNAc 2-epimerase and/or ManNAc kinase combined with a glycosyltransferase leading to a ManNAc-modified compound comprising a mono-, di- or oligosaccharide having an alpha or beta bound N-acetylmannosamine on the mono-, di- or oligosaccharide.

The terms "L-glutamine-D-fructose-6-phosphate aminotransferase," "glutamine-fructose-6-phosphate transaminase (isomerizing)," "hexosephosphate aminotransferase," "glucosamine-6-phosphate isomerase (glutamine-forming)," "glutamine-fructose-6-phosphate transaminase (isomerizing)," "D-fructose-6-phosphate amidotransferase," "fructose-6-phosphate aminotransferase," "glucosaminephosphate isomerase," "glucosamine 6-phosphate synthase," "GlcN6P synthase," "GFA," "glms," "glmS" and "glmS*54" are used interchangeably and refer to an enzyme that catalyzes the conversion of D-fructose-6-phosphate into D-glucosamine-6-phosphate using L-glutamine.

The terms "glucosamine-6-P deaminase," "glucosamine-6-phosphate deaminase," "GlcN6P deaminase," "glucosamine-6-phosphate isomerase," "glmD" and "nagB" are used interchangeably and refer to an enzyme that catalyzes the reversible isomerization-deamination of glucosamine-6-phosphate (GlcN6P) to form fructose-6-phosphate and an ammonium ion.

The terms "phosphoglucosamine mutase" and "glmM" are used interchangeably and refer to an enzyme that catalyzes the conversion of glucosamine-6-phosphate to glucosamine-1-phosphate. Phosphoglucosamine mutase can also catalyze the formation of glucose-6-P from glucose-1-P, although at a 1400-fold lower rate.

The terms "N-acetylglucosamine-6-P deacetylase," "N-acetylglucosamine-6-phosphate deacetylase" and "nagA" are used interchangeably and refer to an enzyme that catalyzes the hydrolysis of the N-acetyl group of N-acetylglucosamine-6-phosphate (GlcNAc-6-P) to yield glucosamine-6-phosphate (GlcN6P) and acetate.

An N-acylglucosamine 2-epimerase is an enzyme that catalyzes the reaction N-acyl-D-glucosamine=N-acyl-D-mannosamine. Alternative names for this enzyme comprise N-acetylglucosamine 2-epimerase, N-acetyl-D-glucosamine 2-epimerase, GlcNAc 2-epimerase, N-acyl-D-glucosamine 2-epimerase and N-acetylglucosamine epimerase.

An UDP-N-acetylglucosamine 2-epimerase is an enzyme that catalyzes the reaction N-acetyl-D-glucosamine=N-acetylmannosamine. Alternative names for this enzyme comprise UDP-N-acylglucosamine 2-epimerase, UDP-GlcNAc-2-epimerase and UDP-N-acetyl-D-glucosamine 2-epimerase.

An N-acetylmannosamine-6-phosphate 2-epimerase is an enzyme that catalyzes the reaction N-acetyl-D-glucosamine 6-phosphate=N-acetyl-D-mannosamine 6-phosphate.

A bifunctional UDP-GlcNAc 2-epimerase/kinase is a bifunctional enzyme that catalyzes the reaction UDP-N-acetyl-D-glucosamine=N-acetyl-D-mannosamine and the reaction N-acetyl-D-mannosamine+ATP=ADP+N-acetyl-D-mannosamine 6-phosphate.

A glucosamine 6-phosphate N-acetyltransferase is an enzyme that catalyzes the transfer of an acetyl group from acetyl-CoA to D-glucosamine-6-phosphate thereby generating a free CoA and N-acetyl-D-glucosamine 6-phosphate. Alternative names comprise aminodeoxyglucosephosphate acetyltransferase, D-glucosamine-6-P N-acetyltransferase, glucosamine 6-phosphate acetylase, glucosamine 6-phosphate N-acetyltransferase, glucosaminephosphate N-acetyltransferase, glucosamine-6-phosphate acetylase, N-acetylglucosamine-6-phosphate synthase, phosphoglucosamine acetylase, phosphoglucosamine N-acetylase phosphoglucosamine N-acetylase, phosphoglucosamine transacetylase, GNA and GNA1.

The term "N-acetylglucosamine-6-phosphate phosphatase" refers to an enzyme that dephosphorylates N-acetylglucosamine-6-phosphate (GlcNAc-6-P) hereby synthesizing N-acetylglucosamine (GlcNAc).

The term "N-acetylmannosamine-6-phosphate phosphatase" refers to an enzyme that dephosphorylates N-acetylmannosamine-6-phosphate (ManNAc-6P) to N-acetylmannosamine (ManNAc).

The terms "N-acetylmannosamine-6-phosphate 2-epimerase," "ManNAc-6-P isomerase," "ManNAc-6-P 2-epimerase," "N-acetylglucosamine-6P 2-epimerase" and "nanE" are used interchangeably and refer to an enzyme that converts ManNAc-6-P to N-acetylglucosamine-6-phosphate (GlcNAc-6-P).

The terms "phosphoacetylglucosamine mutase," "acetylglucosamine phosphomutase," "acetylaminodeoxyglucose phosphomutase," "phospho-N-acetylglucosamine mutase" and "N-acetyl-D-glucosamine 1,6-phosphomutase" are used interchangeably and refer to an enzyme that catalyzes the conversion of N-acetyl-glucosamine 1-phosphate into N-acetylglucosamine 6-phosphate.

The terms "N-acetylglucosamine 1-phosphate uridylyltransferase," "N-acetylglucosamine-1-phosphate uridyltransferase," "UDP-N-acetylglucosamine diphosphorylase," "UDP-N-acetylglucosamine pyrophosphorylase," "uridine diphosphoacetylglucosamine pyrophosphorylase," "UTP:2-acetamido-2-deoxy-alpha-D-glucose-1-phosphate uridylyltransferase," "UDP-GlcNAc pyrophosphorylase," "GlmU uridylyltransferase," "Acetylglucosamine 1-phosphate uridylyltransferase," "UDP-acetylglucosamine pyrophosphorylase," "uridine diphosphate-N-acetylglucosamine pyrophosphorylase," "uridine diphosphoacetylglucosamine phosphorylase," and "acetylglucosamine 1-phosphate uridylyltransferase" are used interchangeably and refer to an enzyme that catalyzes the conversion of N-acetylglucosamine 1-phosphate (GlcNAc-1-P) into UDP-N-acetylglucosamine (UDP-GlcNAc) by the transfer of uridine 5-monophosphate (from uridine 5-triphosphate (UTP)).

The term glucosamine-1-phosphate acetyltransferase refers to an enzyme that catalyzes the transfer of the acetyl group from acetyl coenzyme A to glucosamine-1-phosphate (GlcN-1-P) to produce N-acetylglucosamine-1-phosphate (GlcNAc-1-P).

The term "glmU" refers to a bifunctional enzyme that has both N-acetylglucosamine-1-phosphate uridyltransferase and glucosamine-1-phosphate acetyltransferase activity and that catalyzes two sequential reactions in the de novo biosynthetic pathway for UDP-GlcNAc. The C-terminal domain catalyzes the transfer of acetyl group from acetyl coenzyme A to GlcN-1-P to produce GlcNAc-1-P, which is converted into UDP-GlcNAc by the transfer of uridine 5-monophosphate, a reaction catalyzed by the N-terminal domain.

The terms "galactose-1-epimerase," "aldose 1-epimerase," "mutarotase," "aldose mutarotase," "galactose mutarotase," "galactose 1-epimerase" and "D-galactose 1-epimerase" are used interchangeably and refer to an enzyme that catalyzes the conversion of beta-D-galactose into alpha-D-galactose.

The terms "galactokinase," "galactokinase (phosphorylating)" and "ATP:D-galactose-1-phosphotransferase" are used interchangeably and refer to an enzyme that catalyzes the conversion of alpha-D-galactose into alpha-D-galactose 1-phosphate using ATP.

The terms glucokinase, and "glucokinase (phosphorylating)" are used interchangeably and refer to an enzyme that catalyzes the conversion of D-glucose into D-glucose 6-phosphate using ATP.

The terms "galactose-1-phosphate uridylyltransferase," "Gal-1-P uridylyltransferase," "UDP-glucose-hexose-1-phosphate uridylyltransferase," "uridyl transferase," "hexose-1-phosphate uridylyltransferase," "uridyltransferase"; "hexose 1-phosphate uridyltransferase," "UDP-glucose:alpha-D-galactose-1-phosphate uridylyltransferase," "galB" and "galT" are used interchangeably and refer to an enzyme that catalyzes the reaction D-galactose 1-phosphate+UDP-D-glucose=D-glucose 1-phosphate+UDP-D-galactose.

The terms "UDP-glucose 4-epimerase," "UDP-galactose 4-epimerase," "uridine diphosphoglucose epimerase," "galactowaldenase," "UDPG-4-epimerase," "uridine diphospho galactose 4-epimerase," "uridine diphosphogalactose-4-epimerase," "UDP-glucose epimerase," "4-epimerase," "uridine diphosphoglucose 4-epimerase," "uridine diphosphate glucose 4-epimerase" and "UDP-D-galactose 4-epimerase" are used interchangeably and refer to an enzyme that catalyzes the conversion of UDP-D-glucose into UDP-galactose.

The terms "glucose-1-phosphate uridylyltransferase," "UTP-glucose-1-phosphate uridylyltransferase," "UDP glucose pyrophosphorylase," "UDPG phosphorylase," "UDPG pyrophosphorylase," "uridine 5'-diphosphoglucose pyrophosphorylase," "uridine diphosphoglucose pyrophosphorylase," "uridine diphosphate-D-glucose pyrophosphorylase," "uridine-diphosphate glucose pyrophosphorylase" and "galU" are used interchangeably and refer to an enzyme that catalyzes the conversion of D-glucose-1-phosphate into UDP-glucose using UTP.

The terms "phosphoglucomutase (alpha-D-glucose-1,6-bisphosphate-dependent)," "glucose phosphomutase (ambiguous)" and "phosphoglucose mutase (ambiguous)" are used interchangeably and refer to an enzyme that catalyzes the conversion of D-glucose 1-phosphate into D-glucose 6-phosphate.

The terms "UDP-N-acetylglucosamine 4-epimerase," "UDP acetylglucosamine epimerase," "uridine diphosphoacetylglucosamine epimerase," "uridine diphosphate N-acetylglucosamine-4-epimerase," "uridine 5'-diphospho-N-acetylglucosamine-4-epimerase" and "UDP-N-acetyl-D-glucosamine 4-epimerase" are used interchangeably and refer to an enzyme that catalyzes the epimerization of UDP-N-acetylglucosamine (UDP-GlcNAc) to UDP-N-acetylgalactosamine (UDP-GalNAc).

The terms "N-acetylgalactosamine kinase," "GALK2," "GK2," "GalNAc kinase," "N-acetylgalactosamine (GalNAc)-1-phosphate kinase" and "ATP:N-acetyl-D-galactosamine 1-phosphotransferase" are used interchangeably and refer to an enzyme that catalyzes the synthesis of N-acetylgalactosamine 1-phosphate (GalNAc-1-P) from N-acetylgalactosamine (GalNAc) using ATP.

The terms "UDP-N-acetylgalactosamine pyrophosphorylase" and "UDP-GalNAc pyrophosphorylase" are used interchangeably and refer to an enzyme that catalyzes the conversion of N-acetylgalactosamine 1-phosphate (GalNAc-1-P) into UDP-N-acetylgalactosamine (UDP-GalNAc) using UTP.

The terms "N-acetylneuraminate kinase," "ManNAc kinase," "N-acetyl-D-mannosamine kinase" and "nanK" are used interchangeably and refer to an enzyme that phosphorylates ManNAc to synthesize N-acetylmannosamine-phosphate (ManNAc-6-P).

The terms "acetyl-coenzyme A synthetase," "acs," "acetyl-CoA synthetase," "AcCoA synthetase," "acetate-CoA ligase," "acyl-activating enzyme" and "yfaC" are used interchangeably and refer to an enzyme that catalyzes the conversion of acetate into acetyl-coenzyme A (AcCoA) in an ATP-dependent reaction.

The terms "pyruvate dehydrogenase," "pyruvate oxidase," "PDX," "poxB" and "pyruvate:ubiquinone-8 oxidoreductase" are used interchangeably and refer to an enzyme that catalyzes the oxidative decarboxylation of pyruvate to produce acetate and CO2.

The terms "lactate dehydrogenase," "D-lactate dehydrogenase," "ldhA," "hslI," "htpH," "D-LDH," "fermentative lactate dehydrogenase" and "D-specific 2-hydroxyacid dehydrogenase" are used interchangeably and refer to an enzyme that catalyzes the conversion of lactate into pyruvate hereby generating NADH.

As used herein, the term "cell productivity index (CPI)" refers to the mass of the product produced by the cells divided by the mass of the cells produced in the culture.

The term "purified" refers to material that is substantially or essentially free from components which interfere with the activity of the biological molecule. For cells, saccharides, nucleic acids, and polypeptides, the term "purified" refers to material that is substantially or essentially free from components which normally accompany the material as found in its native state. Typically, purified saccharides, oligosaccharides, proteins or nucleic acids of the disclosure are at least about 50%, 55%, 60%, 65%, 70%, 75%, 80% or 85% pure, usually at least about 90%, 91%, 92%, 93%, 94%, 95%, 96%, 97%, 98%, or 99% pure as measured by band intensity on a silver-stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized. For oligosaccharides, purity can be determined using methods such as but not limited to thin layer chromatography, gas chromatography, NMR, HPLC, capillary electrophoresis or mass spectroscopy.

The terms "identical" or "percent identity" or "% identity" in the context of two or more nucleic acid or polypeptide sequences, refer to two or more sequences or subsequences that are the same or have a specified percentage of amino acid residues or nucleotides that are the same, when compared and aligned for maximum correspondence, as measured using sequence comparison algorithms or by visual inspection. For sequence comparison, one sequence acts as a reference sequence, to which test sequences are compared. When using a sequence comparison algorithm, test and reference sequences are inputted into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Percent identity may be calculated globally over the full-length sequence of the reference sequence, resulting in a global percent identity score. Alternatively, percent identity may be calculated over a partial sequence of the reference sequence, resulting in a local percent identity score. Using the full-length of the reference sequence in a local sequence alignment results in a global percent identity score between the test and the reference sequence. Percent identity can be determined using different algorithms like for example BLAST and PSI-BLAST (Altschul et al., 1990, J. Mol. Biol. 215:3, 403-410; Altschul et al., 1997, Nucleic Acids Res. 25: 17, 3389-402), the Clustal Omega method (Sievers et al., 2011, Mol. Syst. Biol. 7:539), the MatGAT method (Campanella et al., 2003, BMC Bioinformatics, 4:29) or EMBOSS Needle.

The BLAST (Basic Local Alignment Search Tool)) method of alignment is an algorithm provided by the National Center for Biotechnology Information (NCBI) to compare sequences using default parameters. The program compares nucleotide or protein sequences to sequence databases and calculates the statistical significance. PSI-BLAST (Position-Specific Iterative Basic Local Alignment Search Tool) derives a position-specific scoring matrix (PSSM) or profile from the multiple sequence alignment of sequences detected above a given score threshold using protein—protein BLAST (BLASTp). The BLAST method can be used for pairwise or multiple sequence alignments. Pairwise Sequence Alignment is used to identify regions of similarity that may indicate functional, structural and/or evolutionary relationships between two biological sequences (protein or nucleic acid). The web interface for BLAST is available at the NCBI website.

Clustal Omega (Clustal W) is a multiple sequence alignment program that uses seeded guide trees and HMM profile-profile techniques to generate alignments between three or more sequences. It produces biologically meaningful multiple sequence alignments of divergent sequences. The web interface for Clustal W is available at the EMBL-EBI web site. Default parameters for multiple sequence alignments and calculation of percent identity of protein sequences using the Clustal W method are: enabling de-alignment of input sequences: FALSE; enabling mbed-like clustering guide-tree: TRUE; enabling mbed-like clustering iteration: TRUE; Number of (combined guide-tree/HMM) iterations: default(0); Max Guide Tree Iterations: default [−1]; Max HMM Iterations: default [−1]; order: aligned.

MatGAT (Matrix Global Alignment Tool) is a computer application that generates similarity/identity matrices for DNA or protein sequences without needing pre-alignment of the data. The program performs a series of pairwise alignments using the Myers and Miller global alignment algorithm, calculates similarity and identity, and then places the results in a distance matrix. The user may specify which type of alignment matrix (e.g., BLOSUM50, BLOSUM62, and PAM250) to employ with their protein sequence examination.

EMBOSS Needle uses the Needleman-Wunsch global alignment algorithm to find the optimal alignment (including gaps) of two sequences when considering their entire length. The optimal alignment is ensured by dynamic programming methods by exploring all possible alignments and choosing the best. The Needleman-Wunsch algorithm is a member of the class of algorithms that can calculate the best score and alignment in the order of mn steps, (where "n" and "m" are the lengths of the two sequences). The gap open penalty (default 10.0) is the score taken away when a gap is created. The default value assumes you are using the EBLOSUM62 matrix for protein sequences. The gap extension (default 0.5) penalty is added to the standard gap penalty for each base or residue in the gap. This is how long gaps are penalized.

As used herein, a polypeptide having an amino acid sequence having at least 80% sequence identity to the full-length sequence of a reference polypeptide sequence is to be understood as that the sequence has 80%, 81%, 82%, 83%, 84%, 85%, 86%, 87%, 88%, 89%, 90%, 91%, 91.50%, 92.00%, 92.50%, 93.00%, 93.50%, 94.00%, 94.50%, 95.00%, 95.50%, 96.00%, 96.50%, 97.00%, 97.50%, 98.00%, 98.50%, 99.00%, 99.50%, 99.60%, 99.70%, 99.80%, 99.90%, 100% sequence identity to the full-length of the amino acid sequence of the reference polypeptide sequence. Throughout the application, unless explicitly specified otherwise, a polypeptide (or DNA sequence) comprising/consisting/having an amino acid sequence (or nucleotide sequence) having at least 80% sequence identity to the full-length amino acid sequence (or nucleotide sequence) of a reference polypeptide (or nucleotide sequence), usually indicated with a SEQ ID NO or UniProt ID or Genbank No., preferably has at least 85%, 90%, 91%, 92%, 93%, 94%, 95%, 96%, 97%, 98% or 99%, more preferably has at least 85%, even more preferably has at least 90%, most preferably has at least 95%, sequence identity to the full length reference sequence.

For the purposes of this disclosure, percent identity is determined using MatGAT2.01 (Campanella et al., 2003, BMC Bioinformatics 4:29). The following default parameters for protein are employed: (1) Gap cost Existence: 12 and Extension: 2; (2) The Matrix employed was BLOSUM65. In a preferred embodiment, sequence identity is calculated based on the full-length sequence of a given SEQ ID NO, i.e., the reference sequence, or a part thereof. Part thereof preferably means at least 50%, 60%, 70%, 80%, 90% or 95% of the complete reference sequence.

The term "cultivation" refers to the culture medium wherein the cell is cultivated or fermented, the cell itself, and the oligosaccharides that are produced by the cell in whole broth, i.e., inside (intracellularly) as well as outside (extracellularly) of the cell.

The terms "membrane transporter proteins" or "membrane proteins" are used interchangeably and refer to proteins that are part of or interact with the cell membrane and control the flow of molecules and information across the cell. The membrane proteins are thus involved in transport, be it import into or export out of the cell.

Such membrane transporter proteins can be porters, P-P-bond-hydrolysis-driven transporters, (β-Barrel Porins, auxiliary transport proteins, putative transport proteins and phosphotransfer-driven group translocators as defined by the Transporter Classification Database that is operated and curated by the Saier Lab Bioinformatics Group available via at the Transporter Classification Database online and providing a functional and phylogenetic classification of membrane transport proteins This Transporter Classification Database details a comprehensive IUBMB approved classification system for membrane transporter proteins known as the Transporter Classification (TC) system. The TCDB classification searches as described here are defined as released on 17th June 2019.

Porters is the collective name of uniporters, symporters, and antiporters that utilize a carrier-mediated process (Saier et al., Nucleic Acids Res. 44 (2016) D372-D379). They belong to the electrochemical potential-driven transporters and are also known as secondary carrier-type facilitators. Membrane transporter proteins are included in this class when they utilize a carrier-mediated process to catalyze uniport when a single species is transported either by facilitated diffusion or in a membrane potential-dependent process if the solute is charged; antiport when two or more species are transported in opposite directions in a tightly coupled process, not coupled to a direct form of energy other than chemiosmotic energy; and/or symport when two or more species are transported together in the same direction in a tightly coupled process, not coupled to a direct form of energy other than chemiosmotic energy, of secondary carriers (Forrest et al., Biochim. Biophys. Acta 1807 (2011) 167-188). These systems are usually stereospecific. Solute: solute countertransport is a characteristic feature of secondary carriers. The dynamic association of porters and enzymes creates functional membrane transport metabolons that channel substrates typically obtained from the extracellular compartment directly into their cellular metabolism (Moraes and Reithmeier, Biochim. Biophys. Acta 1818 (2012), 2687-2706). Solutes that are transported via this porter system include but are not limited to cations, organic anions, inorganic anions, nucleosides, amino acids, polyols, phosphorylated glycolytic intermediates, osmolytes, siderophores.

Membrane transporter proteins are included in the class of P-P-bond hydrolysis-driven transporters if they hydrolyze the diphosphate bond of inorganic pyrophosphate, ATP, or another nucleoside triphosphate, to drive the active uptake and/or extrusion of a solute or solutes (Saier et al., Nucleic Acids Res. 44 (2016) D372-D379). The membrane transporter protein may or may not be transiently phosphorylated, but the substrate is not phosphorylated. Substrates that are transported via the class of P-P-bond hydrolysis-driven transporters include but are not limited to cations, heavy metals, beta-glucan, UDP-glucose, lipopolysaccharides, teichoic acid.

The β-Barrel porins membrane transporter proteins form transmembrane pores that usually allow the energy independent passage of solutes across a membrane. The transmembrane portions of these proteins consist exclusively of β-strands which form a β-barrel (Saier et al., Nucleic Acids Res. 44 (2016) D372-D379). These porin-type proteins are found in the outer membranes of Gram-negative bacteria, mitochondria, plastids, and possibly acid-fast Gram-positive bacteria. Solutes that are transported via these β-Barrel porins include but are not limited to nucleosides, raffinose, glucose, beta-glucosides, oligosaccharides.

The auxiliary transport proteins are defined to be proteins that facilitate transport across one or more biological membranes but do not themselves participate directly in transport. These membrane transporter proteins always function in conjunction with one or more established transport systems such as but not limited to outer membrane factors (OMFs), polysaccharide (PST) porters, the ATP-binding cassette (ABC)-type transporters. They may provide a function connected with energy coupling to transport, play a structural role in complex formation, serve a biogenic or stability function or function in regulation (Saier et al., Nucleic Acids Res. 44 (2016) D372-D379). Examples of auxiliary transport proteins include but are not limited to the polysaccharide copolymerase family involved in polysaccharide transport, the membrane fusion protein family involved in bacteriocin and chemical toxin transport.

Putative transport protein comprises families which will either be classified elsewhere when the transport function of a member becomes established or will be eliminated from the Transporter Classification system if the proposed transport function is disproven. These families include a member or members for which a transport function has been suggested, but evidence for such a function is not yet compelling (Saier et al., Nucleic Acids Res. 44 (2016) D372-D379). Examples of putative transporters classified in this group under the TCDB system as released on 17 Jun. 2019 include but are not limited to copper transporters.

The phosphotransfer-driven group translocators are also known as the PEP-dependent phosphoryl transfer-driven group translocators of the bacterial phosphoenolpyruvate: sugar phosphotransferase system (PTS). The product of the reaction, derived from extracellular sugar, is a cytoplasmic sugar-phosphate. The enzymatic constituents, catalyzing sugar phosphorylation, are superimposed on the transport process in a tightly coupled process. The PTS system is involved in many different aspects comprising in regulation and chemotaxis, biofilm formation, and pathogenesis (Lengeler, J. Mol. Microbiol. Biotechnol. 25 (2015) 79-93; Saier, J. Mol. Microbiol. Biotechnol. 25 (2015) 73-78). Membrane transporter protein families classified within the phosphotransfer-driven group translocators under the TCDB system as released on 17 Jun. 2019 include PTS systems linked to transport of glucose-glucosides, fructose-mannitol, lactose-N,N'-diacetylchitobiose-beta-glucoside, glucitol, galactitol, mannose-fructose-sorbose and ascorbate.

The major facilitator superfamily (MFS) is a superfamily of membrane transporter proteins catalyzing uniport, solute: cation (H+, but seldom Na+) symport and/or solute:H+ or solute:solute antiport. Most are of 400-600 amino acyl residues in length and possess either 12, 14, or occasionally, 24 transmembrane α-helical spanners (TMSs) as defined by the Transporter Classification Database operated by the Saier Lab Bioinformatics Group.

"SET" or "Sugar Efflux Transporter" as used herein refers to membrane proteins of the SET family which are proteins with InterPRO domain IPR004750 and/or are proteins that belong to the eggNOGv4.5 family ENOG410XTE9. Identification of the InterPro domain can be done by using the online tool or a standalone version of InterProScan using the default values. Identification of the orthology family in eggNOGv4.5 can be done using the online version or a standalone version of eggNOG-mappervl.

The term "Siderophore" as used herein is referring to the secondary metabolite of various microorganisms which are mainly ferric ion specific chelators. These molecules have been classified as catecholate, hydroxamate, carboxylate and mixed types. Siderophores are in general synthesized by a nonribosomal peptide synthetase (NRPS) dependent pathway or an NRPS independent pathway (NIS). The most important precursor in NRPS-dependent siderophore biosynthetic pathway is chorismate. 2, 3-DHBA could be formed from chorismate by a three-step reaction catalyzed by isochorismate synthase, isochorismatase, and 2, 3-dihydroxybenzoate-2, 3-dehydrogenase. Siderophores can also be formed from salicylate which is formed from isochorismate by isochorismate pyruvate lyase. When ornithine is used as precursor for siderophores, biosynthesis depends on the hydroxylation of ornithine catalyzed by L-ornithine N5-monooxygenase. In the NIS pathway, an important step in siderophore biosynthesis is N(6)-hydroxylysine synthase.

A transporter is needed to export the siderophore outside the cell. Four superfamilies of membrane proteins are identified so far in this process: the major facilitator superfamily (MFS); the Multidrug/Oligosaccharidyl-lipid/Polysaccharide Flippase Superfamily (MOP); the resistance, nodulation and cell division superfamily (RND); and the ABC superfamily. In general, the genes involved in siderophore export are clustered together with the siderophore biosynthesis genes. The term "siderophore exporter" as used herein refers to such transporters needed to export the siderophore outside of the cell.

The ATP-binding cassette (ABC) superfamily contains both uptake and efflux transport systems, and the members of these two groups generally cluster loosely together. ATP hydrolysis without protein phosphorylation energizes transport. There are dozens of families within the ABC superfamily, and family generally correlates with substrate specificity. Members are classified according to class 3.A.1 as defined by the Transporter Classification Database operated by the Saier Lab Bioinformatics Group available at the Transporter Classification Database online and providing a functional and phylogenetic classification of membrane transporter proteins.

The term "enabled efflux" means to introduce the activity of transport of a solute over the cytoplasm membrane and/or the cell wall. The transport may be enabled by introducing and/or increasing the expression of a transporter protein as described in the disclosure. The term "enhanced efflux" means to improve the activity of transport of a solute over the cytoplasm membrane and/or the cell wall. Transport of a solute over the cytoplasm membrane and/or cell wall may be enhanced by introducing and/or increasing the expression of a membrane transporter protein as described in the disclosure. "Expression" of a membrane transporter protein is defined as "overexpression" of the gene encoding the membrane transporter protein in the case the gene is an endogenous gene or "expression" in the case the gene encoding the membrane transporter protein is a heterologous gene that is not present in the wild type strain or cell.

The terms "precursor" as used herein refers to substances which are taken up or synthetized by the cell for the specific production of a neutral non-fucosylated oligosaccharide according to the disclosure. In this sense a precursor can be an acceptor as defined herein, but can also be another substance, metabolite, which is first modified within the cell as part of the biochemical synthesis route of the oligosaccharide. Examples of such precursors comprise the acceptors as defined herein, and/or glucose, galactose, fructose, glycerol, mannose, maltose, sucrose, lactose, dihydroxyacetone, glucosamine, N-acetyl-glucosamine, N-acetyl-mannosamine, phosphorylated sugars like, e.g., but not limited to glucose-1-phosphate, galactose-1-phosphate, glucose-6-phosphate, fructose-6-phosphate, fructose-1,6-bisphosphate, glycerol-3-phosphate, glyceraldehyde-3-phosphate, dihydroxyacetone-phosphate, glucosamine-6-phosphate, N-acetyl-glucosamine-6-phosphate, N-acetylmannosamine-6-phosphate, N-acetylglucosamine-1-phosphate, mannose-6-phosphate, mannose-1-phosphate, and/or nucleotide-activated sugars as defined herein like, e.g., UDP-glucose, UDP-galactose, UDP-N-acetylglucosamine, GDP-mannose and/or GDP-4-dehydro-6-deoxy-α-D-mannose.

Optionally, the cell is transformed to comprise at least one nucleic acid sequence encoding a protein selected from the group consisting of lactose transporter, transporter for a nucleotide-activated sugar wherein the transporter internalizes a to the medium added precursor for neutral non-fucosylated oligosaccharide synthesis.

The term "acceptor" as used herein refers to di- or oligosaccharides which can be modified by a glycosyltransferase. Examples of such acceptors comprise lactose, lacto-N-biose (LNB), lacto-N-triose, lacto-N-tetraose (LNT), lacto-N-neotetraose (LNnT), N-acetyl-lactosamine (LacNAc), lacto-N-pentaose (LNP), lacto-N-neopentaose, para lacto-N-pentaose, para lacto-N-neopentaose, lacto-N-novopentaose I, lacto-N-hexaose (LNH), lacto-N-neohexaose (LNnH), para lacto-N-neohexaose (pLNnH), para lacto-N-hexaose (pLNH), lacto-N-heptaose, lacto-N-neoheptaose, para lacto-N-neoheptaose, para lacto-N-heptaose, lacto-N-octaose (LNO), lacto-N-neooctaose, iso lacto-N-octaose, para lacto-N-octaose, iso lacto-N-neooctaose, novo lacto-N-neooctaose, para lacto-N-neooctaose, iso lacto-N-nonaose, novo lacto-N-nonaose, lacto-N-nonaose, lacto-N-decaose, iso lacto-N-decaose, novo lacto-N-decaose, lacto-N-neodecaose, galactosyllactose, a lactose extended with 1, 2, 3, 4, 5, or a multiple of N-acetyllactosamine units and/or 1, 2, 3, 4, 5, or a multiple of, Lacto-N-biose units, and oligosaccharide containing 1 or multiple N-acetyllactosamine units and or 1 or multiple lacto-N-biose units or an intermediate into oligosaccharide versions thereof.

Throughout the application, unless explicitly stated otherwise, the features "synthesize," "synthesized" and "synthesis" are interchangeably used with the features "produce," "produced" and "production," respectively.

According to a first aspect, the disclosure provides a metabolically engineered cell for the production of a mixture comprising at least four different neutral non-fucosylated oligosaccharides, i.e., a cell which is metabolically engineered for the production of a mixture comprising at least four different neutral non-fucosylated oligosaccharides. Herein, a single metabolically engineered cell is provided which is capable to express, preferably expresses, at least two glycosyltransferases and is capable of synthesizing one or more sugar-nucleotide(s) which is/are donor(s) for the glycosyltransferases. Throughout the application, unless explicitly stated otherwise, a "genetically modified cell" or "metabolically engineered cell" preferably means a cell which is genetically modified or metabolically engineered, respectively, for the production of the mixture comprising at least four different neutral non-fucosylated oligosaccharides according to the disclosure. In the context of the disclosure, the at least four different neutral non-fucosylated oligosaccharides of the mixture as disclosed herein preferably do not occur in the wild type progenitor of the metabolically engineered cell.

According to second aspect, the disclosure provides a method for the production of a mixture comprising at least four different neutral non-fucosylated oligosaccharides. The method comprises the steps of:
  i) providing a cell, preferably a single cell, that is capable of expressing, preferably expresses, at least two glycosyltransferases and is capable to synthesize one or more nucleotide-sugar(s), wherein the nucleotide-sugar(s) is/are donor(s) for the glycosyltransferases, and
  ii) cultivating the cell under conditions permissive to express the glycosyltransferases and to synthesize the nucleotide-sugar(s),
  iii) preferably, separating at least one of the neutral non-fucosylated oligosaccharides from the cultivation, more preferably separating all of the oligosaccharides from the cultivation.

In the scope of the disclosure, permissive conditions are understood to be conditions relating to physical or chemical parameters including but not limited to temperature, pH, pressure, osmotic pressure and product/precursor/acceptor concentration.

In a particular embodiment, the permissive conditions may include a temperature-range of 30+/−20 degrees centigrade, a pH-range of 7+/−3.

In the context of the disclosure, it should be understood that the cell produces the oligosaccharides intracellularly. The skilled person will further understand that a fraction or substantially all of the produced oligosaccharides remains intracellularly and/or is excreted outside the cell via passive or active transport.

According to the disclosure, the method for the production of a mixture comprising at least four different neutral non-fucosylated oligosaccharides can make use of a non-metabolically engineered cell or can make use of a metabolically engineered cell, i.e., a cell which is metabolically engineered for the production of the mixture comprising at least four different neutral non-fucosylated oligosaccharides.

According to a preferred embodiment of the method and cell according to the disclosure, the metabolically engineered cell is modified with gene expression modules wherein the expression from any one of the expression modules is constitutive or is created by a natural inducer.

The expression modules are also known as transcriptional units and comprise polynucleotides for expression of recombinant genes including coding gene sequences and appropriate transcriptional and/or translational control signals that are operably linked to the coding genes. The control signals comprise promoter sequences, untranslated regions, ribosome binding sites, terminator sequences. The expression modules can contain elements for expression of one single recombinant gene but can also contain elements for expression of more recombinant genes or can be organized in an operon structure for integrated expression of two or more recombinant genes. The polynucleotides may be produced by recombinant DNA technology using techniques well-known in the art. Methods which are well known to those skilled in the art to construct expression modules include, for example, in vitro recombinant DNA techniques, synthetic techniques, and in vivo genetic recombination. See, for example, the techniques described in Sambrook et al. (2001) Molecular Cloning: a laboratory manual, 3rd Edition, Cold Spring Harbor Laboratory Press, CSH, New York or to Current Protocols in Molecular Biology, John Wiley and Sons, N.Y. (1989 and yearly updates).

According to a preferred embodiment of the disclosure, the cell is modified with one or more expression modules. The expression modules can be integrated in the genome of the cell or can be presented to the cell on a vector. The vector can be present in the form of a plasmid, cosmid, phage, liposome, or virus, which is to be stably transformed/transfected into the metabolically engineered cell. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. These vectors may contain selection markers such as but not limited to antibiotic markers, auxotrophic markers, toxin-antitoxin markers, RNA sense/antisense markers. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., see above. For recombinant production, cells can be genetically engineered to incorporate expression systems or portions thereof or polynucleotides of the disclosure. Introduction of a polynucleotide into the cell can be effected by methods described in many standard laboratory manuals, such as Davis et al., Basic Methods in Molecular Biology, (1986), and Sambrook et al., 1989, supra.

As used herein an expression module comprises polynucleotides for expression of at least one recombinant gene. The recombinant gene is involved in the expression of a polypeptide acting in the synthesis of the neutral non-fucosylated oligosaccharide mixture; or the recombinant gene is linked to other pathways in the host cell that are not involved in the synthesis of the mixture of three or more neutral non-fucosylated oligosaccharides. The recombinant genes encode endogenous proteins with a modified expression or activity, preferably, the endogenous proteins are overexpressed; or the recombinant genes encode heterologous proteins that are heterogeneously introduced and expressed in the modified cell, preferably overexpressed. The endogenous proteins can have a modified expression in the cell which also expresses a heterologous protein.

According to a preferred embodiment of the disclosure, the expression of each of the expression modules is constitutive or created by a natural inducer. As used herein, constitutive expression should be understood as expression of a gene that is transcribed continuously in an organism. Expression that is created by a natural inducer should be understood as a facultative or regulatory expression of a gene that is only expressed upon a certain natural condition of the host (e.g., organism being in labor, or during lactation), as a response to an environmental change (e.g., including but not limited to hormone, heat, cold, light, oxidative or osmotic stress/signaling), or dependent on the position of the developmental stage or the cell cycle of the host cell including but not limited to apoptosis and autophagy.

The disclosure provides different types of cells for the production of an oligosaccharide mixture comprising four or more neutral non-fucosylated oligosaccharides with a single metabolically engineered cell. For example, the disclosure provides a cell wherein the cell expresses two different glycosyltransferases and the cell synthesizes one single nucleotide-sugar which is donor for both the expressed glycosyltransferases. The disclosure also provides a cell wherein the cell expresses three different glycosyltransferases and the cell synthesizes one single nucleotide-sugar which is donor for all of the three expressed glycosyltransferases. The disclosure also provides a cell wherein the cell expresses two different glycosyltransferases and the cell synthesizes two different nucleotide-sugars whereby a first nucleotide-sugar is donor for the first glycosyltransferase and a second nucleotide-sugar is donor for the second glycosyltransferase. The disclosure also provides a cell wherein the cell expresses three or more glycosyltransferases and the cell synthesizes one or more different nucleotide-sugar(s) which is/are donor(s) for all of the expressed glycosyltransferases.

In the method and cell described herein, the cell preferably comprises multiple copies of the same coding DNA sequence encoding for one protein. In the context of the disclosure, the protein can be a glycosyltransferase, a membrane protein or any other protein as disclosed herein. Throughout the application, the feature "multiple" means at least 2, preferably at least 3, more preferably at least 4, even more preferably at least 5.

In an embodiment of the method and/or cell according to the disclosure, the mixture comprises at least four, preferably at least five, more preferably at least six, even more preferably at least seven, most preferably at least eight, at least nine, at least ten different neutral non-fucosylated oligosaccharides. Neutral oligosaccharides are oligosaccharide structures that do not contain a negatively charged monosaccharide subunit including N-acetylneuraminic acid (Neu5Ac), commonly known as sialic acid, N-glycolylneuraminic acid (Neu5Gc), glucuronate and galacturonate. Neutral oligosaccharides are also referred to as non-acidic oligosaccharides. Sialic acid belongs to the family of derivatives of neuraminic acid (5-amino-3,5-dideoxy-D-glycero-D-galacto-non-2-ulosonic acid). Neu5Gc is a derivative of sialic acid, which is formed by hydroxylation of the N-acetyl group at C5 of Neu5Ac. Neutral oligosaccharides are non-sialylated oligosaccharides, and thus do not contain an acidic monosaccharide subunit. Neutral non-fucosylated oligosaccharides are non-charged non-fucosylated oligosaccharides that lack any fucose subunit. Throughout the application, unless otherwise stated, the features "oligosaccharide" and "oligosaccharides" are preferably replaced with "MMO" and "MMOs," respectively, more preferably replaced with "lactose-based MMO" and "lactose-based MMOs," respectively, even more preferably replaced with "HMO" and "HMOs," respectively.

In another embodiment of the method and/or cell according to the disclosure, at least one of the neutral non-fucosylated oligosaccharides in the mixture is a mammalian milk oligosaccharide (MMO), preferably lactose-based mammalian milk oligosaccharide, more preferably human milk oligosaccharide (HMO). In an embodiment, the cell produces one mammalian milk oligosaccharide in the produced mixture of at least four different neutral non-fucosylated oligosaccharides. In a preferred embodiment, the cell produces more than one mammalian milk oligosaccharide in the produced mixture of at least four different neutral non-fucosylated oligosaccharides. In a more preferred embodiment, all of the oligosaccharides in the produced mixture of at least four different neutral non-fucosylated oligosaccharides are mammalian milk oligosaccharides.

In the context of the disclosure, the mixture of at least four different neutral non-fucosylated oligosaccharides according to the disclosure can comprise lactose-based neutral non-fucosylated oligosaccharides, LNB-based neutral non-fucosylated oligosaccharides and/or LacNAc-based neutral non-fucosylated oligosaccharides as described herein.

In another more preferred embodiment of the method and/or cell according to the disclosure, the mixture comprises at least four, preferably at least five, more preferably at least six, even more preferably at least seven, most preferably at least eight, at least nine, at least ten neutral non-fucosylated mammalian milk oligosaccharides (MMOs), preferably lactose-based mammalian milk oligosaccharides, more preferably human milk oligosaccharides (HMOs). Throughout the application, unless explicitly stated otherwise, the feature "mixture comprising at least four different neutral non-fucosylated oligosaccharides" is preferably replaced with "mixture comprising at least four different neutral non-fucosylated MMOs, preferably lactose-based MMOs, more preferably HMOs," likewise it is preferred to replace "mixture comprising at least five different neutral non-fucosylated oligosaccharides" with "mixture comprising at least five different neutral non-fucosylated MMOs, preferably lactose-based MMOs, more preferably HMOs" etc. In the context of the disclosure, the mixture of at least four different neutral non-fucosylated mammalian milk oligosaccharides according to a preferred embodiment of the disclosure can comprise further oligosaccharides such as mammalian milk oligosaccharides and/or non-mammalian milk oligosaccharides. Such oligosaccharides can for example be lactose-based oligosaccharides, LNB-based oligosaccharides and/or LacNAc-based oligosaccharides as described herein. In an alternative and/or additional preferred embodiment of the method and/or cell according to the disclosure, mammalian milk oligosaccharides constitute at least 50%, preferably at least 60%, more preferably at least 70%, even more preferably at least 80%, even more preferably at least 90%, of the oligosaccharide mixture according to the disclosure. In a more preferred embodiment of the method and/or cell according to the disclosure, all the oligosaccharides in the mixture are MMOs, preferably lactose-based MMOs, more preferably HMOs. As already stated herein, it is preferred that the mixture as disclosed herein is the direct result of metabolically engineering a cell as described herein.

Throughout the application, unless explicitly stated otherwise, the feature "at least one" is preferably replaced with "one," likewise the feature "at least two" is preferably replaced with "two," etc.

In an optional embodiment of the method and/or cell according to the disclosure, the mixture according to the disclosure further comprises LacDiNAc (i.e., GalNAc-b1,4-GlcNAc) and/or GalNAc-b1,4-glucose.

In an additional and/or alternative embodiment of the method and/or cell according to the disclosure, the oligosaccharide mixture comprises at least three different neutral non-fucosylated oligosaccharides differing in degree of polymerization (DP). The degree of polymerization of an oligosaccharide refers to the number of monosaccharide units present in the oligosaccharide structure. As used herein, the degree of polymerization of an oligosaccharide is three (DP3) or more, the latter comprising any one of 4 (DP4), 5 (DP5), 6 (DP6) or longer. The oligosaccharide mixture as described herein preferably comprise at least four different neutral non-fucosylated oligosaccharides wherein at least three, preferably all oligosaccharides present in the mixture have a different degree of polymerization from each other. For example, the oligosaccharide mixture consists of four neutral non-fucosylated oligosaccharides, wherein two oligosaccharides are trisaccharides with a degree of polymerization of 3 (DP3), the third oligosaccharide is a tetrasaccharide with a degree of polymerization of 4 (DP4) and the fourth oligosaccharide is a pentasaccharide with a degree of polymerization of 5 (DP5). In another example, the oligosaccharide mixture consists of four neutral non-fucosylated oligosaccharides, wherein the first oligosaccharide is a trisaccharide with a degree of polymerization of 3 (DP3), the second and the third oligosaccharide are tetrasaccharides with a degree of polymerization of 4 (DP4) and the fourth oligosaccharide is a pentasaccharide with a degree of polymerization of 5 (DP5). In another example, the oligosaccharide mixture consists of four neutral non-fucosylated oligosaccharides, wherein the first oligosaccharide is a trisaccharide with a degree of polymerization of 3 (DP3), the second oligosaccharide is a tetrasaccharide with a degree of polymerization of 4 (DP4) and the third and fourth oligosaccharide are pentasaccharides with a degree of polymerization of 5 (DP5). In another example, the oligosaccharide mixture consists of four neutral non-fucosylated oligosaccharides wherein all the four oligosaccharides have a different degree of polymerization, with the first oligosaccharide being a trisaccharide having a degree of polymerization of 3 (DP3), with the second oligosaccharide being a tetrasaccharide having a degree of polymerization of 4 (DP4), with the third oligosaccharide being a pentasaccharide having a degree of polymerization of 5 (DP5), and with the fourth oligosaccharide being a hexasaccharide having a degree of polymerization of 6 (DP6). According to one embodiment of the method and/or cell of the disclosure, the cell produces a mixture comprising five different neutral non-fucosylated oligosaccharides or more than five different neutral non-fucosylated oligosaccharides. In one embodiment, such mixture comprises at least five different oligosaccharides wherein three of the oligosaccharides have a different degree of polymerization. In one embodiment, all of the oligosaccharides in the mixture have a different degree of polymerization as described herein.

According to an additional and/or alternative embodiment of the method and/or cell of the disclosure, at least one of the neutral non-fucosylated oligosaccharides of the mixture is galactosylated, glucosylated, xylosylated, mannosylated, contains an N-acetylglucosamine, contains an N-acetylgalactosamine, contains a rhamnose and/or contains an N-acetylmannosamine.

Preferably, the mixture of neutral non-fucosylated oligosaccharides comprises at least one oligosaccharide of 3 or more monosaccharide subunits linked to each other via glycosidic bonds, wherein at least one of the monosaccharide residues is a GlcNAc residue. The oligosaccharide can contain more than one GlcNAc residue, e.g., two, three or more. GlcNAc can be present at the reducing end of the oligosaccharide. The GlcNAc can also be present at the non-reducing end of the oligosaccharide. The GlcNAc can also be present within the oligosaccharide structure. GlcNAc can be linked to other monosaccharide subunits like, e.g., galactose.

Alternatively or additionally, the neutral non-fucosylated oligosaccharide mixture comprises at least one galactosylated oligosaccharide and contains at least one galactose monosaccharide subunit. The galactosylated oligosaccharide is a saccharide structure comprising at least three monosaccharide subunits linked to each other via glycosidic bonds, wherein at least one of the monosaccharide subunit is a galactose. The galactosylated oligosaccharide can contain more than one galactose residue, e.g., two, three or more. Galactose can be linked to other monosaccharide subunits comprising glucose and GlcNAc.

In an additional and/or alternative embodiment of the method and/or cell according to the disclosure, the relative abundance of each oligosaccharide in the mixture as described herein is at least 5%, preferably at least 10%.

In the context of this disclosure, the oligosaccharide mixture as disclosed herein is preferably the direct result of metabolically engineering a cell as described herein. This means that preferably at least one, more preferably at least two, even more preferably at least three, most preferably all, of the oligosaccharides in the mixture according to the disclosure are not produced by the wild type progenitor of the metabolically engineered cell.

The names of the oligosaccharides as described herein are in accordance with the oligosaccharide names and formulae as published by Urashima et al. (Trends in Glycoscience and Glycotechnology, 2018, vol. 30, no. 72, pages SE51-SE65) and references therein and as published in "Prebiotics and Probiotics in human milk. Origins and Functions of Milk-Borne Oligosaccharides and Bacteria," Chapters 2 & 3, Eds M. McGuire, M. McGuire, L. Bode, Elsevier, Academic Press, page 506).

In a more preferred embodiment of the method and/or cell according to the disclosure, the mixture comprises, consists essentially of or consists of at least four, preferably at least five, even more preferably at least six, even more preferably at least seven, most preferably at least eight, at least nine, at least ten, different neutral non-fucosylated oligosaccharides preferably selected from:

lactose-based neutral non-fucosylated oligosaccharides, preferably any one of Lacto-N-triose II (LN3), Lacto-N-neotetraose (LNnT), Lacto-N-tetraose (LNT), para-Lacto-N-neopentaose, para-Lacto-N-pentaose, para-Lacto-N-neohexaose, para-Lacto-N-hexaose, beta-(1,3)Galactosyl-para-Lacto-N-neopentaose, beta-(1,4) Galactosyl-para-Lacto-N-pentaose, Gal-a1,4-Gal-b1,4-Glc (Gal-a1,4-lactose), β3'-galactosyllactose, β6'-galactosyllactose, Gal-a1,4-Gal-a1,4-Gal-b1,4-Glc, Gal-a1,4-Gal-a1,4-Gal-a1,4-Gal-b1,4-Glc, Gal-b1,3-Galb1,3-Gal-b1,4-Glc, Gal-b1,3-Gal-b1,3-Galb1,3-Gal-b1,4-Glc, Gal-b1,3-Gal-b1,3-Gal-b1,3-Galb1,3-Gal-b1,4-Glc, Gal-b1,3-Gal-b1,3-Gal-b1,3-Gal-b1,3-Galb1,3-Gal-b1,4-Glc, GalNAc-b1,3-Gal-b1,4-Glc (GalNAc-b1,3-Lactose), Gal-b1,3-GalNAc-b1,3-lactose, GalNAc-b1,3-Gal-a1,4-Gal-b1,4-Glc (globo-N-tetraose), Gal-b1,3-GalNAc-b1,3-Gal-a1,4-Gal-b1,4-Glc, GalNAc-b1,3-LNT, Gal-b1,3-GalNAc-b1,3-LNT, novo-LNT (GlcNAc-b1,6-[Gal-b1,3]-Gal-b1,4-Glc), Gal-novo-LNP I (Gal-b1,4-GlcNAc-b1,6-[Gal-b1,3-Gal-b1,3]-Gal-b1,4-Glc), Gal-novo-LNP II (Gal-b1,4-GlcNAc-b1,6-[Gal-b1,3]-Gal-b1,3-Gal-b1,4-Glc), Gal-novo-LNP III (Gal-b1,3-Gal-b1,4-GlcNAc-b1,6-[Gal-b1,3]-Gal-b1,4-Glc), novo-LNO, GalNAc-b1,3-LNnT, Gal-b1,3-GalNAc-b1,3-LNnT, LNH, LNnH, iso-LNO, novo-LNO, novo-LNnO, LND, iso-LND, GalNAc-a1,3-Gal-b1,4-Glc, novo-LNP I, iso-LNT, DGalLNnH, galilipentasaccharide, more preferably any one of Lacto-N-triose II (LN3), Lacto-N-neotetraose (LNnT), Lacto-N-tetraose (LNT), para-Lacto-N-neopentaose, para-Lacto-N-pentaose, para-Lacto-N-neohexaose, para-Lacto-N-hexaose, beta-(1,3)Galactosyl-para-Lacto-N-neopentaose, beta-(1,4)Galactosyl-para-Lacto-N-pentaose, Gal-a1,4-Gal-b1,4-Glc (Gal-a1,4-lactose), β3'-galactosyllactose, β6'-galactosyllactose, GalNAc-b1,3-Lactose, globo-N-tetraose, most preferably any one of Lacto-N-triose II (LN3), Lacto-N-neotetraose (LNnT), Lacto-N-tetraose (LNT), para-Lacto-N-neopentaose, para-Lacto-N-pentaose, para-Lacto-N-neohexaose, para-Lacto-N-hexaose; and/or LNB-based neutral non-fucosylated oligosaccharides; and/or LacNAc-based neutral non-fucosylated oligosaccharides, like, e.g., LacDiNAc and poly-LacNAc.

Preferred mixtures in this context of the disclosure comprise mixtures that comprise, consist of or consist essentially of at least four, preferably at least five, even more preferably at least six, even more preferably at least seven, most preferably at least eight, at least nine, at least ten, different neutral non-fucosylated oligosaccharides chosen from the list comprising Lacto-N-triose II (LN3), Lacto-N-neotetraose (LNnT), Lacto-N-tetraose (LNT), para-Lacto-N-neopentaose, para-Lacto-N-pentaose, para-Lacto-N-neohexaose, para-Lacto-N-hexaose, beta-(1,3)Galactosyl-para-Lacto-N-neopentaose, beta-(1,4)Galactosyl-para-Lacto-N-pentaose, Gal-a1,4-Gal-b1,4-Glc (Gal-a1,4-lactose), β3'-galactosyllactose, β6'-galactosyllactose, Gal-a1,4-Gal-a1,4-Gal-b1,4-Glc, Gal-a1,4-Gal-a1,4-Gal-a1,4-Gal-b1,4-Glc, Gal-b1,3-Galb1,3-Gal-b1,4-Glc, Gal-b1,3-Gal-b1,3-Galb1,3-Gal-b1,4-Glc, Gal-b1,3-Gal-b1,3-Gal-b1,3-Galb1,3-Gal-b1,4-Glc, Gal-b1,3-Gal-b1,3-Gal-b1,3-Gal-b1,3-Galb1,3-Gal-b1,4-Glc, GalNAc-b1,3-Gal-b1,4-Glc (GalNAc-b1,3-Lactose), Gal-b1,3-GalNAc-b1,3-lactose, GalNAc-b1,3-Gal-a1,4-Gal-b1,4-Glc (globo-N-tetraose), Gal-b1,3-GalNAc-b1,3-Gal-a1,4-Gal-b1,4-Glc, GalNAc-b1,3-LNT, Gal-b1,3-GalNAc-b1,3-LNT, novo-LNT (GlcNAc-b1,6-[Gal-b1,3]-Gal-b1,4-Glc), Gal-novo-LNP I (Gal-b1,4-GlcNAc-b1,6-[Gal-b1,3-Gal-b1,3]-Gal-b1,4-Glc), Gal-novo-LNP II (Gal-b1,4-GlcNAc-b1,6-[Gal-b1,3]-Gal-b1,3-Gal-b1,4-Glc), Gal-novo-LNP III (Gal-b1,3-Gal-b1,4-GlcNAc-b1,6-[Gal-b1,3]-Gal-b1,4-Glc), novo-LNO, GalNAc-b1,3-LNnT, Gal-b1,3-GalNAc-b1,3-LNnT, LNH, LNnH, iso-LNO, novo-LNO, novo-LNnO, LND, iso-LND, GalNAc-a1,3-Gal-b1,4-Glc, novo-LNP I, iso-LNT, DGalLNnH, galilipentasaccharide, LacDiNAc and poly-LacNAc.

More preferred mixtures in this context of the disclosure comprise mixtures that comprise, consist of or consist essentially of at least four, preferably at least five, even more preferably at least six, even more preferably at least seven, most preferably at least eight, at least nine, at least ten, different neutral non-fucosylated oligosaccharides chosen from the list comprising Lacto-N-triose II (LN3), Lacto-N-neotetraose (LNnT), Lacto-N-tetraose (LNT), para-Lacto-N-neopentaose, para-Lacto-N-pentaose, para-Lacto-N-neohexaose, para-Lacto-N-hexaose, beta-(1,3)Galactosyl-para-Lacto-N-neopentaose, beta-(1,4)Galactosyl-para-Lacto-N-pentaose, Gal-a1,4-Gal-b1,4-Glc (Gal-a1,4-lactose), β3'-galactosyllactose, β6'-galactosyllactose, GalNAc-b1,3-Lactose, globo-N-tetraose, LacDiNAc and poly-LacNAc.

Most preferred mixtures in this context of the disclosure comprise mixtures that comprise, consist of or consist essentially of at least four, preferably at least five, even more preferably at least six, even more preferably at least seven, most preferably at least eight, at least nine, at least ten, different neutral non-fucosylated oligosaccharides chosen from the list comprising Lacto-N-triose II (LN3), Lacto-N-neotetraose (LNnT), Lacto-N-tetraose (LNT), para-Lacto-N-neopentaose, para-Lacto-N-pentaose, para-Lacto-N-neohexaose, para-Lacto-N-hexaose and poly-LacNAc.

Exemplary mixtures in this context of the disclosure are described in the Examples section.

For the production of lactose-based oligosaccharides as described herein and in an embodiment of the method and/or cell according to the disclosure, lactose can be added to the cultivation so that the cell can take it up passively or through active transport; or lactose can be produced by the cell (for example upon metabolically engineering the cell for this purpose as known to the skilled person), preferably intracellularly. Lactose can hence be used as an acceptor in the synthesis of a mammalian milk oligosaccharide or human milk oligosaccharide, preferably all of the lactose-based MMOs or HMOs, which is/are preferably comprised in the oligosaccharide mixture according to the disclosure as described herein. A cell producing lactose can be obtained by expression of an N-acetylglucosamine beta-1,4-galactosyltransferase and a UDP-glucose 4-epimerase. More preferably, the cell is modified for enhanced lactose production. The modification can be any one or more chosen from the group comprising over-expression of an N-acetylglucosamine beta-1,4-galactosyltransferase, over-expression of a UDP-glucose 4-epimerase. Alternatively, a cell using lactose as acceptor in glycosylation reactions preferably has a transporter for the uptake of lactose from the cultivation. More preferably, the cell is optimized for lactose uptake. The optimization can be over-expression of a lactose transporter like a lactose permease from, e.g., *E. coli, Kluyveromyces lactis* or *Lactobacillus casei* BL23. It is preferred to constitutively express the lactose permease. The lactose can be added at the start of the cultivation or it can be added as soon as enough biomass has been formed during the growth phase of the cultivation, i.e., the MMO production phase (initiated by the addition of lactose to the cultivation) is decoupled form the growth phase. In a preferred embodiment, the lactose is added at the start and/or during the cultivation, i.e., the growth phase and production phase are not decoupled.

In a preferred embodiment of the method and/or cell according to the disclosure, the cell resists the phenomenon of lactose killing when grown in an environment in which lactose is combined with one or more other carbon source(s). With the term "lactose killing" is meant the hampered growth of the cell in medium in which lactose is present together with another carbon source. In a preferred embodiment, the cell is genetically modified such that it retains at least 50% of the lactose influx without undergoing lactose killing, even at high lactose concentrations, as is described in WO 2016/075243. The genetic modification comprises expression and/or over-expression of an exogenous and/or an endogenous lactose transporter gene by a heterologous promoter that does not lead to a lactose killing phenotype and/or modification of the codon usage of the lactose transporter to create an altered expression of the lactose transporter that does not lead to a lactose killing phenotype. The content of WO 2016/075243 in this regard is incorporated by reference.

For the production of LNB-based oligosaccharides as described herein and in an additional and/or alternative embodiment of the method and/or cell according to the disclosure, LNB (i.e., lacto-N-biose, Gal-b1,3-GlcNAc) can be added to the cultivation so that the cell can take it up passively or through active transport; or LNB can be produced by the cell (for example upon metabolically engineering the cell for this purpose as known to the skilled person), preferably intracellularly. LNB can hence be used as an acceptor in the synthesis of a LNB-based oligosaccharide, preferably all of the LNB-based oligosaccharides, which is/are preferably comprised in the oligosaccharide mixture according to the disclosure as described herein. A cell producing LNB can be obtained by expression of an N-acetylglucosamine beta-1,3-galactosyltransferase which can modify GlcNAc (produced in the cell and/or taken up passively or through active transport) to form LNB. Preferably, a cell producing LNB is capable to express, preferably expresses, enzymes required for the synthesis of GlcNAc, such as glucosamine 6-phosphate N-acetyltransferase, phosphatase, N-acetylglucosamine beta-1,3-galactosyltransferase, L-glutamine-D-fructose-6-phosphate aminotransferase, and UDP-glucose 4-epimerase, preferably a glucosamine 6-phosphate N-acetyltransferase and a phosphatase, preferably a HAD-like phosphatase, like any one of, e.g., the *E. coli* genes comprising aphA, Cof, HisB, OtsB, SurE, Yaed, YcjU, YedP, YfbT, YidA, YigB, YihX, YniC, YqaB, YrbL, AppA, Gph, SerB, YbhA, YbiV, YbjL, Yfb, YieH, YjgL, YjjG, YrfG and YbiU or PsMupP from *Pseudomonas putida*, ScDOG1 from *S. cerevisiae* and BsAraL from *Bacillus subtilis* as described in WO18122225. Preferably, the cell is metabolically engineered for production of LNB. More preferably, the cell is metabolically engineered for enhanced production of LNB. The cell is preferably modified to express and/or over-express any one or more of the polypeptides comprising glucosamine 6-phosphate N-acetyltransferase, phosphatase, N-acetylglucosamine beta-1,3-galactosyltransferase, L-glutamine-D-fructose-6-phosphate aminotransferase, and UDP-glucose 4-epimerase.

A cell using LNB as acceptor in glycosylation reactions preferably has a transporter for the uptake of LNB from the cultivation. More preferably, the cell is optimized for LNB uptake. The optimization can be over-expression of a LNB transporter like a lactose permease from, e.g., *E. coli, Kluyveromyces lactis* or *Lactobacillus casei* BL23. It is preferred to constitutively express the lactose permease. The LNB can be added at the start of the cultivation or it can be added as soon as enough biomass has been formed during the growth phase of the cultivation, i.e., the oligosaccharide production phase (initiated by the addition of LNB to the cultivation) is decoupled form the growth phase. In a preferred embodiment, the LNB is added at the start and/or during the cultivation, i.e., the growth phase and production phase are not decoupled.

For the production of LacNAc-based oligosaccharides as described herein and in an additional and/or alternative embodiment of the method and/or cell according to the disclosure, LacNAc (i.e., N-acetyllactosamine, Gal-b1,4-GlcNAc) can be added to the cultivation so that the cell can take it up passively or through active transport; or LacNAc can be produced by the cell (for example upon metabolically engineering the cell for this purpose as known to the skilled person), preferably intracellularly. LacNac can hence be used as an acceptor in the synthesis of a LacNAc-based oligosaccharide, preferably all of the LacNAc-based oligosaccharides, which is/are preferably comprised in the oligosaccharide mixture according to the disclosure as described herein. A cell producing LacNAc can be obtained by expression of an N-acetylglucosamine beta-1,4-galactosyltransferase which can modify GlcNAc (produced in the cell and/or taken up passively or through active transport) to form LacNAc. Preferably, a cell producing LacNAc is capable to express, preferably expresses, enzymes required for the synthesis of GlcNAc, such as glucosamine 6-phosphate N-acetyltransferase, phosphatase, N-acetylglucosamine beta-1,4-galactosyltransferase, L-glutamine-D-fructose-6-phosphate aminotransferase, and UDP-glucose 4-epimerase, preferably a glucosamine 6-phosphate N-acetyltransferase and a phosphatase (preferably a HAD-like phosphatase as described herein). Preferably, the cell is metabolically engineered for production of LacNAc. More preferably, the cell is metabolically engineered for enhanced production of LacNAc. The cell is preferably modified to express and/or over-express any one or more of the polypeptides comprising glucosamine 6-phosphate N-acetyltransferase, phosphatase, N-acetylglucosamine beta-1,4-galactosyltransferase, L-glutamine-D-fructose-6-phosphate aminotransferase, and UDP-glucose 4-epimerase.

A cell using LacNAc as acceptor in glycosylation reactions preferably has a transporter for the uptake of LacNAc from the cultivation. More preferably, the cell is optimized for LacNAc uptake. The optimization can be over-expression of a LNB transporter like a lactose permease from *E. coli, Kluyveromyces lactis* or *Lactobacillus casei* BL23. It is preferred to constitutively express the lactose permease. The LacNAc can be added at the start of the cultivation or it can be added as soon as enough biomass has been formed during the growth phase of the cultivation, i.e., the oligosaccharide production phase (initiated by the addition of LacNAc to the cultivation) is decoupled form the growth phase. In a preferred embodiment, the LacNAc is added at the start and/or during the cultivation, i.e., the growth phase and production phase are not decoupled.

In an additional and/or alternative preferred embodiment of the method and/or cell according to the disclosure, the cell is capable to express, preferably expresses, at least two, preferably at least three, more preferably at least four, even more preferably at least five, even more preferably at least six, most preferably at least seven, glycosyltransferases as described herein.

In an additional and/or alternative preferred embodiment of the method and/or cell according to the disclosure, at least one, preferably at least two, more preferably all, of the glycosyltransferases are involved in the production of the mixture comprising at least four different oligosaccharides.

In an additional and/or alternative preferred embodiment of the method and/or cell according to the disclosure, any one of the glycosyltransferases is preferably chosen from the list comprising galactosyltransferases, glucosyltransferases, mannosyltransferases, N-acetylglucosaminyltransferases, N-acetylgalactosaminyltransferases, N-acetylmannosaminyltransferases, xylosyltransferases, glucosaminyltransferases, rhamnosyltransferases, xylosyltransferases, N-acetylrhamnosyltransferases, UDP-4-amino-4,6-dideoxy-N-acetyl-beta-L-altrosamine transaminases, UDP-N-acetylglucosamine enolpyruvyl transferases and fucosaminyltransferases as defined herein.

In a preferred embodiment, the galactosyltransferase is chosen from the list comprising beta-1,3-galactosyltransferase, N-acetylglucosamine beta-1,3-galactosyltransferase, beta-1,4-galactosyltransferase, N-acetylglucosamine beta-1,4-galactosyltransferase, alpha-1,3-galactosyltransferase and alpha-1,4-galactosyltransferase. In another preferred embodiment, the glucosyltransferase is chosen from the list comprising alpha-glucosyltransferase, beta-1,2-glucosyltransferase, beta-1,3-glucosyltransferase and beta-1,4-glucosyltransferase. In another preferred embodiment, the mannosyltransferase is chosen from the list comprising alpha-1,2-mannosyltransferase, alpha-1,3-mannosyltransferase and alpha-1,6-mannosyltransferase. In another preferred embodiment, the N-acetylglucosaminyltransferase is chosen from the list comprising galactoside beta-1,3-N-acetylglucosaminyltransferase and beta-1,6-N-acetylglucosaminyltransferase. In another preferred embodiment, the N-acetylgalactosaminyltransferase is chosen from the list comprising alpha-1,3-N-acetylgalactosaminyltransferase and beta-1,3-N-acetylgalactosaminyltransferase.

In a further embodiment of the method and/or cell of the disclosure, the cell is modified in the expression or activity of at least one, preferably at least two, more preferably all, of the glycosyltransferases. In a preferred embodiment, the glycosyltransferase is an endogenous protein of the cell with a modified expression or activity, preferably the endogenous glycosyltransferase is overexpressed; alternatively the glycosyltransferase is a heterologous protein that is heterogeneously introduced and expressed in the cell, preferably overexpressed. The endogenous glycosyltransferase can have a modified expression in the cell which also expresses a heterologous glycosyltransferase.

In another embodiment of the method and/or cell of the disclosure, at least one, preferably at least two, of the glycosyltransferases is an N-acetylglucosaminyltransferase and the cell is capable to synthesize UDP-GlcNAc. The UDP-GlcNAc can be provided by an enzyme expressed in the cell or by the metabolism of the cell. Such cell producing a UDP-GlcNAc can express enzymes converting, e.g., GlcNAc, which is to be added to the cell, to UDP-GlcNAc. These enzymes may be an N-acetyl-D-glucosamine kinase, an N-acetylglucosamine-6-phosphate deacetylase, a phosphoglucosamine mutase, and an N-acetylglucosamine-1-phosphate uridyltransferase/glucosamine-1-phosphate acetyltransferase from several species including *Homo sapiens, Escherichia coli*. Alternatively, a cell can (preferably metabolically engineered to) express enzymes required for the synthesis of GlcNAc, such as glucosamine 6-phosphate N-acetyltransferase, phosphatase, glycosyltransferase, L-glutamine-D-fructose-6-phosphate aminotransferase, and UDP-glucose 4-epimerase, preferably a glucosamine 6-phosphate N-acetyltransferase and a phosphatase (preferably a HAD-like phosphatase as described herein). In a preferred embodiment of the method and/or cell of the disclosure, the cell is capable of expressing at least one, preferably at least two, N-acetylglucosaminyltransferase(s) selected from beta-1,3-N-acetylglucosaminyltransferases and beta-1,6-N-acetylglucosaminyltransferases. Preferably, the N-acetylglucosaminyltransferases are selected from organisms like, e.g., *Neisseria* species, like, e.g., *Neisseria meningitidis, Neisseria lactamica, Neisseria polysaccharea, Neisseria elongata, Neisseria gonorrhoeae, Neisseria subflava, Pasteurella* species like, e.g., *Pasteurella dagmatis, Neorhizobium* species like, e.g., *Neorhizobium galegae, Haemophilus* species like, e.g., *Haemophilus parainfluenzae, Haemophilus ducreyi, Homo sapiens, Mus musculus.*

Preferably, the cell is modified to produce UDP-GlcNAc. More preferably, the cell is modified for enhanced UDP-GlcNAc production. The modification can be any one or more chosen from the group comprising knock-out of an N-acetylglucosamine-6-phosphate deacetylase, over-expression of an L-glutamine-D-fructose-6-phosphate aminotransferase, over-expression of a phosphoglucosamine mutase, and over-expression of an N-acetylglucosamine-1-phosphate uridyltransferase/glucosamine-1-phosphate acetyltransferase. Throughout the application, unless explicitly stated otherwise, the feature "enhanced" and/or "optimized" production preferably means that the modification(s) and/or metabolic engineering introduced in a cell as described herein results in a higher production yield compared to the wild type progenitor of the modified cell or metabolically engineered cell. For example, "an enhanced UDP-GlcNAc production" preferably means that the intracellular production of UDP-GlcNAc is higher in the modified cell compared to the wild type progenitor which does not contain these specific modifications.

Preferably, the cell in this context comprises an N-acetylglucosamine carbohydrate pathway as described herein.

In another embodiment of the method and/or cell of the disclosure, at least one, preferably at least two, of the glycosyltransferases is a galactosyltransferase and the cell is capable to synthesize UDP-Gal. The UDP-Gal can be provided by an enzyme expressed in the cell or by the metabolism of the cell. Such cell producing UDP-Gal can express an enzyme converting, e.g., UDP-glucose, to UDP-Gal. This enzyme may be, e.g., the UDP-glucose-4-epimerase GalE like as known from several species including *Homo sapiens, Escherichia coli*, and *Rattus norvegicus*. In a preferred embodiment of the method and/or cell of the disclosure, the cell is capable of expressing at least one, preferably at least two, galactosyltransferase(s) selected from beta-1,3-galactosyltransferases and beta-1,4-galactosyltransferases, and/or the cell is capable of expressing at least one, preferably at least two, galactosyltransferases selected from alpha-1,3-galactosyltransferases and alpha-1,4-galactosyltransferases. Preferably, the galactosyltransferases are chosen from organisms like, e.g., *E. coli* species like e.g. *E. coli* O55:H7, *E. coli* DEC1B, *E. coli* DEC1D, *Neisseria* species like, e.g., *Neisseria meningitidis, Neisseria lactamica, Neisseria polysaccharea, Neisseria elongata, Neisseria gonorrhoeae, Neisseria subflava, Kingella* species like, e.g., *Kingella denitrificans, Brucella* species like, e.g., *Brucella canis, Brucella suis, Salmonella* species, like, e.g., *Salmonella enterica, Pseudogulbenkiana ferrooxidans, Corynebacterium glutamicum, Streptococcus* species, *Arabidopsis thaliana, Homo sapiens, Mus musculus.*

Preferably, the cell is modified to produce UDP-Gal. More preferably, the cell is modified for enhanced UDP-Gal production. The modification can be any one or more chosen from the group comprising knock-out of a bifunctional 5'-nucleotidase/UDP-sugar hydrolase encoding gene, knock-out of a galactose-1-phosphate uridylyltransferase encoding gene and over-expression of a UDP-glucose-4-epimerase encoding gene.

Preferably, the cell in this context comprises a galactosylation pathway as described herein.

In another embodiment of the method and/or cell of the disclosure, at least one, preferably at least two, of the glycosyltransferases is an N-acetylgalactosaminyltransferase and the cell is capable to synthesize UDP-GalNAc. The UDP-GalNAc can be provided by an enzyme expressed in the cell or by the metabolism of the cell. Such cell producing UDP-GalNAc can express an enzyme converting, e.g., UDP-glucose, to UDP-Gal. This enzyme may be, e.g., the UDP-glucose-4-epimerase GalE like as known from several species including *Homo sapiens, Escherichia coli*, and *Rattus norvegicus*. In a preferred embodiment of the method and/or cell of the disclosure, the cell is capable of expressing at least one, preferably at least two, N-acetylgalactosaminyltransferase(s) selected from alpha-1,3-N-acetylgalactosaminyltransferases and beta-1,3-N-acetylgalactosaminyltransferases. Preferably, the N-acetylgalactosaminyltransferases are chosen from organisms like, e.g., *Helicobacter* species like, e.g., *Helicobacter mustelae, Haemophilus* species like, e.g., *Haemophilus influenzae, Neisseria* species like, e.g., *Neisseria meningitidis, Neisseria lactamica, Neisseria polysaccharea, Neisseria elongata, Neisseria gonorrhoeae, Neisseria subflava, Rickettsia* species like, e.g., *Rickettsia bellii, Rickettsia prowazekii, Rickettsia japonica, Rickettsia conorii, Rickettsia felis,*

*Rickettsia massiliae, Homo sapiens, Mus musculus*. Preferably, the cell is modified to produce UDP-GalNAc. More preferably, the cell is modified for enhanced UDP-GalNAc production. The modification can be any one or more chosen from the group comprising knock-out of a bifunctional 5'-nucleotidase/UDP-sugar hydrolase encoding gene, knock-out of a galactose-1-phosphate uridylyltransferase encoding gene and over-expression of a UDP-glucose-4-epimerase encoding gene.

Preferably, the cell in this context comprises an N-acetylgalactosaminylation pathway as described herein.

Throughout the application, whenever a protein is disclosed, e.g., by referring to a SEQ ID NO, a unique database number (e.g., UNIPROT number) or by referring to the specific organism of origin, the protein embodiment can be preferably replaced with any, preferably all, of the following embodiments (and hence the protein is considered to be disclosed according to all of the following embodiment):
- protein (e.g., by referring to a SEQ ID NO, a unique database number (e.g., UNIPROT number) or by referring to the specific organism of origin),
- a functional homologue, variant or derivative of the protein having at least 80% overall sequence identity to the full length of the protein,
- a functional fragment of the protein and having the same activity, or
- comprises a polypeptide comprising or consisting of an amino acid sequence having at least 80% sequence identity to the full-length amino acid sequence of the protein and having the same activity.

For example, when "galactoside beta-1,3-N-acetylglucosaminyltransferase (LgtA) from *N. meningitidis* (UniProt ID Q9JXQ6)" is disclosed, the embodiment is preferably replaced with any, preferably all, of the following embodiments:
- galactoside beta-1,3-N-acetylglucosaminyltransferase (LgtA) from *N. meningitidis* (UniProt ID Q9JXQ6),
- galactoside beta-1,3-N-acetylglucosaminyltransferase comprising a polypeptide sequence according to UniProt ID Q9JXQ6,
- a functional homologue, variant or derivative of UniProt ID Q9JXQ6 having at least 80% overall sequence identity to the full length of UniProt ID Q9JXQ6 having galactoside beta-1,3-N-acetylglucosaminyltransferase activity,
- a functional fragment of UniProt ID Q9JXQ6 and having galactoside beta-1,3-N-acetylglucosaminyltransferase activity, or
- comprises a polypeptide comprising or consisting of an amino acid sequence having at least 80% sequence identity to the full-length amino acid sequence of the UniProt ID Q9JXQ6 and having galactoside beta-1,3-N-acetylglucosaminyltransferase activity.

In another embodiment of the method and/or cell of the disclosure, the cell is capable to synthesize any one of the nucleotide-sugars chosen from the list comprising UDP-N-acetylglucosamine (UDP-GlcNAc), UDP-galactose (UDP-Gal), UDP-N-acetylgalactosamine (UDP-GalNAc), UDP-N-acetylmannosamine (UDP-ManNAc), GDP-mannose (GDP-Man), UDP-glucose (UDP-Glc), GDP-rhamnose, UDP-xylose, UDP-2-acetamido-2,6-dideoxy-L-arabino-4-hexulose, UDP-2-acetamido-2,6-dideoxy-L-lyxo-4-hexulose, UDP-N-acetyl-L-rhamnosamine (UDP-L-RhaNAc or UDP-2-acetamido-2,6-dideoxy-L-mannose), dTDP-N-acetylfucosamine, UDP-N-acetylfucosamine (UDP-L-FucNAc or UDP-2-acetamido-2,6-dideoxy-L-galactose), UDP-N-acetyl-L-pneumosamine (UDP-L-PneNAC or UDP-2-acetamido-2,6-dideoxy-L-talose), UDP-N-acetylmuramic acid, UDP-N-acetyl-L-quinovosamine (UDP-L-QuiNAc or UDP-2-acetamido-2,6-dideoxy-L-glucose), GDP-L-quinovose. In a preferred embodiment, the cell is capable to synthesize two nucleotide-sugars. In a more preferred embodiment, the cell is capable to synthesize at least three nucleotide-activated sugars. In an even more preferred embodiment, the cell is capable to synthesize at least four nucleotide-activated sugars. In a most preferred embodiment, the cell is capable to synthesize at least five nucleotide-activated sugars. In another preferred embodiment, the cell is metabolically engineered for the production of a nucleotide-sugar. In another preferred embodiment, the cell is modified and/or engineered for the optimized production of a nucleotide-sugar, i.e., enhanced production of a nucleotide-sugar as described herein. In a more preferred embodiment, the cell is metabolically engineered for the production of two nucleotide-activated sugars. In an even more preferred embodiment, the cell is metabolically engineered for the production of three or more nucleotide-activated sugars.

In another embodiment of the method and/or cell of the disclosure, the cell expresses one or more polypeptides chosen from the list comprising L-glutamine-D-fructose-6-phosphate aminotransferase, glucosamine-6-phosphate deaminase, phosphoglucosamine mutase, N-acetylglucosamine-6-phosphate deacetylase, N-acylglucosamine 2-epimerase, UDP-N-acetylglucosamine 2-epimerase, N-acetylmannosamine-6-phosphate 2-epimerase, glucosamine 6-phosphate N-acetyltransferase, N-acetylglucosamine-6-phosphate phosphatase, N-acetylmannosamine-6-phosphate phosphatase, N-acetylmannosamine kinase, phosphoacetylglucosamine mutase, N-acetylglucosamine-1-phosphate uridylyltransferase, glucosamine-1-phosphate acetyltransferase, galactose-1-epimerase, galactokinase, glucokinase, galactose-1-phosphate uridylyltransferase, UDP-glucose 4-epimerase, glucose-1-phosphate uridylyltransferase, phosphoglucomutase, UDP-N-acetylglucosamine 4-epimerase, N-acetylgalactosamine kinase and UDP-N-acetylgalactosamine pyrophosphorylase.

In a preferred embodiment of the method and/or cell according to the disclosure, the mixture of at least four different oligosaccharides according to the disclosure can be produced by providing a cell which, for the production of lactose-based neutral non-fucosylated oligosaccharides, is 1) capable to take up lactose from the cultivation as described herein or is able to produce lactose after uptake of glucose by the action of a b-1,4-galactosyltransferase as described herein; and 2) capable to express an N-acetylglucosaminyltransferase as described herein, preferably a galactoside beta-1,3-N-acetylglucosaminyltransferase; 3) optionally capable to express at least one, preferably at least two, galactosyltransferase(s) as described herein, chosen from the list comprising an N-acetylglucosamine beta-1,3-galactosyltransferase, an N-acetylglucosamine beta-1,4-galactosyltransferase, an alpha-1,3-galactosyltransferase, an alpha-1,4-galactosyltransferase; and 4) optionally capable to express at least one, preferably at least two, N-acetylgalactosaminyltransferase(s) as described herein, chosen from the list comprising an alpha-1,3-N-acetylgalactosaminyltransferase and a beta-1,3-N-acetylgalactosaminyltransferase and 5) capable to synthesize the nucleotide-sugar of each of the glycosyltransferases if present.

In another and/or additional preferred embodiment of the method and/or cell according to the disclosure, the mixture of at least four different neutral non-fucosylated oligosaccharides according to the disclosure can be produced by providing a cell which, for the production of LNB-based neutral non-fucosylated oligosaccharides, is able to produce LNB as described herein or capable to take up LNB from the cultivation; and capable to synthesize UDP-Gal.

In another and/or additional preferred embodiment of the method and/or cell according to the disclosure, the mixture of at least four different neutral non-fucosylated oligosaccharides according to the disclosure can be produced by providing a cell which, for the production of LacNAc-based neutral non-fucosylated oligosaccharides, is able to produce LacNAc as described herein or capable to take up LacNAc from the cultivation; and capable to synthesize UDP-Gal.

Exemplary methods and cells according to the disclosure are described in the Examples section. It is emphasized that these examples show at least one way to produce the specific mixtures. The person skilled in the art will understand that any of the expressed enzymes can be replaced by another enzyme if it has the same catalytic activity, preferably to a similar extent, which can be readily assessed through routine experimentation wherein the activity of an enzyme is compared with the activity of a reference enzyme as disclosed herein (e.g., in vitro conversion of a substrate).

In a preferred embodiment of the method and/or cell of the disclosure, any one of the neutral non-fucosylated oligosaccharides, more preferably all of the oligosaccharides, is/are translocated to the outside of the cell by a passive transport, i.e., without means of an active transport system consuming energy from the cell.

In a preferred embodiment of the method and/or cell of the disclosure, the cell uses at least one precursor for the production of any one or more of the oligosaccharides. The term "precursor" should be understood as explained in the definitions as disclosed herein. In a more preferred embodiment, the cell uses two or more precursors for the production of any one or more of the oligosaccharides.

In a preferred embodiment of the method of the disclosure, the cultivation is fed with a precursor and/or acceptor for the synthesis of any one of the oligosaccharides in the mixture. The term "acceptor" should be understood as explained in the definitions as disclosed herein. In a further preferred embodiment of the method, the cultivation is fed with at least two precursors and/or acceptors for the synthesis of any one or more, preferably all, of the oligosaccharides in the mixture. This can be useful if two or more glycosyltransferases of the same classification are used which have a different affinity (e.g., one having affinity to lactose and the other having affinity to lacto-N-biose) for the production of a mixture of oligosaccharides according to the disclosure.

In another embodiment of the method and/or cell as described herein, the cell is producing a precursor for the production of any one of the oligosaccharides. In a preferred embodiment, the cell is producing one or more precursors for the synthesis of the oligosaccharide mixture. In a more preferred embodiment, the cell is modified for optimized production of any one of the precursors for the synthesis of any one of the oligosaccharides.

In a preferred embodiment of the method and/or cell of the disclosure, at least one precursor for the production of any one of the oligosaccharides is completely converted into any one of the oligosaccharides. In a more preferred embodiment, the cell completely converts any one of the precursors into any one of the oligosaccharides.

In another preferred embodiment of the method and/or cell of the disclosure, the cell is further metabolically engineered for i) modified expression of an endogenous membrane protein, and/or
ii) modified activity of an endogenous membrane protein, and/or
iii) expression of a homologous membrane protein, and/or
iv) expression of a heterologous membrane protein,
wherein the membrane protein is involved in the secretion of any one of the neutral non-fucosylated oligosaccharides outside the cell. The cell can express one of the membrane proteins that is involved in the secretion of any one of the neutral non-fucosylated oligosaccharides from the cell to the outside of the cell. The cell can also express more than one of the membrane proteins. Any one of the membrane proteins can translocate one or more of the neutral non-fucosylated oligosaccharides to the outside of the cell. The cell producing a mixture of at least four neutral non-fucosylated oligosaccharides can translocate any one of the oligosaccharides comprising passive diffusion, channel membrane proteins, membrane transporter proteins, membrane carrier proteins.

In another preferred embodiment of the method and/or cell of the disclosure, the cell is further metabolically engineered for i) modified expression of an endogenous membrane protein, and/or
ii) modified activity of an endogenous membrane protein, and/or
iii) expression of a homologous membrane protein, and/or
iv) expression of a heterologous membrane protein,
wherein the membrane protein is involved in the uptake of a precursor and/or acceptor for the synthesis of any one of the neutral non-fucosylated oligosaccharides. The cell can express one of the membrane proteins that is involved in the uptake of any type of precursor and/or acceptor used in the synthesis of any one of the neutral non-fucosylated oligosaccharides. The cell can also express more than one of the membrane proteins, involved in the uptake of at least one of the precursors and/or acceptors. The cell can be modified for the uptake of more than one precursor and/or acceptor for the synthesis of any one of the neutral non-fucosylated oligosaccharides.

In a more preferred embodiment of the method and/or cell of the disclosure, the membrane protein is chosen from the list comprising porters, P-P-bond-hydrolysis-driven transporters, β-barrel porins, auxiliary transport proteins, putative transport proteins and phosphotransfer-driven group translocators. In an even more preferred embodiment of the method and/or cell of the disclosure, the porters comprise MFS transporters, sugar efflux transporters and siderophore exporters. In another more preferred embodiment of the method and/or cell of the disclosure, the P-P-bond-hydrolysis-driven transporters comprise ABC transporters and siderophore exporters.

In another preferred embodiment of the method and/or cell of the disclosure, the membrane protein provides improved production of any one of the oligosaccharides, preferably all of the oligosaccharides. In an alternative and/or additional preferred embodiment of the method and/or cell of the disclosure, the membrane protein provides enabled efflux of any one of the oligosaccharides, preferably all of the oligosaccharides. In an alternative and/or additional preferred embodiment of the method and/or cell of the disclosure, the membrane protein provides enhanced efflux of any one of the oligosaccharides, preferably all of the oligosaccharides.

In a more preferred embodiment of the method and/or cell of the disclosure, the cell expresses a membrane protein belonging to the family of MFS transporters like, e.g., an MdfA polypeptide of the multidrug transporter MdfA family from species comprising *E. coli* (UniProt ID P0AEY8), *Cronobacter muytjensii* (UniProt ID A0A2T7ANQ9), *Citrobacter youngae* (UniProt ID D4BC23) and *Yokenella regensburgei* (UniProt ID G9Z5F4). In another more preferred embodiment of the method and/or cell of the disclosure, the cell expresses a membrane protein belonging to the family of sugar efflux transporters like, e.g., a SetA polypeptide of the SetA family from species comprising *E. coli* (UniProt ID P31675), *Citrobacter koseri* (UniProt ID A0A078LM16) and *Klebsiella pneumoniae* (UniProt ID A0A0C4MGS7). In another more preferred embodiment of the method and/or cell of the disclosure, the cell expresses a membrane protein belonging to the family of siderophore exporters like, e.g., the *E. coli* entS (UniProt ID P24077) and the *E. coli* iceT (UniProt ID A0A024L207). In another more preferred embodiment of the method and/or cell of the disclosure, the cell expresses a membrane protein belonging to the family of ABC transporters like, e.g., oppF from *E. coli* (UniProt ID P77737), lmrA from *Lactococcus lactis* subsp. *lactis* bv. *diacetylactis* (UniProt ID A0A1VONEL4) and Blon_2475 from *Bifidobacterium longum* subsp. *infantis* (UniProt ID B7GPD4).

In a preferred embodiment of the method and/or cell of the disclosure, the cell confers enhanced bacteriophage resistance. The enhancement of bacteriophage resistance can be derived from reduced expression of an endogenous membrane protein and/or mutation of an endogenous membrane protein encoding gene. The term "phage insensitive" or "phage resistant" or "phage resistance" or "phage resistant profile" is understood to mean a bacterial strain that is less sensitive, and preferably insensitive to infection and/or killing by phage and/or growth inhibition. As used herein, the terms "anti-phage activity" or "resistant to infection by at least one phage" refers to an increase in resistance of a bacterial cell expressing a functional phage resistance system to infection by at least one phage family in comparison to a bacterial cell of the same species under the same developmental stage (e.g., culture state) which does not express a functional phage resistance system, as may be determined by, e.g., bacterial viability, phage lysogeny, phage genomic replication and phage genomic degradation. The phage can be a lytic phage or a temperate (lysogenic) phage. Membrane proteins involved in bacteriophage resistance of a cell comprise OmpA, OmpC, OmpF, OmpT, BtuB, TolC, LamB, FhuA, TonB, FadL, Tsx, FepA, YncD, PhoE, and NfrA and homologs thereof.

In a preferred embodiment of the method and/or cell of the disclosure, the cell confers reduced viscosity. Reduced viscosity of a cell can be obtained by a modified cell wall biosynthesis. Cell wall biosynthesis can be modified comprising reduced or abolished synthesis of for example poly-N-acetyl-glucosamine, the enterobacterial common antigen, cellulose, colanic acid, core oligosaccharides, osmoregulated periplasmic glucans and glucosylglycerol, glycan, and trehalose.

According to another embodiment of the method and/or cell of the disclosure, the cell is capable to produce phosphoenolpyruvate (PEP). In a preferred embodiment of the method and/or cell of the disclosure, the cell is modified for enhanced production and/or supply of PEP compared to a non-modified progenitor.

In a preferred embodiment and as a means for enhanced production and/or supply of PEP, one or more PEP-dependent, sugar-transporting phosphotransferase system(s) is/are disrupted such as but not limited to: 1) the N-acetyl-D-glucosamine Npi-phosphotransferase (EC 2.7.1.193), which is for instance encoded by the nagE gene (or the cluster nagABCD) in *E. coli* or *Bacillus* species, 2) ManXYZ which encodes the Enzyme 11 Man complex (mannose PTS permease, protein-Npi-phosphohistidine-D-mannose phosphotransferase) that imports exogenous hexoses (mannose, glucose, glucosamine, fructose, 2-deoxyglucose, mannosamine, N-acetylglucosamine, etc.) and releases the phosphate esters into the cell cytoplasm, 3) the glucose-specific PTS transporter (for instance encoded by PtsG/Crr) which takes up glucose and forms glucose-6-phosphate in the cytoplasm, 4) the sucrose-specific PTS transporter which takes up sucrose and forms sucrose-6-phosphate in the cytoplasm, 5) the fructose-specific PTS transporter (for instance encoded by the genes fruA and fruB and the kinase fruK which takes up fructose and forms in a first step fructose-1-phosphate and in a second step fructose1,6 bisphosphate, 6) the lactose PTS transporter (for instance encoded by lacE in *Lactococcus casei*) which takes up lactose and forms lactose-6-phosphate, 7) the galactitol-specific PTS enzyme which takes up galactitol and/or sorbitol and forms galactitol-1-phosphate or sorbitol-6-phosphate respectively, 8) the mannitol-specific PTS enzyme which takes up mannitol and/or sorbitol and forms mannitol-1-phosphate or sorbitol-6-phosphate respectively, and 9) the trehalose-specific PTS enzyme which takes up trehalose and forms trehalose-6-phosphate.

In another and/or additional preferred embodiment and as a means for enhanced production and/or supply of PEP, the full PTS system is disrupted by disrupting the PtsIH/Crr gene cluster. PtsI (Enzyme I) is a cytoplasmic protein that serves as the gateway for the phosphoenolpyruvate:sugar phosphotransferase system (PTSsugar) of *E. coli* K-12. PtsI is one of two (PtsI and PtsH) sugar non-specific protein constituents of the PTSsugar which along with a sugar-specific inner membrane permease effects a phosphotransfer cascade that results in the coupled phosphorylation and transport of a variety of carbohydrate substrates. HPr (histidine containing protein) is one of two sugar-non-specific protein constituents of the PTSsugar. It accepts a phosphoryl group from phosphorylated Enzyme I (PtsI-P) and then transfers it to the EIIA domain of any one of the many sugar-specific enzymes (collectively known as Enzymes II) of the PTSsugar. Crr or EIIAGlc is phosphorylated by PEP in a reaction requiring PtsH and PtsI.

In another and/or additional preferred embodiment, the cell is further modified to compensate for the deletion of a PTS system of a carbon source by the introduction and/or overexpression of the corresponding permease. These are, e.g., permeases or ABC transporters that comprise but are not limited to transporters that specifically import lactose such as, e.g., the transporter encoded by the LacY gene from *E. coli*, sucrose such as, e.g., the transporter encoded by the cscB gene from *E. coli*, glucose such as, e.g., the transporter encoded by the galP gene from *E. coli*, fructose such as, e.g., the transporter encoded by the fruI gene from *Streptococcus mutans*, or the Sorbitol/mannitol ABC transporter such as the transporter encoded by the cluster SmoEFGK of *Rhodobacter sphaeroides*, the trehalose/sucrose/maltose transporter such as the transporter encoded by the gene cluster ThuEFGK of *Sinorhizobium meliloti* and the N-acetylglucosamine/galactose/glucose transporter such as the transporter encoded by NagP of *Shewanella oneidensis*. Examples of combinations of PTS deletions with overexpression of alternative transporters are: 1) the deletion of the glucose PTS system, e.g., ptsG gene, combined with the introduction and/or overexpression of a glucose permease (e.g., galP of glcP), 2) the deletion of the fructose PTS system, e.g., one or more of the fruB, fruA, fruK genes, combined with the introduction and/or overexpression of fructose permease, e.g., fruI, 3) the deletion of the lactose PTS system, combined with the introduction and/or overexpression of lactose permease, e.g., LacY, and/or 4) the deletion of the sucrose PTS system, combined with the introduction and/or overexpression of a sucrose permease, e.g., cscB.

In a further preferred embodiment, the cell is modified to compensate for the deletion of a PTS system of a carbon source by the introduction of carbohydrate kinases, such as glucokinase (EC 2.7.1.1, EC 2.7.1.2, EC 2.7.1.63), galactokinase (EC 2.7.1.6), and/or fructokinase (EC 2.7.1.3, EC 2.7.1.4). Examples of combinations of PTS deletions with overexpression of alternative transporters and a kinase are: 1) the deletion of the glucose PTS system, e.g., ptsG gene, combined with the introduction and/or overexpression of a glucose permease (e.g., galP of glcP), combined with the introduction and/or overexpression of a glucokinase (e.g., glk), and/or 2) the deletion of the fructose PTS system, e.g. one or more of the fruB, fruA, fruK genes, combined with the introduction and/or overexpression of fructose permease, e.g., fruI, combined with the introduction and/or overexpression of a fructokinase (e.g., frk or mak).

In another and/or additional preferred embodiment and as a means for enhanced production and/or supply of PEP, the cell is modified by the introduction of or modification in any one or more of the list comprising phosphoenolpyruvate synthase activity (EC: 2.7.9.2 encoded for instance in *E. coli* by ppsA), phosphoenolpyruvate carboxykinase activity (EC 4.1.1.32 or EC 4.1.1.49 encoded for instance in *Corynebacterium glutamicum* by PCK or in *E. coli* by pckA, resp.), phosphoenolpyruvate carboxylase activity (EC 4.1.1.31 encoded for instance in *E. coli* by ppc), oxaloacetate decarboxylase activity (EC 4.1.1.112 encoded for instance in *E. coli* by eda), pyruvate kinase activity (EC 2.7.1.40 encoded for instance in *E. coli* by pykA and pykF), pyruvate carboxylase activity (EC 6.4.1.1 encoded for instance in *B. subtilis* by pyc) and malate dehydrogenase activity (EC 1.1.1.38 or EC 1.1.1.40 encoded for instance in *E. coli* by maeA or maeB, resp.).

In a more preferred embodiment, the cell is modified to overexpress any one or more of the polypeptides comprising ppsA from *E. coli* (UniProt ID P23538), PCK from *C. glutamicum* (UniProt ID Q6F5A5), pcka from *E. coli* (UniProt ID P22259), eda from *E. coli* (UniProt ID P0A955), maeA from *E. coli* (UniProt ID P26616) and maeB from *E. coli* (UniProt ID P76558).

In another and/or additional preferred embodiment, the cell is modified to express any one or more polypeptide having phosphoenolpyruvate synthase activity, phosphoenolpyruvate carboxykinase activity, oxaloacetate decarboxylase activity, or malate dehydrogenase activity.

In another and/or additional preferred embodiment and as a means for enhanced production and/or supply of PEP, the cell is modified by a reduced activity of phosphoenolpyruvate carboxylase activity, and/or pyruvate kinase activity, preferably a deletion of the genes encoding for phosphoenolpyruvate carboxylase, the pyruvate carboxylase activity and/or pyruvate kinase.

In an exemplary embodiment, the cell is genetically modified by different adaptations such as the overexpression of phosphoenolpyruvate synthase combined with the deletion of a pyruvate kinase gene, the overexpression of phosphoenolpyruvate synthase combined with the deletion of a phosphoenolpyruvate carboxylase gene, the overexpression of phosphoenolpyruvate synthase combined with the deletion of a pyruvate carboxylase gene, the overexpression of phosphoenolpyruvate carboxykinase combined with the deletion of a pyruvate kinase gene, the overexpression of phosphoenolpyruvate carboxykinase combined with the deletion of a phosphoenolpyruvate carboxylase gene, the overexpression of phosphoenolpyruvate carboxykinase combined with the deletion of a pyruvate carboxylase gene, the overexpression of oxaloacetate decarboxylase combined with the deletion of a pyruvate kinase gene, the overexpression of oxaloacetate decarboxylase combined with the deletion of a phosphoenolpyruvate carboxylase gene, the overexpression of oxaloacetate decarboxylase combined with the deletion of a pyruvate carboxylase gene, the overexpression of malate dehydrogenase combined with the deletion of a pyruvate kinase gene, the overexpression of malate dehydrogenase combined with the deletion of a phosphoenolpyruvate carboxylase gene and/or the overexpression of malate dehydrogenase combined with the deletion of a pyruvate carboxylase gene.

In another exemplary embodiment, the cell is genetically modified by different adaptations such as the overexpression of phosphoenolpyruvate synthase combined with the overexpression of a phosphoenolpyruvate carboxykinase, the overexpression of phosphoenolpyruvate synthase combined with the overexpression of an oxaloacetate decarboxylase, the overexpression of phosphoenolpyruvate synthase combined with the overexpression of a malate dehydrogenase, the overexpression of phosphoenolpyruvate carboxykinase combined with the overexpression of an oxaloacetate decarboxylase, the overexpression of phosphoenolpyruvate carboxykinase combined with the overexpression of a malate dehydrogenase, the overexpression of oxaloacetate decarboxylase combined with the overexpression of a malate dehydrogenase, the overexpression of phosphoenolpyruvate synthase combined with the overexpression of a phosphoenolpyruvate carboxykinase and the overexpression of an oxaloacetate decarboxylase, the overexpression of phosphoenolpyruvate synthase combined with the overexpression of a phosphoenolpyruvate carboxykinase and the overexpression of a malate dehydrogenase, the overexpression of phosphoenolpyruvate synthase combined with the overexpression of a phosphoenolpyruvate carboxykinase and the overexpression of an oxaloacetate decarboxylase and the overexpression of a malate dehydrogenase, the overexpression of phosphoenolpyruvate carboxykinase combined with the overexpression of an oxaloacetate decarboxylase and the overexpression of a malate dehydrogenase and/or the overexpression of phosphoenolpyruvate synthase combined with the overexpression of an oxaloacetate decarboxylase and the overexpression of a malate dehydrogenase.

In another exemplary embodiment, the cell is genetically modified by different adaptations such as the overexpression of phosphoenolpyruvate synthase combined with the overexpression of a phosphoenolpyruvate carboxykinase combined with the deletion of a pyruvate kinase gene, the overexpression of phosphoenolpyruvate synthase combined with the overexpression of an oxaloacetate decarboxylase combined with the deletion of a pyruvate kinase gene, the overexpression of phosphoenolpyruvate synthase combined with the overexpression of a malate dehydrogenase combined with the deletion of a pyruvate kinase gene, the overexpression of phosphoenolpyruvate carboxykinase combined with the overexpression of an oxaloacetate decarboxylase combined with the deletion of a pyruvate kinase gene, the overexpression of phosphoenolpyruvate carboxykinase combined with the overexpression of a malate dehydrogenase combined with the deletion of a pyruvate kinase gene, the overexpression of an oxaloacetate decarboxylase combined with the overexpression of a malate dehydrogenase combined with the deletion of a pyruvate kinase gene, the overexpression of phosphoenolpyruvate synthase combined with the overexpression of a phosphoenolpyruvate carboxykinase and the overexpression of an oxaloacetate decarboxylase combined with the deletion of a pyruvate kinase gene, the overexpression of phosphoenolpyruvate synthase combined with the overexpression of a phosphoenolpyruvate carboxykinase and the overexpression of a malate dehydrogenase combined with the deletion of a pyruvate kinase gene, the overexpression of phosphoenolpyruvate synthase combined with the overexpression of a phosphoenolpyruvate carboxykinase and the overexpression of an oxaloacetate decarboxylase and the overexpression of a malate dehydrogenase combined with the deletion of a pyruvate kinase gene, the overexpression of a phosphoenolpyruvate carboxykinase combined with the overexpression of an oxaloacetate decarboxylase and the overexpression of a malate dehydrogenase combined with the deletion of a pyruvate kinase gene, the overexpression of phosphoenolpyruvate synthase combined with the overexpression of oxaloacetate decarboxylase and the overexpression of a malate dehydrogenase combined with the deletion of a pyruvate kinase gene.

In another exemplary embodiment, the cell is genetically modified by different adaptations such as the overexpression of phosphoenolpyruvate synthase combined with the overexpression of a phosphoenolpyruvate carboxykinase combined with the deletion of a phosphoenolpyruvate carboxylase gene, the overexpression of phosphoenolpyruvate synthase combined with the overexpression of an oxaloacetate decarboxylase combined with the deletion of a phosphoenolpyruvate carboxylase gene, the overexpression of phosphoenolpyruvate synthase combined with the overexpression of a malate dehydrogenase combined with the deletion of a phosphoenolpyruvate carboxylase gene, the overexpression of a phosphoenolpyruvate carboxykinase combined with the overexpression of an oxaloacetate decarboxylase combined with the deletion of a phosphoenolpyruvate carboxylase gene, the overexpression of a phosphoenolpyruvate carboxykinase combined with the overexpression of a malate dehydrogenase combined with the deletion of a phosphoenolpyruvate carboxylase gene, the overexpression of an oxaloacetate decarboxylase combined with the overexpression of a malate dehydrogenase combined with the deletion of a phosphoenolpyruvate carboxylase gene, the overexpression of phosphoenolpyruvate synthase combined with the overexpression of a phosphoenolpyruvate carboxykinase and the overexpression of an oxaloacetate decarboxylase combined with the deletion of a phosphoenolpyruvate carboxylase gene, the overexpression of phosphoenolpyruvate synthase combined with the overexpression of a phosphoenolpyruvate carboxykinase and the overexpression of a malate dehydrogenase combined with the deletion of a phosphoenolpyruvate carboxylase gene, the overexpression of phosphoenolpyruvate synthase combined with the overexpression of a phosphoenolpyruvate carboxykinase and the overexpression of an oxaloacetate decarboxylase and the overexpression of a malate dehydrogenase combined with the deletion of a phosphoenolpyruvate carboxylase gene, the overexpression of a phosphoenolpyruvate carboxykinase combined with the overexpression of an oxaloacetate decarboxylase and the overexpression of a malate dehydrogenase combined with the deletion of a phosphoenolpyruvate carboxylase gene, the overexpression of phosphoenolpyruvate synthase combined with the overexpression of an oxaloacetate decarboxylase and the overexpression of a malate dehydrogenase combined with the deletion of a phosphoenolpyruvate carboxylase gene.

In another exemplary embodiment, the cell is genetically modified by different adaptations such as the overexpression of phosphoenolpyruvate synthase combined with the overexpression of a phosphoenolpyruvate carboxykinase combined with the deletion of a pyruvate carboxylase gene, the overexpression of phosphoenolpyruvate synthase combined with the overexpression of an oxaloacetate decarboxylase combined with the deletion of a pyruvate carboxylase gene, the overexpression of phosphoenolpyruvate synthase combined with the overexpression of a malate dehydrogenase combined with the deletion of a pyruvate carboxylase gene, the overexpression of a phosphoenolpyruvate carboxykinase combined with the overexpression of an oxaloacetate decarboxylase combined with the deletion of a pyruvate carboxylase gene, the overexpression of a phosphoenolpyruvate carboxykinase combined with the overexpression of a malate dehydrogenase combined with the deletion of a pyruvate carboxylase gene, the overexpression of an oxaloacetate decarboxylase combined with the overexpression of a malate dehydrogenase combined with the deletion of a pyruvate carboxylase gene, the overexpression of phosphoenolpyruvate synthase combined with the overexpression of a phosphoenolpyruvate carboxykinase and the overexpression of an oxaloacetate decarboxylase combined with the deletion of a pyruvate carboxylase gene, the overexpression of phosphoenolpyruvate synthase combined with the overexpression of a phosphoenolpyruvate carboxykinase and the overexpression of a malate dehydrogenase combined with the deletion of a pyruvate carboxylase gene, the overexpression of phosphoenolpyruvate synthase combined with the overexpression of a phosphoenolpyruvate carboxykinase and the overexpression of an oxaloacetate decarboxylase and the overexpression of a malate dehydrogenase combined with the deletion of a pyruvate carboxylase gene, the overexpression of a phosphoenolpyruvate carboxykinase combined with the overexpression of an oxaloacetate decarboxylase and the overexpression of a malate dehydrogenase combined with the deletion of a pyruvate carboxylase gene, the overexpression of phosphoenolpyruvate synthase combined with the overexpression of an oxaloacetate decarboxylase and the overexpression of a malate dehydrogenase combined with the deletion of a pyruvate carboxylase gene.

In another exemplary embodiment, the cell is genetically modified by different adaptations such as the overexpression of phosphoenolpyruvate synthase combined with the overexpression of a phosphoenolpyruvate carboxykinase combined with the deletion of a pyruvate kinase gene and a phosphoenolpyruvate carboxylase gene, the overexpression of phosphoenolpyruvate synthase combined with the overexpression of an oxaloacetate decarboxylase combined with the deletion of a pyruvate kinase gene and a phosphoenolpyruvate carboxylase gene, the overexpression of phosphoenolpyruvate synthase combined with the overexpression of a malate dehydrogenase combined with the deletion of a pyruvate kinase gene and a phosphoenolpyruvate carboxylase gene, the overexpression of a phosphoenolpyruvate carboxykinase combined with the overexpression of an oxaloacetate decarboxylase combined with the deletion of a pyruvate kinase gene and a phosphoenolpyruvate carboxylase gene, the overexpression of a phosphoenolpyruvate carboxykinase combined with the overexpression of a malate dehydrogenase combined with the deletion of a pyruvate kinase gene and a phosphoenolpyruvate carboxylase gene, the overexpression of an oxaloacetate decarboxylase combined with the overexpression of a malate dehydrogenase combined with the deletion of a pyruvate kinase gene and a phosphoenolpyruvate carboxylase gene, the overexpression of a phosphoenolpyruvate synthase combined with the overexpression of a phosphoenolpyruvate carboxykinase and the overexpression of an oxaloacetate decarboxylase combined with the deletion of a pyruvate kinase gene and a phosphoenolpyruvate carboxylase gene, the overexpression of a phosphoenolpyruvate synthase combined with the overexpression of a phosphoenolpyruvate carboxykinase and the overexpression of a malate dehydrogenase combined with the deletion of a pyruvate kinase gene and a phosphoenolpyruvate carboxylase gene, the overexpression of a phosphoenolpyruvate synthase combined with the overexpression of a phosphoenolpyruvate carboxykinase and the overexpression of an oxaloacetate decarboxylase and the overexpression of a malate dehydrogenase combined with the deletion of a pyruvate kinase gene and a phosphoenolpyruvate carboxylase gene, the overexpression of a phosphoenolpyruvate carboxykinase combined with the overexpression of an oxaloacetate decarboxylase and the overexpression of a malate dehydrogenase combined with the deletion of a pyruvate kinase gene and a phosphoenolpyruvate carboxylase gene, the overexpression of a phosphoenolpyruvate synthase combined with the overexpression of an oxaloacetate decarboxylase and the overexpression of a malate dehydrogenase combined with the deletion of a pyruvate kinase gene and a phosphoenolpyruvate carboxylase gene.

In another exemplary embodiment, the cell is genetically modified by different adaptations such as the overexpression of phosphoenolpyruvate synthase combined with the overexpression of a phosphoenolpyruvate carboxykinase combined with the deletion of a pyruvate kinase gene and a pyruvate carboxylase gene and a phosphoenolpyruvate carboxylase gene, the overexpression of phosphoenolpyruvate synthase combined with the overexpression of an oxaloacetate decarboxylase combined with the deletion of a pyruvate kinase gene and a pyruvate carboxylase gene and a phosphoenolpyruvate carboxylase gene, the overexpression of phosphoenolpyruvate synthase combined with the overexpression of a malate dehydrogenase combined with the deletion of a pyruvate kinase gene and a pyruvate carboxylase gene and a phosphoenolpyruvate carboxylase gene, the overexpression of a phosphoenolpyruvate carboxykinase combined with the overexpression of an oxaloacetate decarboxylase combined with the deletion of a pyruvate kinase gene and a pyruvate carboxylase gene and a phosphoenolpyruvate carboxylase gene, the overexpression of a phosphoenolpyruvate carboxykinase combined with the overexpression of a malate dehydrogenase combined with the deletion of a pyruvate kinase gene and a pyruvate carboxylase gene and a phosphoenolpyruvate carboxylase gene, the overexpression of an oxaloacetate decarboxylase combined with the overexpression of a malate dehydrogenase combined with the deletion of a pyruvate kinase gene and a pyruvate carboxylase gene and a phosphoenolpyruvate carboxylase gene, the overexpression of phosphoenolpyruvate synthase combined with the overexpression of a phosphoenolpyruvate carboxykinase and the overexpression of an oxaloacetate decarboxylase combined with the deletion of a pyruvate kinase gene and a pyruvate carboxylase gene and a phosphoenolpyruvate carboxylase gene, the overexpression of phosphoenolpyruvate synthase combined with the overexpression of a phosphoenolpyruvate carboxykinase and the overexpression of a malate dehydrogenase combined with the deletion of a pyruvate kinase gene and a pyruvate carboxylase gene and a phosphoenolpyruvate carboxylase gene, the overexpression of phosphoenolpyruvate synthase combined with the overexpression of a phosphoenolpyruvate carboxykinase and the overexpression of an oxaloacetate decarboxylase and the overexpression of a malate dehydrogenase combined with the deletion of a pyruvate kinase gene and pyruvate carboxylase gene and a phosphoenolpyruvate carboxylase gene, the overexpression of a phosphoenolpyruvate carboxykinase combined with the overexpression of an oxaloacetate decarboxylase and the overexpression of a malate dehydrogenase combined with the deletion of a pyruvate kinase gene and a pyruvate carboxylase gene and a phosphoenolpyruvate carboxylase gene, the overexpression of phosphoenolpyruvate synthase combined with the overexpression of an oxaloacetate decarboxylase and the overexpression of a malate dehydrogenase combined with the deletion of a pyruvate kinase gene and a pyruvate carboxylase gene and a phosphoenolpyruvate carboxylase gene.

According to another preferred embodiment of the method and/or cell of the disclosure, the cell comprises a modification for reduced production of acetate compared to a non-modified progenitor. The modification can be any one or more chosen from the group comprising overexpression of an acetyl-coenzyme A synthetase, a full or partial knock-out or rendered less functional pyruvate dehydrogenase and a full or partial knock-out or rendered less functional lactate dehydrogenase.

In a further embodiment of the method and/or cell of the disclosure, the cell is modified in the expression or activity of at least one acetyl-coenzyme A synthetase like, e.g., acs from *E. coli, S. cerevisiae, H. sapiens, M. musculus*. In a preferred embodiment, the acetyl-coenzyme A synthetase is an endogenous protein of the cell with a modified expression or activity, preferably the endogenous acetyl-coenzyme A synthetase is overexpressed; alternatively, the acetyl-coenzyme A synthetase is a heterologous protein that is heterogeneously introduced and expressed in the cell, preferably overexpressed. The endogenous acetyl-coenzyme A synthetase can have a modified expression in the cell which also expresses a heterologous acetyl-coenzyme A synthetase. In a more preferred embodiment, the cell is modified in the expression or activity of the acetyl-coenzyme A synthetase acs from *E. coli* (UniProt ID P27550). In another and/or additional preferred embodiment, the cell is modified in the expression or activity of a functional homolog, variant or derivative of acs from *E. coli* (UniProt ID P27550) having at least 80% overall sequence identity to the full-length of the polypeptide from *E. coli* (UniProt ID P27550) and having acetyl-coenzyme A synthetase activity.

In an alternative and/or additional further embodiment of the method and/or cell of the disclosure, the cell is modified in the expression or activity of at least one pyruvate dehydrogenase like, e.g., from *E. coli, S. cerevisiae, H. sapiens* and *R. norvegicus*. In a preferred embodiment, the cell has been modified to have at least one partially or fully knocked out or mutated pyruvate dehydrogenase encoding gene by means generally known by the person skilled in the art resulting in at least one protein with less functional or being disabled for pyruvate dehydrogenase activity. In a more preferred embodiment, the cell has a full knock-out in the poxB encoding gene resulting in a cell lacking pyruvate dehydrogenase activity.

In an alternative and/or additional further embodiment of the method and/or cell of the disclosure, the cell is modified in the expression or activity of at least one lactate dehydrogenase like, e.g., from *E. coli, S. cerevisiae, H. sapiens* and *R. norvegicus*. In a preferred embodiment, the cell has been modified to have at least one partially or fully knocked out or mutated lactate dehydrogenase encoding gene by means generally known by the person skilled in the art resulting in at least one protein with less functional or being disabled for lactate dehydrogenase activity. In a more preferred embodiment, the cell has a full knock-out in the ldhA encoding gene resulting in a cell lacking lactate dehydrogenase activity.

According to another preferred embodiment of the method and/or cell of the disclosure, the cell comprises a lower or reduced expression and/or abolished, impaired, reduced or delayed activity of any one or more of the proteins comprising beta-galactosidase, galactoside 0-acetyltransferase, N-acetylglucosamine-6-phosphate deacetylase, glucosamine-6-phosphate deaminase, N-acetylglucosamine repressor, ribonucleotide monophosphatase, EIICBA-Nag, UDP-glucose:undecaprenyl-phosphate glucose-1-phosphate transferase, L-fuculokinase, L-fucose isomerase, N-acetylneuraminate lyase, N-acetylmannosamine kinase, N-acetylmannosamine-6-phosphate 2-epimerase, EIIAB-Man, EIIC-Man, EIID-Man, ushA, galactose-1-phosphate uridylyltransferase, glucose-1-phosphate adenylyltransferase, glucose-1-phosphatase, ATP-dependent 6-phosphofructokinase isozyme 1, ATP-dependent 6-phosphofructokinase isozyme 2, glucose-6-phosphate isomerase, aerobic respiration control protein, transcriptional repressor IclR, lon protease, glucose-specific translocating phosphotransferase enzyme IIBC component ptsG, glucose-specific translocating phosphotransferase (PTS) enzyme IIBC component malX, enzyme IIAGlc, beta-glucoside specific PTS enzyme II, fructose-specific PTS multiphosphoryl transfer protein FruA and FruB, ethanol dehydrogenase aldehyde dehydrogenase, pyruvate-formate lyase, acetate kinase, phosphoacyltransferase, phosphate acetyltransferase, pyruvate decarboxylase compared to a non-modified progenitor.

According to another preferred embodiment of the method and/or cell of the disclosure, the cell comprises a catabolic pathway for selected mono-, di- or oligosaccharides which is at least partially inactivated, the mono-, di-, or oligosaccharides being involved in and/or required for the production of any one of the oligosaccharides from the mixture.

Another embodiment of the disclosure provides for a method and a cell wherein a mixture comprising at least three different neutral non-fucosylated oligosaccharides is produced in and/or by a fungal, yeast, bacterial, insect, animal, plant and protozoan cell as described herein. The cell is chosen from the list comprising a bacterium, a yeast, a protozoan or a fungus, or, refers to a plant or animal cell. The latter bacterium preferably belongs to the phylum of the Proteobacteria or the phylum of the Firmicutes or the phylum of the Cyanobacteria or the phylum *Deinococcus-Thermus*. The latter bacterium belonging to the phylum Proteobacteria belongs preferably to the family Enterobacteriaceae, preferably to the species *Escherichia coli*. The latter bacterium preferably relates to any strain belonging to the species *Escherichia coli* such as but not limited to *Escherichia coli* B, *Escherichia coli* C, *Escherichia coli* W, *Escherichia coli* K12, *Escherichia coli* Nissle. More specifically, the latter term relates to cultivated *Escherichia coli* strains—designated as *E. coli* K12 strains—which are well-adapted to the laboratory environment, and, unlike wild type strains, have lost their ability to thrive in the intestine. Well-known examples of the *E. coli* K12 strains are K12 Wild type, W3110, MG1655, M182, MC1000, MC1060, MC1061, MC4100, JM101, NZN111 and AA200. Hence, the disclosure specifically relates to a mutated and/or transformed *Escherichia coli* cell or strain as indicated above wherein the *E. coli* strain is a K12 strain. More preferably, the *Escherichia coli* K12 strain is *E. coli* MG1655. The latter bacterium belonging to the phylum Firmicutes belongs preferably to the Bacilli, preferably Lactobacilliales, with members such as *Lactobacillus lactis, Leuconostoc mesenteroides*, or Bacillales with members such as from the genus *Bacillus*, such as *Bacillus subtilis* or, *B. amyloliquefaciens*. The latter Bacterium belonging to the phylum Actinobacteria, preferably belonging to the family of the Corynebacteriaceae, with members *Corynebacterium glutamicum* or *C. afermentans*, or belonging to the family of the Streptomycetaceae with members *Streptomyces griseus* or *S. fradiae*. The latter yeast preferably belongs to the phylum of the Ascomycota or the phylum of the Basidiomycota or the phylum of the Deuteromycota or the phylum of the Zygomycetes. The latter yeast belongs preferably to the genus *Saccharomyces* (with members like, e.g., *Saccharomyces cerevisiae, S. bayanus, S. boulardii*), *Pichia* (with members like, e.g., *Pichia pastoris, P. anomala, P. kluyveri*), Komagataella, *Hansenula, Kluyveromyces* (with members like, e.g., *Kluyveromyces lactis, K marxianus, K thermotolerans*), *Debaromyces, Yarrowia* (like, e.g., *Yarrowia lipolytica*) or *Starmerella* (like, e.g., *Starmerella bombicola*). The latter yeast is preferably selected from *Pichia pastoris, Yarrowia hpolitica, Saccharomyces cerevisiae* and *Kluyveromyces lactis*. The latter fungus belongs preferably to the genus *Rhizopus, Dictyostelium, Penicillium, Mucor* or *Aspergillus*.

Plant cells include cells of flowering and non-flowering plants, as well as algal cells, for example *Chlamydomonas, Chlorella*, etc. Preferably, the plant is a tobacco, alfalfa, rice, tomato, cotton, rapeseed, soy, maize or corn plant. The latter animal cell is preferably derived from non-human mammals (e.g., cattle, buffalo, pig, sheep, mouse, rat), birds (e.g., chicken, duck, ostrich, turkey, pheasant), fish (e.g., swordfish, salmon, tuna, sea bass, trout, catfish), invertebrates (e.g., lobster, crab, shrimp, clams, oyster, mussel, sea urchin), reptiles (e.g., snake, alligator, turtle), amphibians (e.g., frogs) or insects (e.g., fly, nematode) or is a genetically modified cell line derived from human cells excluding embryonic stem cells. Both human and non-human mammalian cells are preferably chosen from the list comprising an epithelial cell like, e.g., a mammary epithelial cell, an embryonic kidney cell (e.g., HEK293 or HEK 293T cell), a fibroblast cell, a COS cell, a Chinese hamster ovary (CHO) cell, a murine myeloma cell like, e.g., an N20, SP2/0 or YB2/0 cell, an NIH-3T3 cell, a non-mammary adult stem cell or derivatives thereof such as described in WO21067641. The latter insect cell is preferably derived from *Spodoptera frugiperda* like, e.g., Sf9 or Sf21 cells, *Bombyx mori, Mamestra brassicae, Trichoplusia ni* like, e.g., BTI-TN-5B1-4 cells or *Drosophila melanogaster* like, e.g., *Drosophila* S2 cells. The latter protozoan cell preferably is a *Leishmania tarentolae* cell.

In a preferred embodiment of the method and/or cell of the disclosure, the cell is a viable Gram-negative bacterium that comprises a reduced or abolished synthesis of poly-N-acetyl-glucosamine (PNAG), Enterobacterial Common Antigen (ECA), cellulose, colanic acid, core oligosaccharides, Osmoregulated Periplasmic Glucans (OPG), Glucosylglycerol, glycan, and/or trehalose compared to a non-modified progenitor.

In a more preferred embodiment of the method and/or cell, the reduced or abolished synthesis of poly-N-acetyl-glucosamine (PNAG), Enterobacterial Common Antigen (ECA), cellulose, colanic acid, core oligosaccharides, Osmoregulated Periplasmic Glucans (OPG), Glucosylglycerol, glycan, and/or trehalose is provided by a mutation in any one or more glycosyltransferases involved in the synthesis of any one of the poly-N-acetyl-glucosamine (PNAG), Enterobacterial Common Antigen (ECA), cellulose, colanic acid, core oligosaccharides, Osmoregulated Periplasmic Glucans (OPG), Glucosylglycerol, glycan, and/or trehalose, wherein the mutation provides for a deletion or lower expression of any one of the glycosyltransferases. The glycosyltransferases comprise glycosyltransferase genes encoding poly-N-acetyl-D-glucosamine synthase subunits, UDP-N-acetylglucosamine-undecaprenyl-phosphate N-acetylglucosaminephosphotransferase, Fuc4NAc (4-acetamido-4,6-dideoxy-D-galactose) transferase, UDP-N-acetyl-D-mannosaminuronic acid transferase, the glycosyltransferase genes encoding the cellulose synthase catalytic subunits, the cellulose biosynthesis protein, colanic acid biosynthesis glucuronosyltransferase, colanic acid biosynthesis galactosyltransferase, colanic acid biosynthesis fucosyltransferase, UDP-glucose:undecaprenyl-phosphate glucose-1-phosphate transferase, putative colanic biosynthesis glycosyl transferase, UDP-glucuronate:LPS(HepIII) glycosyltransferase, ADP-heptose-LPS heptosyltransferase 2, ADP-heptose:LPS heptosyltransferase 1, putative ADP-heptose:LPS heptosyltransferase 4, lipopolysaccharide core biosynthesis protein, UDP-glucose:(glucosyl)LPS α-1,2-glucosyltransferase, UDP-D-glucose: (glucosyl)LPS α-1,3-glucosyltransferase, UDP-D-galactose: (glucosyl) lipopolysaccharide-1,6-D-galactosyltransferase, lipopolysaccharide glucosyltransferase I, lipopolysaccharide core heptosyltransferase 3, β-1,6-galactofuranosyltransferase, undecaprenyl-phosphate 4-deoxy-4-formamido-L-arabinose transferase, lipid IVA 4-amino-4-deoxy-L-arabinosyltransferase, bactoprenol glucosyl transferase, putative family 2 glycosyltransferase, the osmoregulated periplasmic glucans (OPG) biosynthesis protein G, OPG biosynthesis protein H, glucosylglycerate phosphorylase, glycogen synthase, 1,4-α-glucan branching enzyme, 4-α-glucanotransferase and trehalose-6-phosphate synthase. In an exemplary embodiment, the cell is mutated in any one or more of the glycosyltransferases comprising pgaC, pgaD, rfe, rffT, rffM, bcsA, bcsB, bcsC, wcaA, wcaC, wcaE, wcaI, wcaJ, wcaL, waaH, waaF, waaC, waaU, waaZ, waaJ, waaO, waaB, waaS, waaG, waaQ, wbbI, arnC, arnT, yfdH, wbbK, opgG, opgH, ycjM, glgA, glgB, malQ, otsA and yaiP, wherein the mutation provides for a deletion or lower expression of any one of the glycosyltransferases.

In an alternative and/or additional preferred embodiment of the method and/or cell, the reduced or abolished synthesis of poly-N-acetyl-glucosamine (PNAG) is provided by overexpression of a carbon storage regulator encoding gene, deletion of a Na+/H+ antiporter regulator encoding gene and/or deletion of the sensor histidine kinase encoding gene.

The microorganism or cell as used herein is capable to grow on a monosaccharide, disaccharide, oligosaccharide, polysaccharide, polyol, glycerol, a complex medium including molasses, corn steep liquor, peptone, tryptone, yeast extract or a mixture thereof like, e.g., a mixed feedstock, preferably a mixed monosaccharide feedstock like, e.g., hydrolyzed sucrose, as the main carbon source. With the term "complex medium" is meant a medium for which the exact constitution is not determined. With the term main is meant the most important carbon source for the bioproducts of interest, biomass formation, carbon dioxide and/or by-products formation (such as acids and/or alcohols, such as acetate, lactate, and/or ethanol), i.e., 20, 30, 40, 50, 60, 70, 75, 80, 85, 90, 95, 98, 99% of all the required carbon is derived from the above-indicated carbon source. In one embodiment of the disclosure, the carbon source is the sole carbon source for the organism, i.e., 100% of all the required carbon is derived from the above-indicated carbon source. Common main carbon sources comprise but are not limited to glucose, glycerol, fructose, maltose, lactose, arabinose, malto-oligosaccharides, maltotriose, sorbitol, xylose, rhamnose, sucrose, galactose, mannose, methanol, ethanol, trehalose, starch, cellulose, hemi-cellulose, molasses, corn-steep liquor, high-fructose syrup, acetate, citrate, lactate and pyruvate. With the term complex medium is meant a medium for which the exact constitution is not determined. Examples are molasses, corn steep liquor, peptone, tryptone or yeast extract.

In a further preferred embodiment, the microorganism or cell described herein is using a split metabolism having a production pathway and a biomass pathway as described in WO2012/007481, which is herein incorporated by reference. The organism can, for example, be genetically modified to accumulate fructose-6-phosphate by altering the genes selected from the phosphoglucoisomerase gene, phosphofructokinase gene, fructose-6-phosphate aldolase gene, fructose isomerase gene, and/or fructose:PEP phosphotransferase gene.

According to another embodiment of the method of the disclosure, the conditions permissive to produce the oligosaccharides in the mixture comprise the use of a culture medium to cultivate a cell of disclosure for the production of the oligosaccharide mixture wherein the culture medium lacks any precursor and/or acceptor for the production of any one of the oligosaccharides and is combined with a further addition to the culture medium of at least one precursor and/or acceptor feed for the production of any one of the oligosaccharides, preferably for the production of all of the oligosaccharides in the mixture.

In a preferred embodiment, the method for the production of an oligosaccharide mixture as described herein comprises at least one of the following steps:
i) Use of a culture medium comprising at least one precursor and/or acceptor;
ii) Adding to the culture medium in a reactor at least one precursor and/or acceptor feed wherein the total reactor volume ranges from 250 mL (milliliter) to 10,000 m3 (cubic meter), preferably in a continuous manner, and preferably so that the final volume of the culture medium is not more than three-fold, preferably not more than two-fold, more preferably less than two-fold of the volume of the culture medium before the addition of the precursor and/or acceptor feed;
iii) Adding to the culture medium in a reactor at least one precursor and/or acceptor feed wherein the total reactor volume ranges from 250 mL (milliliter) to 10,000 m3 (cubic meter), preferably in a continuous manner, and preferably so that the final volume of the culture medium is not more than three-fold, preferably not more than two-fold, more preferably less than two-fold of the volume of the culture medium before the addition of the precursor and/or acceptor feed and wherein preferably, the pH of the precursor and/or acceptor feed is set between 3 and 7 and wherein preferably, the temperature of the precursor and/or acceptor feed is kept between 20° C. and 80° C.;
iv) Adding at least one precursor and/or acceptor feed in a continuous manner to the culture medium over the course of 1 day, 2 days, 3 days, 4 days, 5 days by means of a feeding solution;

v) Adding at least one precursor and/or acceptor feed in a continuous manner to the culture medium over the course of 1 day, 2 days, 3 days, 4 days, 5 days by means of a feeding solution and wherein preferably, the pH of the feeding solution is set between 3 and 7 and wherein preferably, the temperature of the feeding solution is kept between 20° C. and 80° C.;

the method resulting in any one of the oligosaccharides with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final cultivation.

In another and/or additional preferred embodiment, the method for the production of an oligosaccharide mixture as described herein comprises at least one of the following steps:

i) Use of a culture medium comprising at least 50, more preferably at least 75, more preferably at least 100, more preferably at least 120, more preferably at least 150 gram of lactose per liter of initial reactor volume wherein the reactor volume ranges from 250 mL to 10,000 m3 (cubic meter);

ii) Adding to the culture medium at least one precursor and/or acceptor in one pulse or in a discontinuous (pulsed) manner wherein the total reactor volume ranges from 250 mL (milliliter) to 10,000 m3 (cubic meter), preferably so that the final volume of the culture medium is not more than three-fold, preferably not more than two-fold, more preferably less than two-fold of the volume of the culture medium before the addition of the precursor and/or acceptor feed pulse(s);

iii) Adding to the culture medium in a reactor at least one precursor and/or acceptor feed in one pulse or in a discontinuous (pulsed) manner wherein the total reactor volume ranges from 250 mL (milliliter) to 10,000 m3 (cubic meter), preferably so that the final volume of the culture medium is not more than three-fold, preferably not more than two-fold, more preferably less than 2-fold of the volume of the culture medium before the addition of the precursor and/or acceptor feed pulse(s) and wherein preferably, the pH of the precursor and/or acceptor feed pulse(s) is set between 3 and 7 and wherein preferably, the temperature of the precursor and/or acceptor feed pulse(s) is kept between 20° C. and 80° C.;

iv) Adding at least one precursor and/or acceptor feed in a discontinuous (pulsed) manner to the culture medium over the course of 5 minutes, 10 minutes, 30 minutes, 1 hour, 2 hours, 4 hours, 10 hours, 12 hours, 1 day, 2 days, 3 days, 4 days, 5 days by means of a feeding solution;

v) Adding at least one precursor and/or acceptor feed in a discontinuous (pulsed) manner to the culture medium over the course of 5 minutes, 10 minutes, 30 minutes, 1 hour, 2 hours, 4 hours, 10 hours, 12 hours, 1 day, 2 days, 3 days, 4 days, 5 days by means of a feeding solution and wherein preferably, the pH of the feeding solution is set between 3 and 7 and wherein preferably, the temperature of the feeding solution is kept between 20° C. and 80° C.;

the method resulting in any one of the oligosaccharides with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final cultivation.

In a further, more preferred embodiment, the method for the production of an oligosaccharide mixture as described herein comprises at least one of the following steps:

i) Use of a culture medium comprising at least 50, more preferably at least 75, more preferably at least 100, more preferably at least 120, more preferably at least 150 gram of lactose per liter of initial reactor volume wherein the reactor volume ranges from 250 mL to 10,000 $m^3$ (cubic meter);

ii) Adding to the culture medium a lactose feed comprising at least 50, more preferably at least 75, more preferably at least 100, more preferably at least 120, more preferably at least 150 gram of lactose per liter of initial reactor volume wherein the total reactor volume ranges from 250 mL (milliliter) to 10,000 $m^3$ (cubic meter), preferably in a continuous manner, and preferably so that the final volume of the culture medium is not more than three-fold, preferably not more than two-fold, more preferably less than 2-fold of the volume of the culture medium before the addition of the lactose feed;

iii) Adding to the culture medium a lactose feed comprising at least 50, more preferably at least 75, more preferably at least 100, more preferably at least 120, more preferably at least 150 gram of lactose per liter of initial reactor volume wherein the reactor volume ranges from 250 mL to 10,000 $m^3$ (cubic meter), preferably in a continuous manner, and preferably so that the final volume of the culture medium is not more than three-fold, preferably not more than two-fold, more preferably less than 2-fold of the volume of the culture medium before the addition of the lactose feed and wherein preferably the pH of the lactose feed is set between 3 and 7 and wherein preferably the temperature of the lactose feed is kept between 20° C. and 80° C.;

iv) Adding a lactose feed in a continuous manner to the culture medium over the course of 1 day, 2 days, 3 days, 4 days, 5 days by means of a feeding solution;

v) Adding a lactose feed in a continuous manner to the culture medium over the course of 1 day, 2 days, 3 days, 4 days, 5 days by means of a feeding solution and wherein the concentration of the lactose feeding solution is 50 g/L, preferably 75 g/L, more preferably 100 g/L, more preferably 125 g/L, more preferably 150 g/L, more preferably 175 g/L, more preferably 200 g/L, more preferably 225 g/L, more preferably 250 g/L, more preferably 275 g/L, more preferably 300 g/L, more preferably 325 g/L, more preferably 350 g/L, more preferably 375 g/L, more preferably, 400 g/L, more preferably 450 g/L, more preferably 500 g/L, even more preferably, 550 g/L, most preferably 600 g/L; and wherein preferably the pH of the feeding solution is set between 3 and 7 and wherein preferably the temperature of the feeding solution is kept between 20° C. and 80° C.;

the method resulting in any one of the oligosaccharides with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final cultivation.

Preferably, the lactose feed is accomplished by adding lactose from the beginning of the cultivation at a concentration of at least 5 mM, preferably in a concentration of 30, 40, 50, 60, 70, 80, 90, 100, 150 mM, more preferably at a concentration >300 mM.

In another embodiment the lactose feed is accomplished by adding lactose to the culture medium in a concentration, such that throughout the production phase of the cultivation a lactose concentration of at least 5 mM, preferably 10 mM or 30 mM is obtained.

In a further embodiment of the methods described herein the host cells are cultivated for at least about 60, 80, 100, or about 120 hours or in a continuous manner.

In a preferred embodiment, a carbon source is provided, preferably sucrose, in the culture medium for 3 or more days, preferably up to 7 days; and/or provided, in the culture medium, at least 100, advantageously at least 105, more advantageously at least 110, even more advantageously at least 120 grams of sucrose per liter of initial culture volume in a continuous manner, so that the final volume of the culture medium is not more than three-fold, advantageously not more than two-fold, more advantageously less than two-fold of the volume of the culturing medium before the culturing.

Preferably, when performing the method as described herein, a first phase of exponential cell growth is provided by adding a carbon source, preferably glucose or sucrose, to the culture medium before the precursor, preferably lactose, is added to the cultivation in a second phase.

In another preferred embodiment of the method of disclosure, a first phase of exponential cell growth is provided by adding a carbon-based substrate, preferably glucose or sucrose, to the culture medium comprising a precursor, preferably lactose, followed by a second phase wherein only a carbon-based substrate, preferably glucose or sucrose, is added to the cultivation.

In another preferred embodiment of the method of disclosure, a first phase of exponential cell growth is provided by adding a carbon-based substrate, preferably glucose or sucrose, to the culture medium comprising a precursor, preferably lactose, followed by a second phase wherein a carbon-based substrate, preferably glucose or sucrose, and a precursor, preferably lactose, are added to the cultivation.

In an alternative preferable embodiment, in the method as described herein, the precursor is added already in the first phase of exponential growth together with the carbon-based substrate.

In another preferred embodiment of the method, the culture medium contains at least one precursor selected from the group comprising lactose, galactose, fucose, GlcNAc, GalNAc, lacto-N-biose (LNB) and N-acetyllactosamine (LacNAc).

According to the disclosure, the method as described herein preferably comprises a step of separating of any one or more of the oligosaccharides, preferably all of the oligosaccharides, from the cultivation.

The terms "separating from the cultivation" means harvesting, collecting, or retrieving any one of the oligosaccharides, preferably all of the oligosaccharides, from the cell and/or the medium of its growth.

Any one of the oligosaccharides can be separated in a conventional manner from the aqueous culture medium, in which the cell was grown. In case the oligosaccharide is still present in the cells producing the oligosaccharide mixture, conventional manners to free or to extract the oligosaccharide out of the cells can be used, such as cell destruction using high pH, heat shock, sonication, French press, homogenization, enzymatic hydrolysis, chemical hydrolysis, solvent hydrolysis, detergent, hydrolysis, etc. The culture medium and/or cell extract together and separately can then be further used for separating the oligosaccharide. This preferably involves clarifying the oligosaccharide containing mixture to remove suspended particulates and contaminants, particularly cells, cell components, insoluble metabolites and debris produced by culturing the genetically modified cell. In this step, the oligosaccharide containing mixture can be clarified in a conventional manner. Preferably, the oligosaccharide containing mixture is clarified by centrifugation, flocculation, decantation and/or filtration. Another step of separating the oligosaccharide from the oligosaccharide containing mixture preferably involves removing substantially all the proteins, as well as peptides, amino acids, RNA and DNA and any endotoxins and glycolipids that could interfere with the subsequent separation step, from the oligosaccharide containing mixture, preferably after it has been clarified. In this step, proteins and related impurities can be removed from the oligosaccharide containing mixture in a conventional manner. Preferably, proteins, salts, by-products, color, endotoxins and other related impurities are removed from the oligosaccharide containing mixture by ultrafiltration, nanofiltration, two-phase partitioning, reverse osmosis, microfiltration, activated charcoal or carbon treatment, treatment with non-ionic surfactants, enzymatic digestion, tangential flow high-performance filtration, tangential flow ultrafiltration, electrophoresis (e.g., using slab-polyacrylamide or sodium dodecyl sulphate-polyacrylamide gel electrophoresis (PAGE)), affinity chromatography (using affinity ligands including, e.g., DEAE-Sepharose, poly-L-lysine and polymyxin-B, endotoxin-selective adsorber matrices), ion exchange chromatography (such as but not limited to cation exchange, anion exchange, mixed bed ion exchange, inside-out ligand attachment), hydrophobic interaction chromatography and/or gel filtration (i.e., size exclusion chromatography), particularly by chromatography, more particularly by ion exchange chromatography or hydrophobic interaction chromatography or ligand exchange chromatography. With the exception of size exclusion chromatography, proteins and related impurities are retained by a chromatography medium or a selected membrane, the oligosaccharide remains in the oligosaccharide containing mixture.

In a further preferred embodiment, the methods as described herein also provide for a further purification of any one or more of the neutral non-fucosylated oligosaccharide(s) from the oligosaccharide mixture. A further purification of the oligosaccharide(s) may be accomplished, for example, by use of (activated) charcoal or carbon, nanofiltration, ultrafiltration, electrophoresis, enzymatic treatment or ion exchange to remove any remaining DNA, protein, LPS, endotoxins, or other impurity. Alcohols, such as ethanol, and aqueous alcohol mixtures can also be used. Another purification step is accomplished by crystallization, evaporation or precipitation of the product. Another purification step is to dry, e.g., spray dry, lyophilize, spray freeze dry, freeze spray dry, band dry, belt dry, vacuum band dry, vacuum belt dry, drum dry, roller dry, vacuum drum dry or vacuum roller dry the produced oligosaccharide(s), preferably the produced neutral non-fucosylated oligosaccharide(s).

In an exemplary embodiment, the separation and purification of at least one, preferably all, of the produced neutral non-fucosylated oligosaccharides is made in a process, comprising the following steps in any order:

a) contacting the cultivation or a clarified version thereof with a nanofiltration membrane with a molecular weight cut-off (MWCO) of 600-3500 Da ensuring the retention of produced oligosaccharide(s) and allowing at least a part of the proteins, salts, by-products, color and other related impurities to pass, b) conducting a diafiltration process on the retentate from step a), using the membrane, with an aqueous solution of an inorganic electrolyte, followed by optional diafiltration with pure water to remove excess of the electrolyte, and c) collecting the retentate enriched in the oligosaccharide(s) in the form of a salt from the cation of the electrolyte.

In an alternative exemplary embodiment, the separation and purification of at least one, preferably all, of the produced neutral non-fucosylated oligosaccharides is made in a process, comprising the following steps in any order: subjecting the cultivation or a clarified version thereof to two membrane filtration steps using different membranes, wherein one membrane has a molecular weight cut-off of between about 300 to about 500 Dalton, and the other membrane as a molecular weight cut-off of between about 600 to about 800 Dalton.

In an alternative exemplary embodiment, the separation and purification of at least one, preferably all, of the produced neutral non-fucosylated oligosaccharides is made in a process, comprising the following steps in any order comprising the step of treating the cultivation or a clarified version thereof with a strong cation exchange resin in H+-form and a weak anion exchange resin in free base form.

In an alternative exemplary embodiment, the separation and purification of at least one, preferably all, of the produced neutral non-fucosylated oligosaccharides is made in the following way. The cultivation comprising the produced oligosaccharide, biomass, medium components and contaminants is applied to the following purification steps:

i) separation of biomass from the cultivation, ii) cationic ion exchanger treatment for the removal of positively charged material, iii) anionic ion exchanger treatment for the removal of negatively charged material, iv) nanofiltration step and/or electrodialysis step, wherein a purified solution comprising the produced oligosaccharide(s) at a purity of greater than or equal to 80 percent is provided. Optionally the purified solution is dried by any one or more drying steps chosen from the list comprising spray drying, lyophilization, spray freeze drying, freeze spray drying, band drying, belt drying, vacuum band drying, vacuum belt drying, drum drying, roller drying, vacuum drum drying and vacuum roller drying.

In an alternative exemplary embodiment, the separation and purification of at least one, preferably all, of the produced neutral non-fucosylated oligosaccharides is made in a process, comprising the following steps in any order: enzymatic treatment of the cultivation; removal of the biomass from the cultivation; ultrafiltration; nanofiltration; and a column chromatography step. Preferably, such column chromatography is a single column or a multiple column. Further preferably the column chromatography step is simulated moving bed chromatography. Such simulated moving bed chromatography preferably comprises i) at least 4 columns, wherein at least one column comprises a weak or strong cation exchange resin; and/or ii) four zones I, II, III and IV with different flow rates; and/or iii) an eluent comprising water; and/or iv) an operating temperature of 15 degrees to 60 degrees centigrade.

In a specific embodiment, the disclosure provides the produced oligosaccharide or oligosaccharide mixture which is dried to powder by any one or more drying steps chosen from the list comprising spray drying, lyophilization, spray freeze drying, freeze spray drying, band drying, belt drying, vacuum band drying, vacuum belt drying, drum drying, roller drying, vacuum drum drying and vacuum roller drying, wherein the dried powder contains <15 percent-wt. of water, preferably <10 percent-wt. of water, more preferably <7 percent-wt. of water, most preferably <5 percent-wt. of water.

In a third aspect, the disclosure provides for the use of a metabolically engineered cell as described herein for the production of a mixture comprising at least three different neutral non-fucosylated oligosaccharides.

For identification of the oligosaccharides in the mixture comprising at least three neutral non-fucosylated different oligosaccharides produced in the cell as described herein, the monomeric building blocks (e.g., the monosaccharide or glycan unit composition), the anomeric configuration of side chains, the presence and location of substituent groups, degree of polymerization/molecular weight and the linkage pattern can be identified by standard methods known in the art, such as, e.g., methylation analysis, reductive cleavage, hydrolysis, GC-MS (gas chromatography-mass spectrometry), MALDI-MS (Matrix-assisted laser desorption/ionization-mass spectrometry), ESI-MS (Electrospray ionization-mass spectrometry), HPLC (High-Performance Liquid chromatography with ultraviolet or refractive index detection), HPAEC-PAD (High-Performance Anion-Exchange chromatography with Pulsed Amperometric Detection), CE (capillary electrophoresis), IR (infrared)/Raman spectroscopy, and NMR (Nuclear magnetic resonance) spectroscopy techniques. The crystal structure can be solved using, e.g., solid-state NMR, FT-IR (Fourier transform infrared spectroscopy), and WAXS (wide-angle X-ray scattering). The degree of polymerization (DP), the DP distribution, and polydispersity can be determined by, e.g., viscosimetry and SEC (SEC-HPLC, high performance size-exclusion chromatography). To identify the monomeric components of the saccharide methods such as, e.g., acid-catalyzed hydrolysis, HPLC (high performance liquid chromatography) or GLC (gas-liquid chromatography) (after conversion to alditol acetates) may be used. To determine the glycosidic linkages, the saccharide is methylated with methyl iodide and strong base in DMSO, hydrolysis is performed, a reduction to partially methylated alditols is achieved, an acetylation to methylated alditol acetates is performed, and the analysis is carried out by GLC/MS (gas-liquid chromatography coupled with mass spectrometry). To determine the oligosaccharide sequence, a partial depolymerization is carried out using an acid or enzymes to determine the structures. To identify the anomeric configuration, the oligosaccharide is subjected to enzymatic analysis, e.g., it is contacted with an enzyme that is specific for a particular type of linkage, e.g., beta-galactosidase, or alpha-glucosidase, etc., and NMR may be used to analyze the products.

Products Comprising the Oligosaccharide Mixture

In some embodiments, an oligosaccharide mixture produced as described herein is incorporated into a food (e.g., human food or feed), dietary supplement, pharmaceutical ingredient, cosmetic ingredient or medicine. In some embodiments, the oligosaccharide mixture is mixed with one or more ingredients suitable for food, feed, dietary supplement, pharmaceutical ingredient, cosmetic ingredient or medicine.

In some embodiments, the dietary supplement comprises at least one prebiotic ingredient and/or at least one probiotic ingredient.

A "prebiotic" is a substance that promotes growth of microorganisms beneficial to the host, particularly microorganisms in the gastrointestinal tract. In some embodiments, a dietary supplement provides multiple prebiotics, including the oligosaccharide mixture produced and/or purified by a process disclosed in this specification, to promote growth of one or more beneficial microorganisms. Examples of prebiotic ingredients for dietary supplements include other prebiotic molecules (such as HMOs) and plant polysaccharides (such as inulin, pectin, b-glucan and xylooligosaccharide). A "probiotic" product typically contains live microorganisms that replace or add to gastrointestinal microflora, to the benefit of the recipient. Examples of such microorganisms include *Lactobacillus* species (for example, *L. acidophilus* and *L. bulgaricus*), *Bifidobacterium* species (for example, *B. animalis, B. longum* and *B. infantis* (e.g., Bi-26)), and *Saccharomyces boulardii*. In some embodiments, an oligosaccharide mixture produced and/or purified by a process of this specification is orally administered in combination with such microorganism.

Examples of further ingredients for dietary supplements include disaccharides (such as lactose), monosaccharides (such as glucose and galactose), thickeners (such as gum arabic), acidity regulators (such as trisodium citrate), water, skimmed milk, and flavorings.

In some embodiments, the oligosaccharide mixture is incorporated into a human baby food (e.g., infant formula). Infant formula is generally a manufactured food for feeding to infants as a complete or partial substitute for human breast milk. In some embodiments, infant formula is sold as a powder and prepared for bottle- or cup-feeding to an infant by mixing with water. The composition of infant formula is typically designed to be roughly mimic human breast milk. In some embodiments, an oligosaccharide mixture produced and/or purified by a process in this specification is included in infant formula to provide nutritional benefits similar to those provided by the oligosaccharides in human breast milk. In some embodiments, the oligosaccharide mixture is mixed with one or more ingredients of the infant formula. Examples of infant formula ingredients include nonfat milk, carbohydrate sources (e.g., lactose), protein sources (e.g., whey protein concentrate and casein), fat sources (e.g., vegetable oils—such as palm, high oleic safflower oil, rapeseed, coconut and/or sunflower oil; and fish oils), vitamins (such as vitamins A, Bb, Bit, C and D), minerals (such as potassium citrate, calcium citrate, magnesium chloride, sodium chloride, sodium citrate and calcium phosphate) and possibly human milk oligosaccharides (HMOs). Such HMOs may include, for example, DiFL, lacto-N-triose II, LNT, LNnT, lacto-N-fucopentaose I, lacto-N-neofucopentaose, lacto-N-fucopentaose II, lacto-N-fucopentaose III, lacto-N-fucopentaose V, lacto-N-neofucopentaose V, lacto-N-difucohexaose I, lacto-N-difucohexaose II, 6'-galactosyllactose, 3'-galactosyllactose, lacto-N-hexaose and lacto-N-neohexaose.

In some embodiments, the one or more infant formula ingredients comprise nonfat milk, a carbohydrate source, a protein source, a fat source, and/or a vitamin and mineral.

In some embodiments, the one or more infant formula ingredients comprise lactose, whey protein concentrate and/or high oleic safflower oil.

In some embodiments, the oligosaccharide mixture's concentration in the infant formula is approximately the same concentration as the oligosaccharide's concentration generally present in human breast milk. In some embodiments, the concentration of each of the single oligosaccharides in the mixture of oligosaccharides in the infant formula is approximately the same concentration as the concentration of that oligosaccharide generally present in human breast milk.

In some embodiments, the oligosaccharide mixture is incorporated into a feed preparation, wherein the feed is chosen from the list comprising pet food, animal milk replacer, veterinary product, post weaning feed, or creep feed.

Each embodiment disclosed in the context of one aspect of the disclosure, is also disclosed in the context of all other aspects of the disclosure, unless explicitly stated otherwise.

Unless defined otherwise, all technical and scientific terms used herein generally have the same meaning as commonly understood by one of ordinary skill in the art to which this disclosure belongs. Generally, the nomenclature used herein and the laboratory procedures in cell culture, molecular genetics, organic chemistry and nucleic acid chemistry and hybridization described above and below are those well-known and commonly employed in the art. Standard techniques are used for nucleic acid and peptide synthesis. Generally, purification steps are performed according to the manufacturer's specifications.

Further advantages follow from the specific embodiments and the examples. It goes without saying that the above-mentioned features and the features which are still to be explained below can be used not only in the respectively specified combinations, but also in other combinations or on their own, without departing from the scope of the disclosure.

The disclosure relates to following specific embodiments:

1. A metabolically engineered cell producing a mixture of at least three different neutral non-fucosylated oligosaccharides, wherein the cell
    expresses at least two glycosyltransferases, and
    is capable to synthesize one or more nucleotide-sugar(s), wherein the nucleotide-sugar(s) is/are donor(s) for the glycosyltransferases.

2. Cell according to embodiment 1, wherein the cell is modified with gene expression modules, characterized in that the expression from any of the expression modules is either constitutive or is created by a natural inducer.

3. Cell according to any one of embodiments 1 to 2, wherein the oligosaccharide mixture comprises at least three different neutral non-fucosylated oligosaccharides differing in degree of polymerization.

4. Cell according to any one of embodiments 1 and 3, wherein the cell produces four or more different neutral non-fucosylated oligosaccharides.

5. Cell according to any one of embodiments 1 to 4, wherein any one of the glycosyltransferase is chosen from the list comprising galactosyltransferases, glucosyltransferases, mannosyltransferases, N-acetylglucosaminyltransferases, N-acetylgalactosaminyltransferases, N-acetylmannosaminyltransferases, xylosyltransferases, glucosaminyltransferases, rhamnosyltransferases.

6. Cell according to any one of embodiments 1 to 5 wherein the cell is modified in the expression or activity of at least one of the glycosyltransferases.

7. Cell according to any one of embodiments 1 to 6 wherein any one of the glycosyltransferases is an N-acetylglucosaminyltransferase and any one of the donor nucleotide-sugar is UDP-N-acetylglucosamine (UDP-GlcNAc).

8. Cell according to any one of embodiments 1 to 7 wherein any one of the glycosyltransferase is a galactosyltransferase and any one of the donor nucleotide-sugar is UDP-galactose (UDP-Gal).

9. Cell according to any one of embodiments 1 to 8, wherein any one of the nucleotide-sugar is chosen from the list comprising UDP-GlcNAc, UDP-Gal, UDP-N-acetylgalactosamine (UDP-GalNAc), UDP-N-acetylmannosamine (UDP-ManNAc), GDP-mannose (GDP-Man), UDP-glucose (UDP-Glc), GDP-rhamnose, UDP-xylose.

10. Cell according to any one of embodiments 1 to 9, wherein the mixture comprises at least one neutral non-fucosylated oligosaccharide that is galactosylated, glucosylated, xylosylated, mannosylated, contains an N-acetylglucosamine, contains an N-acetylgalactosamine, contains a rhamnose, and/or contains an N-acetylmannosamine.

11. Cell according to any one of embodiments 1 to 10, wherein the oligosaccharide mixture comprises at least one oligosaccharide that comprises an N-acetylglucosamine monosaccharide unit.

12. Cell according to any one of embodiments 1 to 11, wherein the oligosaccharide mixture comprises at least one galactosylated oligosaccharide.

13. Cell according to any one of embodiments 1 to 12, wherein the cell is further genetically modified for
  i) modified expression of an endogenous membrane protein, and/or
  ii) modified activity of an endogenous membrane protein, and/or
  iii) expression of a homologous membrane protein, and/or
  iv) expression of a heterologous membrane protein,
  wherein the membrane protein is involved in the secretion of any one of the neutral non-fucosylated oligosaccharides from the mixture outside the cell.

14. Cell according to any one of embodiments 1 to 13, wherein the cell is further genetically modified for
  i) modified expression of an endogenous membrane protein, and/or
  ii) modified activity of an endogenous membrane protein, and/or
  iii) expression of a homologous membrane protein, and/or
  iv) expression of a heterologous membrane protein,
  wherein the membrane protein is involved in the uptake of a precursor for the synthesis of any one of the neutral non-fucosylated oligosaccharides.

15. Cell according to any one of embodiments 1 to 14, wherein the cell is producing a precursor for the synthesis of any one of the neutral non-fucosylated oligosaccharides.

16. Cell according to any one of embodiments 1 to 15, wherein any one of the neutral non-fucosylated oligosaccharide is a mammalian milk oligosaccharide.

17. Cell according to any one of embodiments 1 to 16, wherein all the neutral non-fucosylated oligosaccharides are mammalian milk oligosaccharides.

18. A method to produce a mixture of at least three different neutral non-fucosylated oligosaccharides by a cell, the method comprising the steps of:
  i) providing a cell expressing at least two glycosyltransferases and capable to synthesize one or more nucleotide-sugar(s), wherein the nucleotide-sugar(s) is/are donor(s) for the glycosyltransferases,
  ii) cultivating the cell under conditions permissive to express the glycosyltransferases and to synthesize the nucleotide-sugars,
  iii) preferably, separating at least one of the neutral non-fucosylated oligosaccharides from the cultivation.

19. Method according to embodiment 18, wherein the cell is a metabolically engineered cell according to any one of embodiments 1 to 17.

20. Method according to any one of embodiments 18 and 19, wherein the oligosaccharide mixture comprises at least three different neutral non-fucosylated oligosaccharides differing in degree of polymerization.

21. Method according to any one of embodiments 18 to 20, wherein the cell produces four or more different neutral non-fucosylated oligosaccharides.

22. Method according to any one of embodiments 18 to 21, wherein any one of the glycosyltransferases is chosen from the list comprising galactosyltransferases, glucosyltransferases, mannosyltransferases, N-acetylglucosaminyltransferases, N-acetylgalactosaminyltransferases, N-acetylmannosaminyltransferases, xylosyltransferases, glucosaminyltransferases, rhamnosyltransferases.

23. Method according to any one of embodiments 18 to 22 wherein any one of the glycosyltransferases is an N-acetylglucosaminyltransferase and any one of the donor nucleotide-sugars is UDP-N-acetylglucosamine (UDP-GlcNAc).

24. Method according to any one of embodiments 18 to 23 wherein any one of the glycosyltransferases is a galactosyltransferase and any one of the donor nucleotide-sugar is UDP-galactose (UDP-Gal).

25. Method according to any one of embodiments 18 to 24, wherein any one of the nucleotide-sugars is chosen from the list comprising UDP-GlcNAc, UDP-Gal, UDP-N-acetylgalactosamine (UDP-GalNAc), UDP-N-acetylmannosamine (UDP-ManNAc), GDP-mannose (GDP-Man), UDP-glucose (UDP-Glc), GDP-rhamnose, UDP-xylose.

26. Method according to any one of embodiments 18 to 25, wherein the oligosaccharide mixture comprises at least one oligosaccharide that comprises an N-acetylglucosamine monosaccharide unit.

27. Method according to any one of embodiments 18 to 26, wherein the oligosaccharide mixture comprises at least one galactosylated oligosaccharide.

28. Method according to any one of embodiments 18 to 27, wherein any one of the neutral non-fucosylated oligosaccharides is galactosylated, glucosylated, xylosylated, mannosylated, contains an N-acetylglucosamine, contains an N-acetylgalactosamine, contains a rhamnose, and/or contains an N-acetylmannosamine.

29. Method according to any one of embodiments 18 to 27, wherein the cell uses at least one precursor for the synthesis of any one or more of the oligosaccharides, preferably the cell uses two or more precursors for the synthesis of any one or more of the oligosaccharides.

30. Method according to any one of embodiments 18 to 29, wherein the cell is producing a precursor for the synthesis of any one of the neutral non-fucosylated oligosaccharides.

31. Method according to any one of embodiments 18 to 30, wherein any one of the neutral non-fucosylated oligosaccharide is a mammalian milk oligosaccharide.

32. Method according to any one of embodiments 18 to 31, wherein all the neutral non-fucosylated oligosaccharides are mammalian milk oligosaccharides.

33. The method according to any one of embodiments 18 to 32, wherein the precursor for the synthesis of any one of the neutral non-fucosylated oligosaccharides is completely converted into any one of the neutral non-fucosylated oligosaccharides.

34. The method according to any one of embodiments 18 to 33, wherein the separation comprises at least one of the following steps: clarification, ultrafiltration, nanofiltration, reverse osmosis, microfiltration, activated charcoal or carbon treatment, tangential flow high-performance filtration, tangential flow ultrafiltration, affinity chromatography, ion exchange chromatography, hydrophobic interaction chromatography and/or gel filtration, ligand exchange chromatography.

35. The method according to any one of embodiments 18 to 34, further comprising purification of any one of the neutral non-fucosylated oligosaccharides from the cell.

36. The method according to any one of embodiments 18 to 35, wherein the purification comprises at least one of the following steps: use of activated charcoal or carbon, use of charcoal, nanofiltration, ultrafiltration or ion exchange, use of alcohols, use of aqueous alcohol mixtures, crystallization, evaporation, precipitation, drying, spray drying or lyophilization.

37. The cell according to any one of embodiments 1 to 17 or method according to any one of embodiments 18 to 36, wherein the cell is selected from the group consisting of microorganism, plant, or animal cells, preferably the microorganism is a bacterium, fungus or a yeast, preferably the plant is a rice, cotton, rapeseed, soy, maize or corn plant, preferably the animal is an insect, fish, bird or non-human mammal, preferably the animal cell is a mammalian cell line.

38. The cell according to any one of embodiments 1 to 17 and 37, or method according to any one of embodiments 18 to 37, wherein the cell is a cell of a bacterium, preferably of an *Escherichia coli* strain, more preferably of an *Escherichia coli* strain which is a K-12 strain, even more preferably the *Escherichia coli* K-12 strain is *E. coli* MG1655.

39. The cell according to any one of embodiments 1 to 17 and 37, or method according to any one of embodiments 18 to 37, wherein the cell is a yeast cell.

40. Use of a cell according to any one of embodiments 1 to 17, 37 to 39, or method according to any one of embodiments 18 to 39 for the production of a mixture of at least three different neutral non-fucosylated oligosaccharides.

Moreover, the disclosure relates to the following preferred specific embodiments:

1. A metabolically engineered cell producing a mixture of at least four different neutral non-fucosylated oligosaccharides, wherein the cell
   is metabolically engineered for the production of the mixture, and
   expresses at least two glycosyltransferases, and
   is capable to synthesize one or more nucleotide-sugar(s), wherein the nucleotide-sugar(s) is/are donor(s) for the glycosyltransferases.

2. Cell according to preferred embodiment 1, wherein the cell is modified with gene expression modules, characterized in that the expression from any of the expression modules is either constitutive or is created by a natural inducer.

3. Cell according to any one of preferred embodiment 1 or 2, wherein the cell comprises multiple copies of the same coding DNA sequence encoding for one protein.

4. Cell according to any one of preferred embodiments 1 to 3, wherein the oligosaccharide mixture comprises at least three different neutral non-fucosylated oligosaccharides differing in degree of polymerization.

5. Cell according to any one of preferred embodiments 1 to 4, wherein the cell produces five or more different neutral non-fucosylated oligosaccharides.

6. Cell according to any one of preferred embodiments 1 to 5, wherein any one of the glycosyltransferase is chosen from the list comprising galactosyltransferases, glucosyltransferases, mannosyltransferases, N-acetylglucosaminyltransferases, N-acetylgalactosaminyltransferase s, N-acetylmannosaminyltransferases, xylosyltransferases, glucosaminyltransferases, rhamnosyltransferases, N-acetylrhamnosyltransferases, UDP-4-amino-4,6-dideoxy-N-acetyl-beta-L-altrosamine transaminases, UDP-N-acetylglucosamine enolpyruvyl transferases and fucosaminyltransferases, preferably, the galactosyltransferase is chosen from the list comprising beta-1,3-galactosyltransferase, N-acetylglucosamine beta-1,3-galactosyltransferase, beta-1,4-galactosyltransferase, N-acetylglucosamine beta-1,4-galactosyltransferase, alpha-1,3-galactosyltransferase and alpha-1,4-galactosyltransferase, preferably, the glucosyltransferase is chosen from the list comprising alpha-glucosyltransferase, beta-1,2-glucosyltransferase, beta-1,3-glucosyltransferase and beta-1,4-glucosyltransferase, preferably, the mannosyltransferase is chosen from the list comprising alpha-1,2-mannosyltransferase, alpha-1,3-mannosyltransferase and alpha-1,6-mannosyltransferase, preferably, the N-acetylglucosaminyltransferase is chosen from the list comprising galactoside beta-1,3-N-acetylglucosaminyltransferase and beta-1,6-N-acetylglucosaminyltransferase, preferably, the N-acetylgalactosaminyltransferase is chosen from the list comprising alpha-1,3-N-acetylgalactosaminyltransferase and beta-1,3-N-acetylgalactosaminyltransferase.

7. Cell according to any one of preferred embodiments 1 to 6, wherein the cell is capable to express, preferably expresses, at least three, more preferably at least four, even more preferably at least five, most preferably at least six glycosyltransferases.

8. Cell according to any one of preferred embodiments 1 to 7 wherein the cell is modified in the expression or activity of at least one of the glycosyltransferases.

9. Cell according to any one of preferred embodiments 1 to 8 wherein any one of the glycosyltransferases is an N-acetylglucosaminyltransferase and any one of the donor nucleotide-sugar is UDP-N-acetylglucosamine (UDP-GlcNAc).

10. Cell according to any one of preferred embodiments 1 to 9 wherein any one of the glycosyltransferase is a galactosyltransferase and any one of the donor nucleotide-sugar is UDP-galactose (UDP-Gal).

11. Cell according to any one of preferred embodiment 1 to 10, wherein the glycosyltransferase is an N-acetylgalactosaminyltransferase and the donor nucleotide-sugar is UDP-N-acetylgalactosamine (UDP-GalNAc).

12. Cell according to any one of preferred embodiment 1 to 11, wherein the glycosyltransferase is an N-acetylmannosaminyltransferase and the donor nucleotide-sugar is UDP-N-acetylmannosamine (UDP-ManNAc).

13. Cell according to any one of preferred embodiments 1 to 12, wherein any one of the nucleotide-sugar is chosen from the list comprising UDP-N-acetylglucosamine (UDP-GlcNAc), UDP-galactose (UDP-Gal), UDP-N-acetylgalactosamine (UDP-GalNAc), UDP-N-acetylmannosamine (UDP-ManNAc), GDP-mannose (GDP-Man), UDP-glucose (UDP-Glc), GDP-rhamnose, UDP-xylose, UDP-2-acetamido-2,6-dideoxy-L-arabino-4-hexulose, UDP-2-acetamido-2,6-dideoxy-L-lyxo-4-hexulose, UDP-N-acetyl-L-rhamnosamine (UDP-L-RhaNAc or UDP-2-acetamido-2,6-dideoxy-L-mannose), dTDP-N-acetylfucosamine, UDP-N-acetylfucosamine (UDP-L-FucNAc or UDP-2-acetamido-2,6-dideoxy-L-galactose), UDP-N-acetyl-L-pneumosamine (UDP-L-PneNAC or UDP-2-acetamido-2,6-dideoxy-L-talose), UDP-N-acetylmuramic acid, UDP-N-acetyl-L-quinovosamine (UDP-L-QuiNAc or UDP-2-acetamido-2,6-dideoxy-L-glucose), GDP-L-quinovose.

14. Cell according to any one of preferred embodiment 1 to 13, wherein the cell expresses one or more polypeptides chosen from the list comprising L-glutamine-D-fructose-6-phosphate aminotransferase, glucosamine-6-phosphate deaminase, phosphoglucosamine mutase, N-acetylglucosamine-6-phosphate deacetylase, N-acylglucosamine 2-epimerase, UDP-N-acetylglucosamine 2-epimerase, N-acetylmannosamine-6-phosphate 2-epimerase, glucosamine 6-phosphate N-acetyltransferase, N-acetylglucosamine-6-phosphate phosphatase, N-acetylmannosamine-6-phosphate phosphatase, N-acetylmannosamine kinase, phosphoacetylglucosamine mutase, N-acetylglucosamine-1-phosphate uridylyltransferase, glucosamine-1-phosphate acetyltransferase, galactose-1-epimerase, galactokinase, glucokinase, galactose-1-phosphate uridylyltransferase, UDP-glucose 4-epimerase, glucose-1-phosphate uridylyltransferase, phosphoglucomutase, UDP-N-acetylglucosamine 4-epimerase, N-acetylgalactosamine kinase and UDP-N-acetylgalactosamine pyrophosphorylase.

15. Cell according to any one of preferred embodiments 1 to 14, wherein the cell is capable to synthesize at least two nucleotide-sugars, preferably at least three nucleotide-sugars, more preferably at least four nucleotide-sugars, even more preferably at least five nucleotide-sugars.

16. Cell according to any one of preferred embodiments 1 to 15, wherein the mixture comprises at least one neutral non-fucosylated oligosaccharide that is galactosylated, glucosylated, xylosylated, mannosylated, contains an N-acetylglucosamine, contains an N-acetylgalactosamine, contains a rhamnose, and/or contains an N-acetylmannosamine.

17. Cell according to any one of preferred embodiments 1 to 16, wherein the oligosaccharide mixture comprises at least one oligosaccharide that comprises an N-acetylglucosamine monosaccharide unit.

18. Cell according to any one of preferred embodiments 1 to 17, wherein the oligosaccharide mixture comprises at least one galactosylated oligosaccharide.

19. Cell according to any one of preferred embodiments 1 to 18, wherein the cell uses at least one precursor for the production of any one or more of the oligosaccharides, preferably the cell uses two or more precursors for the production of any one or more of the oligosaccharides, the precursor(s) being fed to the cell from the cultivation medium.

20. Cell according to any one of preferred embodiments 1 to 19, wherein the cell is producing at least one precursor for the production of any one of the oligosaccharides.

21. Cell according to any one of preferred embodiments 1 to 20, wherein the at least one precursor for the production of any one of the oligosaccharides is completely converted into any one of the oligosaccharides.

22. Cell according to any one of preferred embodiments 1 to 21, wherein the cell produces the oligosaccharides intracellularly and wherein a fraction or substantially all of the produced oligosaccharides remains intracellularly and/or is excreted outside the cell via passive or active transport.

23. Cell according to any one of preferred embodiments 1 to 22, wherein the cell is further genetically modified for
i) modified expression of an endogenous membrane protein, and/or
ii) modified activity of an endogenous membrane protein, and/or
iii) expression of a homologous membrane protein, and/or
iv) expression of a heterologous membrane protein,
wherein the membrane protein is involved in the secretion of any one of the neutral non-fucosylated oligosaccharides from the mixture outside the cell, preferably wherein the membrane protein is involved in the secretion of all of the oligosaccharides from the mixture from the cell.

24. Cell according to any one of preferred embodiments 1 to 23, wherein the cell is further genetically modified for
i) modified expression of an endogenous membrane protein, and/or
ii) modified activity of an endogenous membrane protein, and/or
iii) expression of a homologous membrane protein, and/or
iv) expression of a heterologous membrane protein,
wherein the membrane protein is involved in the uptake of a precursor and/or acceptor for the synthesis of any one of the neutral non-fucosylated oligosaccharides of the mixture, preferably wherein the membrane protein is involved in the uptake of all of the required precursors, more preferably wherein the membrane protein is involved in the uptake of all of the acceptors.

25. Cell according to any one of preferred embodiment 23 or 24, wherein the membrane protein is chosen from the list comprising porters, P-P-bond-hydrolysis-driven transporters, β-barrel porins, auxiliary transport proteins, putative transport proteins and phosphotransfer-driven group translocators,
preferably, the porters comprise MFS transporters, sugar efflux transporters and siderophore exporters,
preferably, the P-P-bond-hydrolysis-driven transporters comprise ABC transporters and siderophore exporters.

26. Cell according to any one of preferred embodiment 23 to 25, wherein the membrane protein provides improved production and/or enabled and/or enhanced efflux of any one of the oligosaccharides.

27. Cell according to any one of preferred embodiment 1 to 26, wherein the cell resists the phenomenon of lactose killing when grown in an environment in which lactose is combined with one or more other carbon source(s).

28. Cell according to any one of preferred embodiment 1 to 27, wherein the cell comprises a modification for reduced production of acetate compared to a non-modified progenitor.

29. Cell according to preferred embodiment 28, wherein the cell comprises a lower or reduced expression and/or abolished, impaired, reduced or delayed activity of any one or more of the proteins comprising beta-galactosidase, galactoside 0-acetyltransferase, N-acetylglucosamine-6-phosphate deacetylase, glucosamine-6-phosphate deaminase, N-acetylglucosamine repressor, ribonucleotide monophosphatase, EIICBA-Nag, UDP-glucose:undecaprenyl-phosphate glucose-1-phosphate transferase, L-fuculokinase, L-fucose isomerase, N-acetylneuraminate lyase, N-acetylmannosamine kinase, N-acetylmannosamine-6-phosphate 2-epimerase, EIIAB-Man, EIIC-Man, EIID-Man, ushA, galactose-1-phosphate uridylyltransferase, glucose-1-phosphate adenylyltransferase, glucose-1-phosphatase, ATP-dependent 6-phosphofructokinase isozyme 1, ATP-dependent 6-phosphofructokinase isozyme 2, glucose-6-phosphate isomerase, aerobic respiration control protein, transcriptional repressor IclR, lon protease, glucose-specific translocating phosphotransferase enzyme IIBC component ptsG, glucose-specific translocating phosphotransferase (PTS) enzyme IIBC component malX, enzyme IIA$^{Glc}$, beta-glucoside specific PTS enzyme II, fructose-specific PTS multiphosphoryl transfer protein FruA and FruB, ethanol dehydrogenase aldehyde dehydrogenase, pyruvate-formate lyase, acetate kinase, phosphoacyltransferase, phosphate acetyltransferase, pyruvate decarboxylase compared to a non-modified progenitor.

30. Cell according to any one of preferred embodiment 1 to 29, wherein the cell is capable to produce phosphoenolpyruvate (PEP).

31. Cell according to any one of preferred embodiment 1 to 30, wherein the cell is modified for enhanced production and/or supply of phosphoenolpyruvate (PEP) compared to a non-modified progenitor.

32. Cell according to any one of preferred embodiments 1 to 31, wherein any one of the neutral non-fucosylated oligosaccharide is a mammalian milk oligosaccharide.

33. Cell according to any one of preferred embodiments 1 to 32, wherein all the neutral non-fucosylated oligosaccharides are mammalian milk oligosaccharides.

34. A method to produce a mixture of at least four different neutral non-fucosylated oligosaccharides by a cell, preferably a single cell, the method comprising the steps of:
i) providing a cell that is capable of expressing, preferably expressing at least two glycosyltransferases and capable to synthesize one or more nucleotide-sugar(s), wherein the nucleotide-sugar(s) is/are donor(s) for the glycosyltransferases,
ii) cultivating the cell under conditions permissive to express the glycosyltransferases and to synthesize the nucleotide-sugars,
iii) preferably, separating at least one of the neutral non-fucosylated oligosaccharides from the cultivation, more preferably separating all of the neutral non-fucosylated oligosaccharides from the cultivation.

35. Method according to preferred embodiment 34, wherein the cell is a metabolically engineered cell according to any one of preferred embodiments 1 to 33.

36. Method according to preferred embodiment 35, wherein the cell is modified with gene expression modules, characterized in that the expression from any of the expression modules is either constitutive or is created by a natural inducer.

37. Method according to any one of preferred embodiment 35 or 36, wherein the cell comprises multiple copies of the same coding DNA sequence encoding for one protein.

38. Method according to any one of preferred embodiments 34 to 37, wherein the oligosaccharide mixture comprises at least three different neutral non-fucosylated oligosaccharides differing in degree of polymerization.

39. Method according to any one of preferred embodiments 34 to 38, wherein the cell produces five or more different neutral non-fucosylated oligosaccharides.

40. Method according to any one of preferred embodiments 34 to 39, wherein any one of the glycosyltransferases is chosen from the list comprising galactosyltransferases, glucosyltransferases, mannosyltransferases, N-acetylglucosaminyltransferases, N-acetylgalactosaminyltransferases, N-acetylmannosaminyltransferases, xylosyltransferases, glucosaminyltransferases, rhamnosyltransferases, N-acetylrhamnosyltransferases, UDP-4-amino-4,6-dideoxy-N-acetyl-beta-L-altrosamine transaminases, UDP-N-acetylglucosamine enolpyruvyl transferases and fucosaminyltransferases,
preferably, the galactosyltransferase is chosen from the list comprising beta-1,3-galactosyltransferase, N-acetylglucosamine beta-1,3-galactosyltransferase, beta-1,4-galactosyltransferase, N-acetylglucosamine beta-1,4-galactosyltransferase, alpha-1,3-galactosyltransferase and alpha-1,4-galactosyltransferase,
preferably, the glucosyltransferase is chosen from the list comprising alpha-glucosyltransferase, beta-1,2-glucosyltransferase, beta-1,3-glucosyltransferase and beta-1,4-glucosyltransferase,
preferably, the mannosyltransferase is chosen from the list comprising alpha-1,2-mannosyltransferase, alpha-1,3-mannosyltransferase and alpha-1,6-mannosyltransferase,
preferably, the N-acetylglucosaminyltransferase is chosen from the list comprising galactoside beta-1,3-N-acetylglucosaminyltransferase and beta-1,6-N-acetylglucosaminyltransferase,
preferably, the N-acetylgalactosaminyltransferase is chosen from the list comprising alpha-1,3-N-acetylgalactosaminyltransferase and beta-1,3-N-acetylgalactosaminyltransferase,
preferably, the cell is modified in the expression or activity of at least one of the glycosyltransferases.

41. Method according to any one of preferred embodiments 34 to 40, wherein the cell is capable to express, preferably expresses, at least three, more preferably at least four, even more preferably at least five, most preferably at least six glycosyltransferases.

42. Method according to any one of preferred embodiments 34 to 41, wherein any one of the glycosyltransferases is an N-acetylglucosaminyltransferase and any one of the donor nucleotide-sugars is UDP-N-acetylglucosamine (UDP-GlcNAc).

43. Method according to any one of preferred embodiments 34 to 42 wherein any one of the glycosyltransferases is a galactosyltransferase and any one of the donor nucleotide-sugar is UDP-galactose (UDP-Gal).

44. Method according to any one of preferred embodiment 34 to 43, wherein the glycosyltransferase is an N-acetylgalactosaminyltransferase and the donor nucleotide-sugar is UDP-N-acetylgalactosamine (UDP-GalNAc).

45. Method according to any one of preferred embodiment 34 to 44, wherein the glycosyltransferase is an N-acetylmannosaminyltransferase and the donor nucleotide-sugar is UDP-N-acetylmannosamine (UDP-ManNAc).

46. Method according to any one of preferred embodiments 34 to 45, wherein any one of the nucleotide-sugars is chosen from the list comprising UDP-N-acetylglucosamine (UDP-GlcNAc), UDP-galactose (UDP-Gal), UDP-N-acetylgalactosamine (UDP-GalNAc), UDP-N-acetylmannosamine (UDP-ManNAc), GDP-mannose (GDP-Man), UDP-glucose (UDP-Glc), GDP-rhamnose, UDP-xylose, UDP-2-acetamido-2,6-dideoxy-L-arabino-4-hexulose, UDP-2-acetamido-2,6-dideoxy-L-lyxo-4-hexulose, UDP-N-acetyl-L-rhamnosamine (UDP-L-RhaNAc or UDP-2-acetamido-2,6-dideoxy-L-mannose), dTDP-N-acetylfucosamine, UDP-N-acetylfucosamine (UDP-L-FucNAc or UDP-2-acetamido-2,6-dideoxy-L-galactose), UDP-N-acetyl-L-pneumosamine (UDP-L-PneNAC or UDP-2-acetamido-2,6-dideoxy-L-talose), UDP-N-acetylmuramic acid, UDP-N-acetyl-L-quinovosamine (UDP-L-QuiNAc or UDP-2-acetamido-2,6-dideoxy-L-glucose), GDP-L-quinovose.

47. Method according to any one of preferred embodiment 34 to 46, wherein the cell expresses one or more polypeptides chosen from the list comprising L-glutamine-D-fructose-6-phosphate aminotransferase, glucosamine-6-phosphate deaminase, phosphoglucosamine mutase, N-acetylglucosamine-6-phosphate deacetylase, N-acylglucosamine 2-epimerase, UDP-N-acetylglucosamine 2-epimerase, N-acetylmannosamine-6-phosphate 2-epimerase, glucosamine 6-phosphate N-acetyltransferase, N-acetylglucosamine-6-phosphate phosphatase, N-acetylmannosamine- 6-phosphate phosphatase, N-acetylmannosamine kinase, phosphoacetylglucosamine mutase, N-acetylglucosamine-1-phosphate uridylyltransferase, glucosamine-1-phosphate acetyltransferase, galactose-1-epimerase, galactokinase, glucokinase, galactose-1-phosphate uridylyltransferase, UDP-glucose 4-epimerase, glucose-1-phosphate uridylyltransferase, phosphoglucomutase, UDP-N-acetylglucosamine 4-epimerase, N-acetylgalactosamine kinase and UDP-N-acetylgalactosamine pyrophosphorylase.

48. Method according to any one of preferred embodiments 34 to 47, wherein the cell is capable to synthesize at least two nucleotide-sugars, preferably at least three nucleotide-sugars, more preferably at least four nucleotide-sugars, even more preferably at least five nucleotide-sugars.

49. Method according to any one of preferred embodiments 34 to 48, wherein the oligosaccharide mixture comprises at least one oligosaccharide that comprises an N-acetylglucosamine monosaccharide unit.

50. Method according to any one of preferred embodiments 34 to 49, wherein the oligosaccharide mixture comprises at least one galactosylated oligosaccharide.

51. Method according to any one of preferred embodiments 34 to 50, wherein any one of the neutral non-fucosylated oligosaccharides is galactosylated, glucosylated, xylosylated, mannosylated, contains an N-acetylglucosamine, contains an N-acetylgalactosamine, contains a rhamnose, and/or contains an N-acetylmannosamine.

52. Method according to any one of preferred embodiments 34 to 51, wherein the cell uses at least one precursor for the production of any one or more of the oligosaccharides, preferably the cell uses two or more precursors for the production of any one or more of the oligosaccharides, the precursor(s) being fed to the cell from the cultivation medium.

53. Method according to any one of preferred embodiments 34 to 52, wherein the cell is producing a precursor for the production of any one of the oligosaccharides.

54. Method according to any one of preferred embodiments 34 to 53, wherein the at least one precursor for the production of any one of the oligosaccharides is completely converted into any one of the oligosaccharides.

55. Method according to any one of preferred embodiments 34 to 54, wherein the cell produces the oligosaccharides intracellularly and wherein a fraction or substantially all of the produced oligosaccharides remains intracellularly and/or is excreted outside the cell via passive or active transport.

56. Method according to any one of preferred embodiments 34 to 55, wherein the cell is further genetically modified for
i) modified expression of an endogenous membrane protein, and/or
ii) modified activity of an endogenous membrane protein, and/or
iii) expression of a homologous membrane protein, and/or
iv) expression of a heterologous membrane protein,
wherein the membrane protein is involved in the secretion of any one of the neutral non-fucosylated oligosaccharides from the mixture outside the cell, preferably wherein the membrane protein is involved in the secretion of all of the oligosaccharides from the mixture from the cell.

57. Method according to any one of preferred embodiments 34 to 56, wherein the cell is further genetically modified for
i) modified expression of an endogenous membrane protein, and/or
ii) modified activity of an endogenous membrane protein, and/or
iii) expression of a homologous membrane protein, and/or
iv) expression of a heterologous membrane protein,
wherein the membrane protein is involved in the uptake of a precursor and/or acceptor for the synthesis of any one of the neutral non-fucosylated oligosaccharides of the mixture, preferably wherein the membrane protein is involved in the uptake of all of the required precursors, more preferably wherein the membrane protein is involved in the uptake of all of the acceptors.

58. Method according to any one of preferred embodiment 56 or 57, wherein the membrane protein is chosen from the list comprising porters, P-P-bond-hydrolysis-driven transporters, β-barrel porins, auxiliary transport proteins, putative transport proteins and phosphotransfer-driven group translocators,
preferably, the porters comprise MFS transporters, sugar efflux transporters and siderophore exporters,
preferably, the P-P-bond-hydrolysis-driven transporters comprise ABC transporters and siderophore exporters.

59. Method according to any one of preferred embodiment 56 to 58, wherein the membrane protein provides improved production and/or enabled and/or enhanced efflux of any one of the oligosaccharides.

60. Method according to any one of preferred embodiment 34 to 59, wherein the cell resists the phenomenon of lactose killing when grown in an environment in which lactose is combined with one or more other carbon source(s).

61. Method according to any one of preferred embodiment 34 to 60, wherein the cell comprises a modification for reduced production of acetate compared to a non-modified progenitor.

62. Method according to preferred embodiment 61, wherein the cell comprises a lower or reduced expression and/or abolished, impaired, reduced or delayed activity of any one or more of the proteins comprising beta-galactosidase, galactoside 0-acetyltransferase, N-acetylglucosamine-6-phosphate deacetylase, glucosamine-6-phosphate deaminase, N-acetylglucosamine repressor, ribonucleotide monophosphatase, EIICBA-Nag, UDP-glucose:undecaprenyl-phosphate glucose-1-phosphate transferase, L-fuculokinase, L-fucose isomerase, N-acetylneuraminate lyase, N-acetylmannosamine kinase, N-acetylmannosamine-6-phosphate 2-epimerase, EIIAB-Man, EIIC-Man, EIID-Man, ushA, galactose-1-phosphate uridylyltransferase, glucose-1-phosphate adenylyltransferase, glucose-1-phosphatase, ATP-dependent 6-phosphofructokinase isozyme 1, ATP-dependent 6-phosphofructokinase isozyme 2, glucose-6-phosphate isomerase, aerobic respiration control protein, transcriptional repressor IclR, lon protease, glucose-specific translocating phosphotransferase enzyme IIBC component ptsG, glucose-specific translocating phosphotransferase (PTS) enzyme IIBC component malX, enzyme IIA$^{Glc}$, beta-glucoside specific PTS enzyme II, fructose-specific PTS multiphosphoryl transfer protein FruA and FruB, ethanol dehydrogenase aldehyde dehydrogenase, pyruvate-formate lyase, acetate kinase, phosphoacyltransferase, phosphate acetyltransferase, pyruvate decarboxylase compared to a non-modified progenitor.

63. Method according to any one of preferred embodiment 34 to 62, wherein the cell is capable to produce phosphoenolpyruvate (PEP).

64. Method according to any one of preferred embodiment 34 to 63 wherein the cell is modified for enhanced production and/or supply of phosphoenolpyruvate (PEP) compared to a non-modified progenitor.

65. Method according to any one of preferred embodiments 34 to 64, wherein any one of the neutral non-fucosylated oligosaccharide is a mammalian milk oligosaccharide.

66. Method according to any one of preferred embodiments 34 to 65, wherein all the neutral non-fucosylated oligosaccharides are mammalian milk oligosaccharides.

67. Method according to any one of preferred embodiment 34 to 66, wherein the conditions comprise:
  use of a culture medium comprising at least one precursor and/or acceptor for the production of any one of the oligosaccharides, and/or
  adding to the culture medium at least one precursor and/or acceptor feed for the production of any one of the oligosaccharides.

68. Method according to any one of preferred embodiment 34 to 67, the method comprising at least one of the following steps:
  i) Use of a culture medium comprising at least one precursor and/or acceptor;
  ii) Adding to the culture medium in a reactor at least one precursor and/or acceptor feed wherein the total reactor volume ranges from 250 mL (milliliter) to 10,000 m$^3$ (cubic meter), preferably in a continuous manner, and preferably so that the final volume of the culture medium is not more than three-fold, preferably not more than two-fold, more preferably less than two-fold of the volume of the culture medium before the addition of the precursor and/or acceptor feed;
  iii) Adding to the culture medium in a reactor at least one precursor and/or acceptor feed wherein the total reactor volume ranges from 250 mL (milliliter) to 10,000 m$^3$ (cubic meter), preferably in a continuous manner, and preferably so that the final volume of the culture medium is not more than three-fold, preferably not more than two-fold, more preferably less than two-fold of the volume of the culture medium before the addition of the precursor and/or acceptor feed and wherein preferably, the pH of the precursor and/or acceptor feed is set between 3 and 7 and wherein preferably, the temperature of the precursor and/or acceptor feed is kept between 20° C. and 80° C.;
  iv) Adding at least one precursor and/or acceptor feed in a continuous manner to the culture medium over the course of 1 day, 2 days, 3 days, 4 days, 5 days by means of a feeding solution;
  v) Adding at least one precursor and/or acceptor feed in a continuous manner to the culture medium over the course of 1 day, 2 days, 3 days, 4 days, 5 days by means of a feeding solution and wherein preferably, the pH of the feeding solution is set between 3 and 7 and wherein preferably, the temperature of the feeding solution is kept between 20° C. and 80° C.;
  the method resulting in any one of the oligosaccharides with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final cultivation.

69. Method according to any one of preferred embodiment 34 to 67, the method comprising at least one of the following steps:
  i) Use of a culture medium comprising at least 50, more preferably at least 75, more preferably at least 100, more preferably at least 120, more preferably at least 150 gram of lactose per liter of initial reactor volume wherein the reactor volume ranges from 250 mL to 10,000 m$^3$ (cubic meter);
  ii) Adding to the culture medium a lactose feed comprising at least 50, more preferably at least 75, more preferably at least 100, more preferably at least 120, more preferably at least 150 gram of lactose per liter of initial reactor volume wherein the reactor volume ranges from 250 mL to 10,000 m$^3$ (cubic meter), preferably in a continuous manner, and preferably so that the final volume of the culture medium is not more than three-fold, preferably not more than two-fold, more preferably less than two-fold of the volume of the culture medium before the addition of the lactose feed;
  iii) Adding to the culture medium a lactose feed comprising at least 50, more preferably at least 75, more preferably at least 100, more preferably at least 120, more preferably at least 150 gram of lactose per liter of initial reactor volume wherein the reactor volume ranges from 250 mL to 10,000 m$^3$ (cubic meter), preferably in a continuous manner, and preferably so that the final volume of the culture medium is not more than three-fold, preferably not more than two-fold, more preferably less than two-fold of the volume of the culture medium before the addition of the lactose feed and wherein preferably the pH of the lactose feed is set between 3 and 7 and wherein preferably the temperature of the lactose feed is kept between 20° C. and 80° C.;
  iv) Adding a lactose feed in a continuous manner to the culture medium over the course of 1 day, 2 days, 3 days, 4 days, 5 days by means of a feeding solution;
  v) Adding a lactose feed in a continuous manner to the culture medium over the course of 1 day, 2 days, 3 days, 4 days, 5 days by means of a feeding solution and wherein the concentration of the lactose feeding solution is 50 g/L, preferably 75 g/L, more preferably 100 g/L, more preferably 125 g/L, more preferably 150 g/L, more preferably 175 g/L, more preferably 200 g/L, more preferably 225 g/L, more preferably 250 g/L, more preferably 275 g/L, more preferably 300 g/L, more preferably 325 g/L, more preferably 350 g/L, more preferably 375 g/L, more preferably, 400 g/L, more preferably 450 g/L, more preferably 500 g/L, even more preferably, 550 g/L, most preferably 600 g/L and wherein preferably the pH of the feeding solution is set between 3 and 7 and wherein preferably the temperature of the feeding solution is kept between 20° C. and 80° C.;
  the method resulting in any one of the oligosaccharides with a concentration of at least 50 g/L, preferably at least 75 g/L, more preferably at least 90 g/L, more preferably at least 100 g/L, more preferably at least 125 g/L, more preferably at least 150 g/L, more preferably at least 175 g/L, more preferably at least 200 g/L in the final cultivation.

70. Method according to preferred embodiment 69, wherein the lactose feed is accomplished by adding lactose from the beginning of the cultivation in a concentration of at least 5 mM, preferably in a concentration of 30, 40, 50, 60, 70, 80, 90, 100, 150 mM, more preferably in a concentration >300 mM.

71. Method according to any one of preferred embodiment 69 or 70, wherein the lactose feed is accomplished by adding lactose to the cultivation in a concentration, such, that throughout the production phase of the cultivation a lactose concentration of at least 5 mM, preferably 10 mM or 30 mM is obtained.

72. Method according to any one of preferred embodiment 34 to 71, wherein the host cells are cultivated for at least about 60, 80, 100, or about 120 hours or in a continuous manner.

73. Method according to any one of preferred embodiment 34 to 72, wherein the cell is cultivated in a culture medium comprising a carbon source comprising a monosaccharide, disaccharide, oligosaccharide, polysaccharide, polyol, glycerol, a complex medium including molasses, corn steep liquor, peptone, tryptone or yeast extract; preferably, wherein the carbon source is chosen from the list comprising glucose, glycerol, fructose, sucrose, maltose, lactose, arabinose, malto-oligosaccharides, maltotriose, sorbitol, xylose, rhamnose, galactose, mannose, methanol, ethanol, trehalose, starch, cellulose, hemi-cellulose, molasses, corn-steep liquor, high-fructose syrup, acetate, citrate, lactate and pyruvate.

74. Method according to any one of preferred embodiment 34 to 73, wherein the culture medium contains at least one precursor selected from the group comprising lactose, galactose, fucose, GlcNAc, GalNAc, lacto-N-biose (LNB), N-acetyllactosamine (LacNAc).

75. Method according to any one of preferred embodiment 34 to 74, wherein a first phase of exponential cell growth is provided by adding a carbon-based substrate, preferably glucose or sucrose, to the culture medium before the precursor, preferably lactose, is added to the culture medium in a second phase.

76. Method according to any one of preferred embodiment 34 to 75, wherein a first phase of exponential cell growth is provided by adding a carbon-based substrate, preferably glucose or sucrose, to the culture medium comprising a precursor, preferably lactose, followed by a second phase wherein only a carbon-based substrate, preferably glucose or sucrose, is added to the culture medium.

77. Method according to any one of preferred embodiment 34 to 76, wherein a first phase of exponential cell growth is provided by adding a carbon-based substrate, preferably glucose or sucrose, to the culture medium comprising a precursor, preferably lactose, followed by a second phase wherein a carbon-based substrate, preferably glucose or sucrose, and a precursor, preferably lactose, are added to the culture medium.

78. Method according to any one of preferred embodiments 34 to 77, wherein the separation comprises at least one of the following steps: clarification, ultrafiltration, nanofiltration, two-phase partitioning, reverse osmosis, microfiltration, activated charcoal or carbon treatment, treatment with non-ionic surfactants, enzymatic digestion, tangential flow high-performance filtration, tangential flow ultrafiltration, affinity chromatography, ion exchange chromatography, hydrophobic interaction chromatography and/or gel filtration, ligand exchange chromatography.

79. Method according to any one of preferred embodiments 34 to 78, further comprising purification of any one of the neutral non-fucosylated oligosaccharides from the cell.

80. Method according to any one of preferred embodiment 79, wherein the purification comprises at least one of the following steps: use of activated charcoal or carbon, use of charcoal, nanofiltration, ultrafiltration, electrophoresis, enzymatic treatment or ion exchange, use of alcohols, use of aqueous alcohol mixtures, crystallization, evaporation, precipitation, drying, drying, lyophilization, spray freeze drying, freeze spray drying, band drying, belt drying, vacuum band drying, vacuum belt drying, drum drying, roller drying, vacuum drum drying or vacuum roller drying.

81. Cell according to any one of preferred embodiments 1 to 33 or method according to any one of preferred embodiments 34 to 80, wherein the cell is a bacterium, fungus, yeast, a plant cell, an animal cell, or a protozoan cell,
preferably the bacterium is an *Escherichia coli* strain, more preferably an *Escherichia coli* strain which is a K-12 strain, even more preferably the *Escherichia coli* K-12 strain is *E. coli* MG1655,
preferably the fungus belongs to a genus chosen from the group comprising *Rhizopus, Dictyostelium, Penicillium, Mucor* or *Aspergillus,*
preferably the yeast belongs to a genus chosen from the group comprising *Saccharomyces, Zygosaccharomyces, Pichia, Komagataella, Hansenula, Yarrowia, Starmerella, Kluyveromyces* or Debaromyces,
preferably the plant cell is an algal cell or is derived from tobacco, alfalfa, rice, tomato, cotton, rapeseed, soy, maize, or corn plant,
preferably the animal cell is derived from non-human mammals, birds, fish, invertebrates, reptiles, amphibians or insects or is a genetically modified cell line derived from human cells excluding embryonic stem cells, more preferably the human and non-human mammalian cell is an epithelial cell, an embryonic kidney cell, a fibroblast cell, a COS cell, a Chinese hamster ovary (CHO) cell, a murine myeloma cell, an NIH-3T3 cell, a non-mammary adult stem cell or derivatives thereof, more preferably the insect cell is derived from *Spodoptera frugiperda, Bombyx mori, Mamestra brassicae, Trichoplusia ni* or *Drosophila melanogaster,*
preferably the protozoan cell is a *Leishmania tarentolae* cell.

82. Cell according to preferred embodiment 81, or method according to preferred embodiment 81, wherein the cell is a viable Gram-negative bacterium that comprises a reduced or abolished synthesis of poly-N-acetyl-glucosamine (PNAG), Enterobacterial Common Antigen (ECA), cellulose, colanic acid, core oligosaccharides, Osmoregulated Periplasmic Glucans (OPG), Glucosylglycerol, glycan, and/or trehalose compared to a non-modified progenitor.

83. Use of a cell according to any one of preferred embodiments 1 to 33, 81, 82, or method according to any one of preferred embodiments 34 to 82 for the production of a mixture of at least three different neutral non-fucosylated oligosaccharides.

DETAILED DESCRIPTION

The disclosure will be described in more detail in the examples.

The following examples will serve as further illustration and clarification of the disclosure and are not intended to be limiting.

EXAMPLES

Example 1. Materials and Methods *Escherichia coli*

Media

The Luria Broth (LB) medium consisted of 1% tryptone peptone (Difco, Erembodegem, Belgium), 0.5% yeast extract (Difco) and 0.5% sodium chloride (VWR. Leuven, Belgium). The minimal medium used in the cultivation experiments in 96-well plates or in shake flasks contained 2.00 g/L NH4Cl, 5.00 g/L (NH4)2SO4, 2.993 g/L KH2PO4, 7.315 g/L K2HPO4, 8.372 g/L MOPS, 0.5 g/L NaCl, 0.5 g/L MgSO4·7H2O, 30 g/L sucrose or 30 g/L glycerol, 1 ml/L vitamin solution, 100 µl/L molybdate solution, and 1 mL/L selenium solution. As specified in the respective examples, 20 g/L lactose, 20 g/L LacNAc and/or 20 g/L LNB were additionally added to the medium as precursor(s). The minimal medium was set to a pH of 7 with 1 M KOH. Vitamin solution consisted of 3.6 g/L FeCl2·4H2O, 5 g/L CaCl2·2H2O, 1.3 g/L MnCl2·2H2O, 0.38 g/L CuCl2·2H2O, 0.5 g/L CoCl2·6H2O, 0.94 g/L ZnCl2, 0.0311 g/L H3B04, 0.4 g/L Na2EDTA·2H2O and 1.01 g/L thiamine·HCl. The molybdate solution contained 0.967 g/L NaMoO4·2H2O. The selenium solution contained 42 g/L Seo2.

The minimal medium for fermentations contained 6.75 g/L NH4Cl, 1.25 g/L (NH4)2SO4, 2.93 g/L KH2PO4 and 7.31 g/L KH2PO4, 0.5 g/L NaCl, 0.5 g/L MgSO4·7H2O, 30 g/L sucrose or 30 g/L glycerol, 1 mL/L vitamin solution, 100 µL/L molybdate solution, and 1 mL/L selenium solution with the same composition as described above. As specified in the respective examples, 20 g/L lactose, 20 g/L LacNAc and/or 20 g/L LNB were additionally added to the medium as precursor(s).

Complex medium was sterilized by autoclaving (121° C., 21 min) and minimal medium by filtration (0.22 µm Sartorius). When necessary, the medium was made selective by adding an antibiotic: e.g., chloramphenicol (20 mg/L), carbenicillin (100 mg/L), spectinomycin (40 mg/L) and/or kanamycin (50 mg/L).

Plasmids pKD46 (Red helper plasmid, Ampicillin resistance), pKD3 (contains an FRT-flanked chloramphenicol resistance (cat) gene), pKD4 (contains an FRT-flanked kanamycin resistance (kan) gene), and pCP20 (expresses FLP recombinase activity) plasmids were obtained from Prof. R. Cunin (Vrije Universiteit Brussel, Belgium in 2007). Plasmids were maintained in the host *E. coli* DH5alpha (F−, phi80dlacZΔM15, Δ(lacZYA-argF) U169, deoR, recA1, endA1, hsdR17(rk−, mk+), phoA, supE44, lambda−, thi-1, gyrA96, relA1) bought from Invitrogen.

Strains and Mutations

*Escherichia coli* K12 MG1655 [λ−, F−, rph-1] was obtained from the *Coli* Genetic Stock Center (US), CGSC Strain #: 7740, in March 2007. Gene disruptions, gene introductions and gene replacements were performed using the technique published by Datsenko and Wanner (PNAS 97 (2000), 6640-6645). This technique is based on antibiotic selection after homologous recombination performed by lambda Red recombinase. Subsequent catalysis of a flippase recombinase ensures removal of the antibiotic selection cassette in the final production strain. Transformants carrying a Red helper plasmid pKD46 were grown in 10 mL LB media with ampicillin, (100 mg/L) and L-arabinose (10 mM) at 30° C. to an $OD_{600}$ nm of 0.6. The cells were made electrocompetent by washing them with 50 mL of ice-cold water, a first time, and with 1 mL ice cold water, a second time. Then, the cells were resuspended in 50 µL of ice-cold water. Electroporation was done with 50 µL of cells and 10-100 ng of linear double-stranded-DNA product by using a Gene Pulser™ (BioRad) (600Ω, 25 µFD, and 250 volts). After electroporation, cells were added to 1 mL LB media incubated 1 h at 37° C., and finally spread onto LB-agar containing 25 mg/L of chloramphenicol or 50 mg/L of kanamycin to select antibiotic resistant transformants. The selected mutants were verified by PCR with primers upstream and downstream of the modified region and were grown in LB-agar at 42° C. for the loss of the helper plasmid. The mutants were tested for ampicillin sensitivity.

The linear ds-DNA amplicons were obtained by PCR using pKD3, pKD4 and their derivates as template. The primers used had a part of the sequence complementary to the template and another part complementary to the side on the chromosomal DNA where the recombination must take place. For the genomic knock-out, the region of homology was designed 50-nt upstream and 50-nt downstream of the start and stop codon of the gene of interest. For the genomic knock-in, the transcriptional starting point (+1) had to be respected. PCR products were PCR-purified, digested with Dpnl, re-purified from an agarose gel, and suspended in elution buffer (5 mM Tris, pH 8.0). Selected mutants were transformed with pCP20 plasmid, which is an ampicillin and chloramphenicol resistant plasmid that shows temperature-sensitive replication and thermal induction of FLP synthesis. The ampicillin-resistant transformants were selected at 30° C., after which a few were colony purified in LB at 42° C. and then tested for loss of all antibiotic resistance and of the FLP helper plasmid. The gene knock outs and knock ins are checked with control primers.

In an example to produce lactose (Gal-b1,4-Glc), the mutant strain was derived from *E. coli* K12 MG1655 and modified with genomic knock-outs of the *E. coli* lacZ, glk genes and the *E. coli* galETKM operon, together with genomic knock-ins of constitutive transcriptional units for an N-acetylglucosamine beta-1,4-galactosyltransferase like, e.g., lgtB from *N. meningitidis* (UniProt ID Q51116) and a UDP-glucose 4-epimerase like, e.g., galE from *E. coli* (UniProt ID P09147).

In an example to produce lacto-N-triose (LN3, LNT-II, GlcNAc-b1,3-Gal-b1,4-Glc) and neutral non-fucosylated oligosaccharides originating thereof comprising lacto-N-tetraose (LNT) and lacto-N-neotetraose (LNnT), the mutant strain was derived from *E. coli* K12 MG1655 and modified with a knock-out of the *E. coli* LacZ and nagB genes and with a genomic knock-in of a constitutive transcriptional unit for a galactoside beta-1,3-N-acetylglucosaminyltransferase like, e.g., LgtA from *N. meningitidis* (UniProt ID Q9JXQ6). For LNT or LNnT production, the mutant strain is further modified with constitutive transcriptional units for an N-acetylglucosamine beta-1,3-galactosyltransferase like, e.g., WbgO from *E. coli* O55:H7 (UniProt ID D3QY14) or an N-acetylglucosamine beta-1,4-galactosyltransferase like, e.g., LgtB from *N. meningitidis* (UniProt ID Q51116), respectively, that can be delivered to the strain either via genomic knock-in or from an expression plasmid. Optionally, multiple copies of the galactoside beta-1,3-N-acetylglucosaminyltransferase, the N-acetylglucosamine beta-1,3-galactosyltransferase and/or the N-acetylglucosamine beta-1,4-galactosyltransferase genes could be added to the mutant *E. coli* strains. Also, LNT and/or LNnT production can be enhanced by improved UDP-GlcNAc production by modification of the strains with one or more genomic knock-ins of a constitutive transcriptional unit for an L-glutamine-D-fructose-6-phosphate aminotransferase like, e.g., the mutant glmS*54 from *E. coli* which differs from the wild-type glmS (UniProt ID P17169) by an A39T, an R250C and an G472S mutation. In addition, the strains can optionally be modified for enhanced UDP-galactose production with genomic knock-outs of the *E. coli* ushA, galT, ldhA and agp genes. The mutant *E. coli* strains can also optionally be adapted with a genomic knock-in of a constitutive transcriptional unit for a UDP-glucose-4-epimerase like, e.g., galE from *E. coli* (UniProt ID P09147), a phosphoglucosamine mutase like, e.g., glmM from *E. coli* (UniProt ID P31120) and an N-acetylglucosamine-1-phosphate uridyltransferase/glucosamine-1-phosphate acetyltransferase like, e.g., glmU from *E. coli* (UniProt ID P0ACC7). The mutant strains could also optionally be adapted for growth on sucrose via genomic knock-ins of constitutive transcriptional units containing a sucrose transporter like, e.g., CscB from *E. coli* W (UniProt ID E0IXR1), a fructose kinase like, e.g., Frk originating from *Z. mobilis* (UniProt ID Q03417) and a sucrose phosphorylase like, e.g., BaSP originating from *B. adolescentis* (UniProt ID A0ZZH6).

In an example to produce N-acetyllactosamine (LacNAc, Gal-b-1,4-GlcNAc) or lacto-N-biose (LNB, Gal-b1,3-GlcNAc), the mutant strains were derived from *E. coli* K12 MG1655 comprising knock-outs of the *E. coli* nagA and nagB genes and a genomic knock-in of a constitutive transcriptional unit containing a glucosamine 6-phosphate N-acetyltransferase like, e.g., GNA1 from *Saccharomyces cerevisiae* (UniProt ID P43577). The mutant strains were further modified with constitutive transcriptional units for an N-acetylglucosamine beta-1,3-galactosyltransferase like, e.g., WbgO from *E. coli* O55:H7 (UniProt ID D3QY14) to produce LNB or an N-acetylglucosamine beta-1,4-galactosyltransferase like, e.g., LgtB from *N. meningitidis* (UniProt ID Q51116) to produce LacNAc. Those transcriptional units for the N-acetylglucosamine beta-1,3-galactosyltransferase and the N-acetylglucosamine beta-1,4-galactosyltransferase can be delivered to the strains either via genomic knock-in or from an expression plasmid. Optionally, multiple copies of the N-acetylglucosamine beta-1,3-galactosyltransferase and/or N-acetylglucosamine beta-1,4-galactosyltransferase genes could be added to the mutant *E. coli* strains. Optionally, the mutant strains can be modified with a constitutive transcriptional unit for an L-glutamine-D-fructose-6-phosphate aminotransferase like, e.g., the mutant glmS*54 from *E. coli* (which differs from the wild-type glmS (UniProt ID P17169) by an A39T, an R250C and a G472S mutation) for enhanced UDP-GlcNAc synthesis. Optionally, the mutant strains can be further modified with a constitutive transcriptional unit for a phosphatase like any one of, e.g., the *E. coli* genes comprising aphA, Cof, HisB, OtsB, SurE, Yaed, YcjU, YedP, YfbT, YidA, YigB, YihX, YniC, YqaB, YrbL, AppA, Gph, SerB, YbhA, YbiV, YbjL, Yfb, YieH, YjgL, YjjG, YrfG and YbiU or PsMupP from *Pseudomonas putida*, ScDOG1 from *S. cerevisiae* and BsAraL from *Bacillus subtilis* as described in WO18122225 for enhanced GlcNAc production. In addition, the strains can optionally be modified for enhanced UDP-galactose production with genomic knock-outs of the *E. coli* ushA, galT, ldhA and agp genes. The mutant *E. coli* strains can also optionally be adapted with a genomic knock-in of a constitutive transcriptional unit for a UDP-glucose-4-epimerase like, e.g., galE from *E. coli* (UniProt ID P09147). The mutant strains can also optionally be adapted for growth on sucrose via genomic knock-ins of constitutive transcriptional units containing a sucrose transporter like, e.g., CscB from *E. coli* W (UniProt ID E0IXR1), a fructose kinase like, e.g., Frk originating from *Z. mobilis* (UniProt ID Q03417) and a sucrose phosphorylase like, e.g., BaSP originating from *B. adolescentis* (UniProt ID A0ZZH6).

Alternatively, and/or additionally, production of LNB, LacNAc, LN3, LNT, LNnT and oligosaccharides derived thereof can further be optimized in the mutant *E. coli* strains with a genomic knock-in of a constitutive transcriptional unit comprising a membrane transporter protein like, e.g., MdfA from *Cronobacter muytjensii* (UniProt ID A0A2T7ANQ9), MdfA from *Citrobacter youngae* (UniProt ID D4BC23), MdfA from *E. coli* (UniProt ID P0AEY8), MdfA from *Yokenella regensburgei* (UniProt ID G9Z5F4), iceT from *E. coli* (UniProt ID A0A024L207) or iceT from *Citrobacter youngae* (UniProt ID D4B8A6).

Preferably, but not necessarily, the glycosyltransferases, the proteins involved in nucleotide-activated sugar synthesis and/or membrane transporter proteins were N- and/or C-terminally fused to a solubility enhancer tag like, e.g., a SUMO-tag, an MBP-tag, His, FLAG, Strep-II, Halo-tag, NusA, thioredoxin, GST and/or the Fh8-tag to enhance their solubility (Costa et al., Front. Microbiol. 2014; Fox et al., Protein Sci. 2001, 10(3), 622-630; Jia and Jeaon, Open Biol. 2016, 6: 160196).

Optionally, the mutant *E. coli* strains were modified with a genomic knock-in of a constitutive transcriptional unit encoding a chaperone protein like, e.g., DnaK, DnaJ, GrpE, or the GroEL/ES chaperonin system (Baneyx F., Palumbo J. L. (2003) Improving Heterologous Protein Folding via Molecular Chaperone and Foldase Co-Expression. In: Vaillancourt P. E. (eds) *E. coli* Gene Expression Protocols. Methods in Molecular Biology™, vol. 205. Humana Press).

Optionally, the mutant *E. coli* strains are modified to create a glycominimized *E. coli* strain comprising genomic knock-out of any one or more of non-essential glycosyltransferase genes comprising pgaC, pgaD, rfe, rffT, rffM, bcsA, bcsB, bcsC, wcaA, wcaC, wcaE, wcaI, wcaJ, wcaL, waaH, waaF, waaC, waaU, waaZ, waaJ, waaO, waaB, waaS, waaG, waaQ, wbbI, arnC, arnT, yfdH, wbbK, opgG, opgH, ycjM, glgA, glgB, malQ, otsA and yaiP.

All constitutive promoters, UTRs and terminator sequences originated from the libraries described by Mutalik et al. (Nat. Methods 2013, No. 10, 354-360) and Cambray et al. (Nucleic Acids Res. 2013, 41(9), 5139-5148). All genes were ordered synthetically at Twist Bioscience or IDT and the codon usage was adapted using the tools of the supplier.

All strains were stored in cryovials at −80° C. (overnight LB culture mixed in a 1:1 ratio with 70% glycerol).

Cultivation Conditions

A preculture of 96-well microtiter plate experiments was started from a cryovial, in 150 μL LB and was incubated overnight at 37° C. on an orbital shaker at 800 rpm. This culture was used as inoculum for a 96-well square microtiter plate, with 400 μL minimal medium by diluting 400×. These final 96-well culture plates were then incubated at 37° C. on an orbital shaker at 800 rpm for 72 h, or shorter, or longer. To measure sugar concentrations at the end of the cultivation experiment whole broth samples were taken from each well by boiling the culture broth for 15 min at 60° C. before spinning down the cells (=average of intra- and extracellular sugar concentrations).

A preculture for the bioreactor was started from an entire 1 mL cryovial of a certain strain, inoculated in 250 mL or 500 mL minimal medium in a 1 L or 2.5 L shake flask and incubated for 24 h at 37° C. on an orbital shaker at 200 rpm. A 5 L bioreactor was then inoculated (250 mL inoculum in 2 L batch medium); the process was controlled by MFCS control software (Sartorius Stedim Biotech, Melsungen, Germany). Culturing condition were set to 37° C., and maximal stirring; pressure gas flow rates were dependent on the strain and bioreactor. The pH was controlled at 6.8 using 0.5 M H2SO4 and 20% NH4OH. The exhaust gas was cooled. 10% solution of silicone antifoaming agent was added when foaming raised during the fermentation.

Optical Density

Cell density of the cultures was frequently monitored by measuring optical density at 600 nm (Implen Nanophotometer NP80, Westburg, Belgium or with a Spark 10M microplate reader, Tecan, Switzerland).

Analytical Analysis

Standards such as but not limited to sucrose, lactose, N-acetyllactosamine (LacNAc), lacto-N-biose (LNB), lacto-N-triose II (LN3), lacto-N-tetraose (LNT) and lacto-N-neotetraose (LNnT) were purchased from Carbosynth (UK), Elicityl (France) and IsoSep (Sweden). Other compounds were analyzed with in-house made standards.

Oligosaccharides were analyzed on a Waters Acquity H-class UPLC with Evaporative Light Scattering Detector (ELSD) or a Refractive Index (RI) detection. A volume of 0.7 µL sample was injected on a Waters Acquity UPLC BEH Amide column (2.1×100 mm; 130 Å; 1.7 µm) column with an Acquity UPLC BEH Amide VanGuard column, 130 Å, 2.1×5 mm. The column temperature was 50° C. The mobile phase consisted of a ¼ water and ¾ acetonitrile solution to which 0.2% triethylamine was added. The method was isocratic with a flow of 0.130 mL/min. The ELS detector had a drift tube temperature of 50° C. and the N2 gas pressure was 50 psi, the gain 200 and the data rate 10 pps. The temperature of the RI detector was set at 35° C.

Oligosaccharides were also analyzed on a Waters Acquity H-class UPLC with Refractive Index (RI) detection. A volume of 0.5 µL sample was injected on a Waters Acquity UPLC BEH Amide column (2.1×100 mm; 130 Å; 1.7 µm). The column temperature was 50° C. The mobile phase consisted of a mixture of 72% acetonitrile and 28% ammonium acetate buffer (100 mM) to which 0.1% triethylamine was added. The method was isocratic with a flow of 0.260 mL/min. The temperature of the RI detector was set at 35° C.

For analysis on a mass spectrometer, a Waters Xevo TQ-MS with Electron Spray Ionization (ESI) was used with a desolvation temperature of 450° C., a nitrogen desolvation gas flow of 650 L/h and a cone voltage of 20 V. The MS was operated in selected ion monitoring (SIM) in negative mode for all oligosaccharides. Separation was performed on a Waters Acquity UPLC with a Thermo Hypercarb column (2.1×100 mm; 3 µm) on 35° C. A gradient was used wherein eluent A was ultrapure water with 0.1% formic acid and wherein eluent B was acetonitrile with 0.1% formic acid. The oligosaccharides were separated in 55 min using the following gradient: an initial increase from 2 to 12% of eluent B over 21 min, a second increase from 12 to 40% of eluent B over 11 min and a third increase from 40 to 100% of eluent B over 5 min. As a washing step 100% of eluent B was used for 5 min. For column equilibration, the initial condition of 2% of eluent B was restored in 1 min and maintained for 12 min.

Sugars at low concentrations (below 50 mg/L) were analyzed on a Dionex HPAEC system with pulsed amperometric detection (PAD). A volume of 5 µL of sample was injected on a Dionex CarboPac PA200 column 4×250 mm with a Dionex CarboPac PA200 guard column 4×50 mm. The column temperature was set to 30° C. A gradient was used wherein eluent A was deionized water, wherein eluent B was 200 mM Sodium hydroxide and wherein eluent C was 500 mM Sodium acetate. The oligosaccharides were separated in 60 min while maintaining a constant ratio of 25% of eluent B using the following gradient: an initial isocratic step maintained for 10 min of 75% of eluent A, an initial increase from 0 to 4% of eluent C over 8 min, a second isocratic step maintained for 6 min of 71% of eluent A and 4% of eluent C, a second increase from 4 to 12% of eluent C over 2.6 min, a third isocratic step maintained for 3.4 min of 63% of eluent A and 12% of eluent C and a third increase from 12 to 48% of eluent C over 5 min. As a washing step 48% of eluent C was used for 3 min. For column equilibration, the initial condition of 75% of eluent A and 0% of eluent C was restored in 1 min and maintained for 11 min. The applied flow was 0.5 mL/min.

Example 2. Materials and Methods *Saccharomyces cerevisiae*

Media

Strains were grown on Synthetic Defined yeast medium with Complete Supplement Mixture (SD CSM) or CSM drop-out (SD CSM-His) containing 6.7 g/L Yeast Nitrogen Base without amino acids (YNB w/o AA, Difco), 20 g/L agar (Difco) (solid cultures), 22 g/L glucose monohydrate or 20 g/L lactose and 0.79 g/L CSM or 0.77 g/L CSM-His (MP Biomedicals).

Strains

*S. cerevisiae* BY4742 created by Brachmann et al. (Yeast (1998) 14:115-32) was used, available in the Euroscarf culture collection. All mutant strains were created by homologous recombination or plasmid transformation using the method of Gietz (Yeast 11:355-360, 1995).

Plasmids

In an example to produce UDP-galactose, a yeast expression plasmid was derived from the pRS420-plasmid series (Christianson et al., 1992, Gene 110: 119-122) containing the HIS3 selection marker and a constitutive transcriptional unit for a UDP-glucose-4-epimerase like, e.g., galE from *E. coli* (UniProt ID P09147). In an example to produce LN3 and LN3-derived oligosaccharides like LNT or LNnT, this plasmid was further modified with constitutive transcriptional units for a lactose permease like, e.g., LAC12 from *K lactis* (UniProt ID P07921), a galactoside beta-1,3-N-acetylglucosaminyltransferase like, e.g., lgtA from *N. meningitidis* (UniProt ID Q9JXQ6) and, an N-acetylglucosamine beta-1, 3-galactosyltransferase like, e.g., WbgO from *E. coli* 055:H7 (UniProt ID D3QY14) or an N-acetylglucosamine beta-1,4-galactosyltransferase like, e.g., lgtB from *N. meningitidis* (UniProt ID Q51116), respectively.

Preferably, but not necessarily, any one or more of the glycosyltransferases, the proteins involved in nucleotide-activated sugar synthesis and/or membrane transporter proteins were N- and/or C-terminally fused to a SUMOstar tag (e.g., obtained from pYSUMOstar, Life Sensors, Malvern, PA) to enhance their solubility.

Optionally, the mutant yeast strains were modified with a genomic knock-in of a constitutive transcriptional unit encoding a chaperone protein like, e.g., Hsp31, Hsp32, Hsp33, Sno4, Kar2, Ssb1, Sse1, Sse2, Ssa1, Ssa2, Ssa3, Ssa4, Ssb2, Ecm10, Ssc1, Ssq1, Ssz1, Lhs1, Hsp82, Hsc82, Hsp78, Hsp104, Tcp1, Cct4, Cct8, Cct2, Cct3, Cct5, Cct6, or Cct7 (Gong et al., 2009, Mol. Syst. Biol. 5: 275).

Plasmids were maintained in the host *E. coli* DH5alpha (F⁻, phi80d/acZdeltaM15, delta(lacZYA-argF)U169, deoR, recA1, endA1, hsdR17(rk⁻, mk⁺), phoA, supE44, lambda⁻, thi-1, gyrA96, relA1) bought from Invitrogen.

Heterologous and Homologous Expression

Genes that needed to be expressed, be it from a plasmid or from the genome were synthetically synthetized with one of the following companies: DNA2.0, Gen9, IDT or Twist Bioscience. Expression could be further facilitated by optimizing the codon usage to the codon usage of the expression host. Genes were optimized using the tools of the supplier.

Cultivations Conditions

In general, yeast strains were initially grown on SD CSM plates to obtain single colonies. These plates were grown for 2-3 days at 30° C. Starting from a single colony, a preculture was grown over night in 5 mL at 30° C., shaking at 200 rpm.

Subsequent 125 mL shake flask experiments were inoculated with 2% of this preculture, in 25 mL media. These shake flasks were incubated at 30° C. with an orbital shaking of 200 rpm.

Gene Expression Promoters

Genes were expressed using synthetic constitutive promoters, as described by Blazeck (Biotechnology and Bioengineering, Vol. 109, No. 11, 2012).

Example 3. Production of an Oligosaccharide Mixture Comprising GlcNAc-b1,3-Gal-b1,4-GlcNAc and poly-LacNAc (Gal-b1,4-GlcNAc)n Structures with a Modified *E. coli* Host An *E. coli* K-12 MG1655 strain is modified with a knock-out of the *E. coli* nagB gene together with genomic knock-ins of constitutive transcriptional units for the phosphatase yqaB from *E. coli* (UniProt ID NP_417175.1), GNA1 from *S. cerevisiae* (UniProt ID P43577) and LgtB from *N. meningitidis* (UniProt ID Q51116) to produce LacNAc. In a next step, the novel strain is additionally transformed with an expression plasmid containing a constitutive transcriptional unit for the galactoside beta-1,3-N-acetylglucosaminyltransferase (LgtA) from *N. meningitidis* (UniProt ID Q9JXQ6). By subsequent action of the homologous EcGlmS, EcGlmM and EcGlmU enzymes, the mutant strain is capable of producing UDP-GlcNAc, which is used by the heterologous LgtA protein to modify LacNAc. The novel strain is evaluated for production of LacNAc, GlcNAc-b1,3-Gal-b1,4-GlcNAc and poly-LacNAc structures (Gal-b1,4-GlcNAc)n which are built of repeated N-acetyllactosamine units that are beta1,3-linked to each other, in whole broth samples in a growth experiment according to the culture conditions provided in Example 1, in which the culture medium contains glycerol as carbon source.

Example 4. Production of an Oligosaccharide Mixture Comprising GlcNAc-b1,3-Gal-b1,4-GlcNAc, beta-Gal-(1,4)-beta-GlcNAc-(1,3)-[beta-GlcNAc-(1,6)]-beta-Gal-(1,4)-GlcNAc and poly-LacNAc Structures with a Modified *E. coli* Host The mutant *E. coli* strain as described in Example 3 is further modified with a second expression plasmid containing a constitutive transcriptional unit for the human N-acetyllactosaminide beta-1,6-N-acetylglucosaminyltransferase GCNT2 (UniProt ID Q8NOV5). The novel strain is evaluated for production of an oligosaccharide mixture comprising LacNAc, GlcNAc-b1,3-Gal-b1,4-GlcNAc, GlcNAc-b1,6-Gal-b1,4-GlcNAc, (Gal-b1,4-GlcNAc)n structures and beta-Gal-(1,4)-beta-GlcNAc-(1,3)-[beta-GlcNAc-(1,6)]-beta-Gal-(1,4)-GlcNAc in whole broth samples in a growth experiment according to the culture conditions provided in Example 1, in which the culture medium contains glycerol as carbon source.

Example 5. Production of an Oligosaccharide Mixture Comprising Gal-a1,3-LacNAc, LN3, LNnT and Gal-a1,3-LNnT with a Modified *E. coli* Host An *E. coli* strain modified to produce LacNAc as described in Example 3 is further modified with a genomic knock-out of the *E. coli* lacZ gene and transformed with a compatible expression plasmid containing a constitutive transcriptional unit for the C-terminal catalytic domain comprising amino acid residues 80 to 367 of the alpha-1,3-galactosyltransferase (a3FTcd) from *Bos taurus* (UniProt ID P14769). The novel strain is evaluated for production of an oligosaccharide mixture comprising Gal-a1,3-LacNAc (Gal-a1,3-Gal-b1,4-GlcNAc), LN3, LNnT and Gal-a1,3-LNnT (Gal-a1,3-Gal-b1,4-GlcNAc-b1,3-Gal-b1,4-Glc) in whole broth samples in a growth experiment according to the culture conditions provided in Example 1, in which the culture medium contains glycerol as carbon source and lactose as precursor.

Example 6. Production of an Oligosaccharide Mixture Comprising LacNAc, GalNAc-b1,3-lactose, Gal-b1,3-GalNAc-b1,3-lactose, LN3, LNnT, GalNAc-b1,3-LacNAc, Gal-b1,3-GalNAc-b1,3-LacNAc, poly-LacNAc (Gal-b1,4-GlcNAc)n and GalNAc-ylated poly-LacNAc Structures with a Modified *E. coli* Host An *E. coli* K-12 MG1655 strain is modified with a knock-out of the *E. coli* nagB and lacZ genes together with genomic knock-ins of constitutive transcriptional units for the mutant L-glutamine-D-fructose-6-phosphate aminotransferase glmS*54 from *E. coli* (differing from the wild-type glmS (UniProt ID P17169) by an A39T, an R250C and an G472S mutation), GNA1 from *S. cerevisiae* (UniProt ID P43577), the phosphatase yqaB from *E. coli* (UniProt ID NP_417175.1), the galactoside beta-1,3-N-acetylglucosaminyltransferase (LgtA) from *N. meningitidis* (UniProt ID Q9JXQ6), LgtB from *N. meningitidis* (UniProt ID Q51116), the 4-epimerase (WbpP) of *Pseudomonas aeruginosa* (UniProt ID Q8KN66) and the β1,3-N-acetylgalactosaminyltransferase (LgtD) from *Haemophilus influenzae* (UniProt ID A0A2X4DBP3). The novel strain is evaluated for production of an oligosaccharide mixture comprising LacNAc, LN3, LNnT, GalNAc-b1,3-lactose, Gal-b1,3-GalNAc-b1,3-lactose, GalNAc-b1,3-Gal-b1,4-GlcNAc-b1,3-Gal-b1,4-Glc, GalNAc-b1,3-LacNAc, Gal-b1,3-GalNAc-b1,3-LacNAc, poly-LacNAc structures, i.e., (Gal-b1,4-GlcNAc)n and GalNAc-ylated poly-LacNAc structures, in a growth experiment according to the culture conditions provided in Example 1, in which the culture medium comprises glycerol as carbon source and lactose as precursor.

Example 7. Production of an Oligosaccharide Mixture Comprising LNB, LN3, LNT, GalNAc-b1,3-lactose, Gal-b1,3-GalNAc-b1,3-lactose, GalNAc-b1,3-LNB and Gal-b1,3-GalNAc-b1,3-LNB with a Modified *E. coli* Host An *E. coli* strain is modified with genomic knock-out of the *E. coli* nagB gene and genomic knock-ins of constitutive expression cassettes for the phosphatase yqaB from *E. coli* (UniProt ID NP_417175.1), GNA1 from *S. cerevisiae* (UniProt ID P43577) and WbgO from *E. coli* O55:H7 (UniProt ID D3QY14) to produce LNB. In a next step, the LNB producing *E. coli* strain is further modified with a knock-out of the *E. coli* lacZ gene and with knock-ins of constitutive expression units for the 4-epimerase (WbpP) of *P. aeruginosa* (UniProt ID Q8KN66), the galactoside beta-1,3-N-acetylglucosaminyltransferase (LgtA) from *N. meningitidis* (UniProt ID Q9JXQ6) and the β1,3-N-acetylgalactosaminyltransferase (LgtD) from *H. influenzae* (UniProt ID A0A2X4DBP3). The novel strain is evaluated for production of an oligosaccharide mixture comprising LNB, LN3, LNT, GalNAc-b1,3-lactose, Gal-b1,3-GalNAc-b1,3-lactose, GalNAc-b1,3-Gal-b1,3-GlcNAc-b1,3-Gal-b1,4-Glc, GalNAc-b1,3-LNB and Gal-b1,3-GalNAc-b1,3-LNB in a growth experiment according to the culture conditions provided in Example 1, in which the culture medium comprises glycerol as carbon source and lactose as precursor.

Example 8. Production of an Oligosaccharide Mixture Comprising LNT, LNnT and poly-galactosylated Structures in a Modified *E. coli* Host when Evaluated in Fed-Batch Fermentations An *E. coli* strain modified to produce LNnT as described in Example 1, is further modified with genomic knock-ins of constitutive transcriptional units for WbgO from *E. coli* O55:H7 (UniProt ID D3QY14). In a next step, the novel strain is evaluated in a fed-batch fermentation process in a 5 L bioreactor as described in Example 1. In this example sucrose is used as a carbon source and lactose is added in the batch medium as precursor. Regular broth samples are taken, and sugars produced are measured as described in Example 1. Fermentation broth of the selected strain taken at regular time points in fed-batch phase is evaluated for production of an oligosaccharide mixture comprising Lacto-N-triose II (LN3), Lacto-N-neotetraose (LNnT), Lacto-N-tetraose (LNT), para-Lacto-N-neopentaose, para-Lacto-N-pentaose, para-Lacto-N-neohexaose, para-Lacto-N-hexaose, beta-(1,3)Galactosyl-para-Lacto-N-neopentaose and beta-(1,4)Galactosyl-para-Lacto-N-pentaose.

Example 9. Production of an Oligosaccharide Mixture Comprising Galactosylated and GalNAc-ylated Lactose Structures with a Modified *E. coli* Host An *E. coli* strain optimized for UDP-galactose as described in Example 1, is further modified with a knock-out of the *E. coli* lacZ gene and a knock-in of a constitutive expression unit for the alpha 1,4-galactosyltransferase (LgtC) from *Neisseria gonorrhoeae* (UniProt ID Q50948) to produce alpha-1,4-galactosylated lactose (Gal-a1,4-Gal-b1,4-Glc) when grown on glycerol and lactose. In a next step, the mutant strain is transformed with an expression plasmid comprising constitutive expression units for WbpP of *P. aeruginosa* (UniProt ID Q8KN66) and LgtD from *H. influenzae* (UniProt ID A0A2X4DBP3) ("HiLgtD"). Besides its 01,3-N-Acetyl-galactosaminyltransferase activity, the HiLgtD enzyme also has a 01,3-galactosetransferase activity and can add a galactose to a non-reducing terminal GalNAc molecule resulting in a terminal Gal-b1,3-GalNAc at the non-reducing end of a glycan. The novel strain is evaluated for production of an oligosaccharide mixture comprising Gal-a1,4-Gal-b1,4-Glc (Gal-a1,4-lactose), GalNAc-b1,3-Gal-b1,4-Glc (GalNAc-b 1,3-Lactose), Gal-b 1,3-GalNAc-b 1,3-1 acto se, GalNAc-b 1,3-Gal-a1,4-Gal-b 1,4-Glc (gl ob o-N-tetrao se) and Gal-b 1,3-GalNAc-b1,3-Gal-a1,4-Gal-b1,4-Glc in a growth experiment according to the culture conditions provided in Example 1, in which the culture medium contains glycerol as carbon source and lactose as precursor.

Example 10. Production of an Oligosaccharide Mixture Comprising LN3, LNT, GalNAc-b1,3-LNT, Gal-b1,3-GalNAc-b1,3-LNT, GalNAc-b1,3-lactose and Gal-b1,3-GalNAc-b1,3-lactose with a Modified *E. coli* Host An *E. coli* strain modified to produce LNT as described in Example 1, is further modified with knock-ins of constitutive expression units for WbpP from *P. aeruginosa* (UniProt ID Q8KN66) and LgtD from *H. influenzae* (UniProt ID A0A2X4DBP3). The novel strain is evaluated for production of an oligosaccharide mixture comprising LN3, LNT, GalNAc-b1,3-LNT, Gal-b1,3-GalNAc-b1,3-LNT, GalNAc-b1,3-lactose and Gal-b1,3-GalNAc-b1,3-lactose in whole broth samples in a growth experiment, according to the culture conditions in Example 1, in which the culture medium contains glycerol as carbon source and lactose as precursor.

Example 11. Production an Oligosaccharide Mixture Comprising LN3, LNnT, GalNAc-b1,3-LNnT, Gal-b1,3-GalNAc-b1,3-LNnT, GalNAc-b1,3-lactose, Gal-b1,3-GalNAc-b1,3-lactose and 1GalNAc)-poly-LNnT Structures with a Modified *E. coli* Host An *E. coli* strain modified to produce LNnT as described in Example 1, is further modified with knock-ins of constitutive expression units for WbpP from *P. aeruginosa* (UniProt ID Q8KN66) and LgtD from *H. influenzae* (UniProt ID A0A2X4DBP3). The novel strain is evaluated for production of an oligosaccharide mixture comprising LN3, LNnT, GalNAc-b1,3-LNnT, Gal-b1,3-GalNAc-b1,3-LNnT, GalNAc-b1,3-lacto se and Gal-b1,3-GalNAc-b1,3-lactose as well as poly-LNnT structures (by alternate activity of NmlgtA and NmLgtB) and GalNAc-ylated poly-LNnT structures (by additional activity of HiLgtD) in whole broth samples in a growth experiment, according to the culture conditions in Example 1, in which the culture medium contains glycerol as carbon source and lactose as precursor.

Example 12. Production of an Oligosaccharide Mixture Comprising Gal-a1,3-LacNAc, LN3, LNnT and Gal-a1,3-LNnT with a Modified *E. coli* Host An *E. coli* K-12 MG1655 strain is modified with genomic knock-outs of the *E. coli* lacZ, glk genes and the *E. coli* galETKM operon, together with genomic knock-ins of constitutive transcriptional units for lgtB from *N. meningitidis* (UniProt ID Q51116) and the UDP-glucose 4-epimerase (galE) from *E. coli* (P09147) to produce lactose (Gal-b1,4-Glc). In next steps, the mutant strain is further modified with a knock-out of the *E. coli* nagB gene together with genomic knock-ins of constitutive transcriptional units for the mutant L-glutamine-D-fructose-6-phosphate aminotransferase glmS*54 from *E. coli* (differing from the wild-type glmS (UniProt ID P17169) by an A39T, an R250C and an G472S mutation) and GNA1 from *S. cerevisiae* (UniProt ID P43577) to produce GlcNAc and LacNAc. In a final step, the novel strain is additionally transformed with an expression plasmid containing constitutive transcriptional units for LgtA from *N. meningitidis* (UniProt ID Q9JXQ6) and the C-terminal catalytic domain comprising amino acid residues 80 to 367 of the alpha-1,3-galactosyltransferase (a3FTcd) from *Bos taurus* (UniProt ID P14769). The novel strain is evaluated for production of an oligosaccharide mixture comprising Gal-a1,3-lactose, Gal-a1,3-LacNAc (Gal-a1,3-Gal-b1,4-GlcNAc), LN3, LNnT and Gal-a1,3-LNnT (Gal-a1,3-Gal-b1,4-GlcNAc-b1,3-Gal-b1,4-Glc) in whole broth samples in a growth experiment according to the culture conditions provided in Example 1, in which the culture medium contains glycerol as carbon source.

Example 13. Production of an Oligosaccharide Mixture Comprising LacNAc, GalNAc-b1,3-lactose (b3'-GalNAcL), Gal-b1,3-GalNAc-b1,3-lactose, LN3, LNnT, GalNAc-b1,3-LacNAc, Gal-b1,3-GalNAc-b1,3-LacNAc, poly-LacNAc (Gal-b1,4-GlcNAc)n and GalNAc-ylated poly-LacNAc Structures with a Modified E. coli Host An E. coli K-12 MG1655 strain is modified with genomic knock-outs of the E. coli lacZ, glk genes and the E. coli galETKM operon, together with genomic knock-ins of constitutive transcriptional units for lgtB from N. meningitidis (UniProt ID Q51116) and the UDP-glucose 4-epimerase (galE) from E. coli (UniProt ID P09147) to produce lactose (Gal-b1,4-Glc). In next steps, the mutant strain is further modified with a knock-out of the E. coli nagB gene together with genomic knock-ins of constitutive transcriptional units for the mutant L-glutamine-D-fructose-6-phosphate aminotransferase glmS*54 from E. coli (differing from the wild-type glmS (UniProt ID P17169) by an A39T, an R250C and an G472S mutation and GNA1 from S. cerevisiae (UniProt ID P43577) to produce GlcNAc and LacNAc. In a final step, the novel strain is additionally transformed with an expression plasmid containing constitutive transcriptional units for WbpP of P. aeruginosa (UniProt ID Q8KN66), LgtA from N. meningitidis (UniProt ID Q9JXQ6) and LgtD from H. influenzae (UniProt ID A0A2X4DBP3). The novel strain is evaluated for production of an oligosaccharide mixture comprising LacNAc, LN3, LNnT, GalNAc-b1,3-lactose, Gal-b1,3-GalNAc-b1,3-lactose, GalNAc-b1,3-Gal-b1,4-GlcNAc-b1,3-Gal-b1,4-Glc, GalNAc-b1,3-LacNAc, Gal-b1,3-GalNAc-b1,3-LacNAc, poly-LacNAc structures, i.e. (Gal-b1,4-GlcNAc)n and GalNAc-ylated poly-LacNAc structures in a growth experiment according to the culture conditions provided in Example 1, in which the culture medium comprises glycerol as carbon source.

Example 14. Production of an Oligosaccharide Mixture Comprising Galactosylated and GalNAc-ylated Lactose Structures with a Modified E. coli Host An E. coli K-12 MG1655 strain is modified with genomic knock-outs of the E. coli nagB, ushA, galT, lacZ, glk genes and the E. coli galETKM operon, together with genomic knock-ins of constitutive transcriptional units for lgtB from N. meningitidis (UniProt ID Q51116), galE from E. coli (UniProt ID P09147), the a1,4-galactosyltransferase (LgtC) from N. gonorrhoeae (UniProt ID Q50948) and the mutant L-glutamine-D-fructose-6-phosphate aminotransferase glmS*54 from E. coli (differing from the wild-type glmS (UniProt ID P17169) by an A39T, an R250C and an G472S mutation. In a next step, the mutant strain is transformed with an expression plasmid comprising constitutive expression units for WbpP of P. aeruginosa (UniProt ID Q8KN66) and LgtD from H. influenzae (UniProt ID A0A2X4DBP3). The novel strain is evaluated for production of an oligosaccharide mixture comprising Gal-a1,4-Gal-b1,4-Glc (Gal-a1,4-lactose), Gal-a1,4-Gal-a1,4-Gal-b1,4-Glc, Gal-a1,4-Gal-a1,4-Gal-a1,4-Gal-b1,4-Glc, GalNAc-b1,3-Gal-b1,4-Glc (GalNAc-b1,3-Lactose), Gal-b1,3-GalNAc-b1,3-lactose, GalNAc-b1,3-Gal-a1,4-Gal-b1,4-Glc (globo-N-tetraose) and Gal-b1,3-GalNAc-b1,3-Gal-a1,4-Gal-b1,4-Glc in a growth experiment according to the culture conditions provided in Example 1, in which the culture medium contains glycerol as carbon source.

Example 15. Production an Oligosaccharide Mixture Comprising LN3, LNnT, GalNAc-b1,3-LNnT, Gal-b1,3-GalNAc-b1,3-LNnT, GalNAc-b1,3-lactose, Gal-b1,3-GalNAc-b1,3-lactose and 1GalNAc)-poly-LNnT Structures with a Modified E. coli Host An E. coli K-12 MG1655 strain is modified with genomic knock-outs of the E. coli nagB, lacZ, glk genes and the E. coli galETKM operon, together with genomic knock-ins of constitutive transcriptional units for lgtB from N. meningitidis (UniProt ID Q51116), galE from E. coli (UniProt ID P09147), lgtA from N. meningitidis (UniProt ID Q9JXQ6), the mutant L-glutamine-D-fructose-6-phosphate aminotransferase glmS*54 from E. coli (differing from the wild-type glmS (UniProt ID P17169) by an A39T, an R250C and an G472S mutation, WbpP from P. aeruginosa (UniProt ID Q8KN66) and LgtD from H. influenzae (UniProt ID A0A2X4DBP3). The novel strain is evaluated for production of an oligosaccharide mixture comprising LN3, LNnT, GalNAc-b1,3-LNnT, Gal-b1,3-GalNAc-b1,3-LNnT, GalNAc-b1,3-lactose and Gal-b1,3-GalNAc-b1,3-lactose as well as poly-LNnT structures and GalNAc-ylated poly-LNnT structures in whole broth samples in a growth experiment, according to the culture conditions in Example 1, in which the culture medium contains glycerol as carbon source.

Example 16. Production of an Oligosaccharide Mixture Comprising GlcNAc-b1,3-Gal-b1,4-GlcNAc and poly-LacNAc (Gal-b1,4-GlcNAc)n Structures with a Modified S. cerevisiae Host An S. cerevisiae strain is transformed with a yeast expression pRS420-plasmid containing the HIS3 selection marker and comprising constitutive transcriptional units for the mutant L-glutamine-D-fructose-6-phosphate aminotransferase glmS*54 from E. coli (differing from the wild-type glmS (UniProt ID P17169) by an A39T, an R250C and an G472S mutation, the phosphatase yqaB from E. coli (UniProt ID NP_417175.1), galE from E. coli (UniProt ID P09147), LgtA from N. meningitidis (UniProt ID Q9JXQ6) and LgtB from N. meningitidis (UniProt ID Q51116). The mutant yeast strain is evaluated for production of an oligosaccharide mixture comprising LacNAc, GlcNAc-b1,3-Gal-b1,4-GlcNAc and poly-LacNAc structures (Gal-b1,4-GlcNAc)n in a growth experiment according to the culture conditions in Example 1, using SD CSM-Ura-His drop-out medium.

Example 17. Production of an Oligosaccharide Mixture Comprising GlcNAc-b1,3-Gal-b1,4-GlcNAc, beta-Gal-(1,4)-beta-GlcNAc-(1,3)-[beta-GlcNAc-(1,6)]-beta-Gal-(1,4)-GlcNAc and poly-LacNAc Structures with a Modified S. cerevisiae Host An S. cerevisiae strain is transformed with a yeast expression pRS420-plasmid containing the HIS3 selection marker and comprising constitutive transcriptional units for the mutant glmS*54 from E. coli (differing from the wild-type glmS (UniProt ID P17169) by an A39T, an R250C and an G472S mutation, the phosphatase yqaB from E. coli (UniProt ID NP_417175.1), galE from E. coli (UniProt ID P09147), LgtA from N. meningitidis (UniProt ID Q9JXQ6), LgtB from N. meningitidis (UniProt ID Q51116) and the human N-acetyllactosaminide beta-1,6-N-acetylglucosaminyltransferase GCNT2 (UniProt ID Q8NOV5). The mutant yeast strain is evaluated for production of an oligosaccharide mixture comprising LacNAc, GlcNAc-b1,3-Gal-b1,4-GlcNAc, GlcNAc-b1,6-Gal-b1,4-GlcNAc, (Gal-b1,4-GlcNAc)n structures and beta-Gal-(1,4)-beta-GlcNAc-(1,3)-[beta-GlcNAc-(1,6)]-beta-Gal-(1,4)-GlcNAc in a growth experiment according to the culture conditions in Example 1, using SD CSM-Ura-His drop-out medium.

Example 18. Production of an Oligosaccharide Mixture Comprising Gal-a1,3-LacNAc, LN3, LNnT and Gal-a1,3-LNnT with a Modified S. cerevisiae Host An S. cerevisiae strain is transformed with a yeast expression pRS420-plasmid containing the HIS3 selection marker and comprising constitutive transcriptional units for the mutant glmS*54 from E. coli (differing from the wild-type glmS (UniProt ID P17169) by an A39T, an R250C and an G472S mutation, the phosphatase yqaB from E. coli (UniProt ID NP_417175.1), galE from E. coli (UniProt ID P09147), LgtA from N. meningitidis (UniProt ID Q9JXQ6), LgtB from N. meningitidis (UniProt ID Q51116) and the C-terminal catalytic domain comprising amino acid residues 80 to 367 of the alpha-1,3-galactosyltransferase (a3FTcd) from Bos taurus (UniProt ID P14769). The mutant yeast strain is evaluated for production of an oligosaccharide mixture comprising Gal-a1,3-LacNAc (Gal-a1,3-Gal-b1,4-GlcNAc), LN3, LNnT and Gal-a1,3-LNnT (Gal-a1,3-Gal-b1,4-GlcNAc-b1,3-Gal-b1,4-Glc) in a growth experiment according to the culture conditions in Example 1, using SD CSM-Ura-His drop-out medium.

Example 19. Production of an Oligosaccharide Mixture Comprising LacNAc, GalNAc-b1,3-lactose, Gal-b1,3-GalNAc-b1,3-lactose, LN3, LNnT, GalNAc-b1,3-LacNAc, Gal-b1,3-GalNAc-b1,3-LacNAc, poly-LacNAc (Gal-b1,4-GlcNAc)n and GalNAc-ylated poly-LacNAc Structures with a Modified S. cerevisiae Host An S. cerevisiae strain is transformed with a yeast artificial chromosome (YAC) comprising constitutive transcriptional units for the mutant glmS*54 from E. coli (differing from the wild-type glmS (UniProt ID P17169) by an A39T, an R250C and an G472S mutation, the phosphatase yqaB from E. coli (UniProt ID NP_417175.1), galE from E. coli (UniProt ID P09147), LgtA from N. meningitidis (UniProt ID Q9JXQ6), LgtB from N. meningitidis (UniProt ID Q51116), WbpP from P. aeruginosa (UniProt ID Q8KN66) and LgtD from H. influenzae (UniProt ID A0A2X4DBP3). The mutant yeast strain is evaluated for production of an oligosaccharide mixture comprising LacNAc, LN3, LNnT, GalNAc-b1,3-lactose, Gal-b1,3-GalNAc-b1,3-lactose, GalNAc-b1,3-Gal-b1,4-GlcNAc-b1,3-Gal-b1,4-Glc, GalNAc-b1,3-LacNAc, Gal-b1,3-GalNAc-b1,3-LacNAc, poly-LacNAc structures, i.e. (Gal-b1,4-GlcNAc)n and GalNAc-ylated poly-LacNAc structures in a growth experiment according to the culture conditions in Example 1, using SD CSM medium comprising lactose.

Example 20. Production of an Oligosaccharide Mixture Comprising LNB, LN3, LNT, GalNAc-b1,3-lactose, Gal-b1,3-GalNAc-b1,3-lactose, GalNAc-b1,3-LNB and Gal-b1,3-GalNAc-b1,3-LNB with a Modified S. cerevisiae Host An S. cerevisiae strain is transformed with a YAC comprising constitutive transcriptional units for the mutant glmS*54 from E. coli (differing from the wild-type glmS (UniProt ID P17169) by an A39T, an R250C and an G472S mutation, the phosphatase yqaB from E. coli (UniProt ID NP_417175.1), WbgO from E. coli O55:H7 (UniProt ID D3QY14), WbpP of P. aeruginosa (UniProt ID Q8KN66), LgtA from N. meningitidis (UniProt ID Q9JXQ6) and LgtD from H. influenzae (UniProt ID A0A2X4DBP3). The mutant yeast strain is evaluated for production of an oligosaccharide mixture comprising LNB, LN3, LNT, GalNAc-b1,3-lactose, Gal-b1,3-GalNAc-b1,3-lactose, GalNAc-b1,3-Gal-b1,3-GlcNAc-b1,3-Gal-b1,4-Glc, GalNAc-b1,3-LNB and Gal-b1,3-GalNAc-b1,3-LNB in a growth experiment according to the culture conditions in Example 1, using SD CSM medium comprising lactose.

Example 21. Production of an Oligosaccharide Mixture Comprising Galactosylated and GalNAc-ylated Lactose Structures with a Modified S. cerevisiae Host An S. cerevisiae strain is transformed with a YAC comprising constitutive transcriptional units for the mutant glmS*54 from E. coli (differing from the wild-type glmS (UniProt ID P17169) by an A39T, an R250C and an G472S mutation, the phosphatase yqaB from E. coli (UniProt ID NP_417175.1), galE from E. coli (UniProt ID P09147), WbpP of P. aeruginosa (UniProt ID Q8KN66), LgtA from N. meningitidis (UniProt ID Q9JXQ6) and LgtD from H. influenzae (A0A2X4DBP3), the a1,4-galactosyltransferase (LgtC) from N. gonorrhoeae (UniProt ID Q50948). The mutant yeast strain is evaluated for production of an oligosaccharide mixture comprising Gal-a1,4-Gal-b1,4-Glc (Gal-a1,4-lactose), Gal-a1,4-Gal-a1,4-Gal-b1,4-Glc, Gal-a1,4-Gal-a1,4-Gal-a1,4-Gal-b1,4-Glc, GalNAc-b1,3-Gal-b1,4-Glc (GalNAc-b1,3-Lactose), Gal-b1,3-GalNAc-b1,3-lactose, GalNAc-b1,3-Gal-a1,4-Gal-b1,4-Glc (globo-N-tetraose) and Gal-b1,3-GalNAc-b1,3-Gal-a1,4-Gal-b1,4-Glc in a growth experiment according to the culture conditions in Example 1, using SD CSM medium comprising lactose.

Example 22. Production of an Oligosaccharide Mixture Comprising LN3, LNT, GalNAc-b1,3-LNT, Gal-b1,3-GalNAc-b1,3-LNT, GalNAc-b1,3-lactose and Gal-b1,3-GalNAc-b1,3-lactose with a Modified S. cerevisiae Host An S. cerevisiae strain is transformed with a YAC comprising constitutive transcriptional units for the mutant glmS*54 from E. coli (differing from the wild-type glmS (UniProt ID P17169) by an A39T, an R250C and an G472S mutation, LgtA from N. meningitidis (UniProt ID Q9JXQ6), WbgO from E. coli O55:H7 (UniProt ID D3QY14), WbpP from P. aeruginosa (UniProt ID Q8KN66) and LgtD from H. influenzae (UniProt ID A0A2X4DBP3). The mutant yeast strain is evaluated for production of an oligosaccharide mixture comprising LN3, LNT, GalNAc-b1,3-LNT, Gal-b1,3-GalNAc-b1,3-LNT, GalNAc-b1,3-lactose and Gal-b1,3-GalNAc-b1,3-lactose in a growth experiment according to the culture conditions in Example 1, using SD CSM medium comprising lactose.

Example 23. Production an Oligosaccharide Mixture Comprising LN3, LNnT, GalNAc-b1,3-LNnT, Gal-b1,3-GalNAc-b1,3-LNnT, GalNAc-b1,3-lactose, Gal-b1,3-GalNAc-b1,3-lactose and 1GalNAc)-poly-LNnT Structures with a Modified S. cerevisiae Host An S. cerevisiae strain is transformed with a YAC comprising constitutive transcriptional units for the mutant glmS*54 from *E. coli* (differing from the wild-type glmS (UniProt ID P17169) by an A39T, an R250C and an G472S mutation, LgtA from *N. meningitidis* (UniProt ID Q9JXQ6), LgtB from *N. meningitidis* (UniProt ID Q51116), WbpP from *P. aeruginosa* (UniProt ID Q8KN66) and LgtD from *H. influenzae* (UniProt ID A0A2X4DBP3). The mutant yeast strain is evaluated for production of an oligosaccharide mixture comprising LN3, LNnT, GalNAc-b1,3-LNnT, Gal-b1,3-GalNAc-b1,3-LNnT, GalNAc-b1,3-lactose and Gal-b1,3-GalNAc-b1,3-lactose as well as poly-LNnT structures and GalNAc-ylated poly-LNnT structures in a growth experiment according to the culture conditions in Example 1, using SD CSM medium comprising lactose.

Example 24. Material and Methods *Bacillus subtilis*

Media

Two different media are used, namely a rich Luria Broth (LB) and a minimal medium for shake flask (MMsf). The minimal medium uses a trace element mix.

Trace element mix consisted of 0.735 g/L CaCl2·2H2O, 0.1 g/L MnCl2·2H2O, 0.033 g/L CuCl2·2H2O, 0.06 g/L CoCl2·6H2O, 0.17 g/L ZnCl2, 0.0311 g/L H3B04, 0.4 g/L Na2EDTA·2H2O and 0.06 g/L Na2MoO4. The Fe-citrate solution contained 0.135 g/L FeCl3·6H2O, 1 g/L Na-citrate (Hoch 1973 PMC1212887).

The Luria Broth (LB) medium consisted of 1% tryptone peptone (Difco, Erembodegem, Belgium), 0.5% yeast extract (Difco) and 0.5% sodium chloride (VWR, Leuven, Belgium). Luria Broth agar (LBA) plates consisted of the LB media, with 12 g/L agar (Difco, Erembodegem, Belgium) added.

The minimal medium for the shake flasks (MMsf) experiments contained 2.00 g/L (NH4)2SO4, 7.5 g/L KH2PO4, 17.5 g/L K2HPO4, 1.25 g/L Na-citrate, 0.25 g/L MgSO4·7H2O, 0.05 g/L tryptophan, from 10 up to 30 g/L glucose or another carbon source including but not limited to fructose, maltose, sucrose, glycerol and maltotriose when specified in the examples, 10 ml/L trace element mix and 10 ml/L Fe-citrate solution. The medium was set to a pH of 7 with 1 M KOH. Depending on the experiment lactose, LNB or LacNAc could be added as a precursor.

Complex medium, e.g., LB, was sterilized by autoclaving (121° C., 21') and minimal medium by filtration (0.22 µm Sartorius). When necessary, the medium was made selective by adding an antibiotic (e.g., zeocin (20 mg/L)).

Strains, Plasmids and Mutations

*Bacillus subtilis* 168, available at *Bacillus* Genetic Stock Center (Ohio, USA).

Plasmids for gene deletion via Cre/lox are constructed as described by Yan et al. (Appl. & Environm. Microbial., September 2008, pages 5556-5562). Gene disruption is done via homologous recombination with linear DNA and transformation via electroporation as described by Xue et al. (J. Microb. Meth. 34 (1999) 183-191). The method of gene knockouts is described by Liu et al. (Metab. Engine. 24 (2014) 61-69). This method uses 1000 bp homologies up- and downstream of the target gene.

Integrative vectors as described by Popp et al. (Sci. Rep., 2017, 7, 15158) are used as expression vector and could be further used for genomic integrations if necessary. A suitable promoter for expression can be derived from the part repository (iGem): sequence id: Bba_K143012, Bba_K823000, Bba_K823002 or Bba_K823003. Cloning can be performed using Gibson Assembly, Golden Gate assembly, Cliva assembly, LCR or restriction ligation.

In an example for the production of lactose-based oligosaccharides, *Bacillus subtilis* mutant strains are created to contain a gene coding for a lactose importer (such as the *E. coli* lacY with UniProt ID P02920).

In an example to produce lactose (Gal-b1,4-Glc), a *Bacillus subtilis* strain is modified with genomic knock-outs of the lacZ, glk, galE, galT, galK and galM genes, together with genomic knock-ins of constitutive transcriptional units for an N-acetylglucosamine beta-1,4-galactosyltransferase like, e.g., lgtB from *N. meningitidis* (UniProt ID Q51116) and a UDP-glucose 4-epimerase like, e.g., galE from *E. coli* (UniProt ID P09147).

In an example to produce lacto-N-triose (LN3, LNT-II, GlcNAc-b1,3-Gal-b1,4-Glc) and neutral non-fucosylated oligosaccharides originating thereof comprising lacto-N-tetraose (LNT) and lacto-N-neotetraose (LNnT), a *Bacillus subtilis* strain is modified with a knock-out of the LacZ and nagB genes and with a genomic knock-in of a constitutive transcriptional unit for a galactoside beta-1,3-N-acetylglucosaminyltransferase like, e.g., LgtA from *N. meningitidis* (UniProt ID Q9JXQ6). For LNT or LNnT production, the mutant strain is further modified with constitutive transcriptional units for an N-acetylglucosamine beta-1,3-galactosyltransferase like, e.g., WbgO from *E. coli* O55:H7 (UniProt ID D3QY14) or an N-acetylglucosamine beta-1,4-galactosyltransferase like, e.g., LgtB from *N. meningitidis* (UniProt ID Q51116), respectively, that can be delivered to the strain either via genomic knock-in or from an expression plasmid.

Heterologous and Homologous Expression

Genes that needed to be expressed, be it from a plasmid or from the genome were synthetically synthetized with one of the following companies: DNA2.0, Gen9, Twist Biosciences or IDT.

Expression could be further facilitated by optimizing the codon usage to the codon usage of the expression host. Genes were optimized using the tools of the supplier.

Cultivation Conditions

A preculture of 96-well microtiter plate experiments was started from a cryovial or a single colony from an LB plate, in 150 µL LB and was incubated overnight at 37° C. on an orbital shaker at 800 rpm. This culture was used as inoculum for a 96-well square microtiter plate, with 400 µL MMsf medium by diluting 400×. Each strain was grown in multiple wells of the 96-well plate as biological replicates. These final 96-well culture plates were then incubated at 37° C. on an orbital shaker at 800 rpm for 72 h, or shorter, or longer. At the end of the cultivation experiment samples were taken from each well to measure the supernatant concentration (extracellular sugar concentrations, after 5 min. spinning down the cells), or by boiling the culture broth for 15 min at 90° C. or for 60 min at 60° C. before spinning down the cells (=whole broth concentration, intra- and extracellular sugar concentrations, as defined herein).

Also, a dilution of the cultures was made to measure the optical density at 600 nm. The cell performance index or CPI was determined by dividing the oligosaccharide concentrations by the biomass, in relative percentages compared to a reference strain. The biomass is empirically determined to be approximately ⅓rd of the optical density measured at 600 nm.

Example 25. Production of an Oligosaccharide Mixture Comprising LN3, LNnT, GalNAc-b1,3-LNnT, Gal-b1,3-GalNAc-b1,3-LNnT, GalNAc-b1,3-lactose, Gal-b1,3-GalNAc-b1,3-lactose and 1GalNAc)-poly-LNnT with a Modified *B. subtilis* Strain A *B. subtilis* strain is first modified by genomic knock-out of the lacZ, nagB, gamA, glk, galE, galT, galK and galM genes and genomic knock-ins of constitutive transcriptional units comprising genes encoding the lactose permease (LacY) from *E. coli* (UniProt ID P02920), the native fructose-6-P-aminotransferase (UniProt ID P0CI73), the sucrose transporter (CscB) from *E. coli* W (UniProt ID E0IXR1), the fructose kinase (Frk) from *Z. mobilis* (UniProt ID Q03417) and the sucrose phosphorylase (BaSP) from *B. adolescentis* (UniProt ID A0ZZH6). The thus obtained mutant strain is further modified with genomic knock-ins of constitutive transcriptional units comprising lgtB from *N. meningitidis* (UniProt ID Q51116), galE from *E. coli* (UniProt ID P09147), lgtA from *N. meningitidis* (UniProt ID Q9JXQ6), the mutant L-glutamine-D-fructose-6-phosphate aminotransferase glmS*54 from *E. coli* (differing from the wild-type glmS (UniProt ID P17169) by an A39T, an R250C and an G472S mutation, WbpP from *P. aeruginosa* (UniProt ID Q8KN66) and LgtD from *H. influenzae* (UniProt ID A0A2X4DBP3). The novel strain is evaluated for production of an oligosaccharide mixture comprising LN3, LNnT, GalNAc-b1,3-LNnT, Gal-b1,3-GalNAc-b1,3-LNnT, Gal-NAc-b1,3-lactose and Gal-b1,3-GalNAc-b1,3-lactose as well as poly-LNnT structures and GalNAc-ylated poly-LNnT structures in a growth experiment on MMsf medium comprising lactose as precursor according to the culture conditions provided in Example 24.

Example 26. Production of an Oligosaccharide Mixture Comprising LacNAc, GalNAc-b1,3-lactose, Gal-b1,3-GalNAc-b1,3-lactose, LN3, LNnT, GalNAc-b1,3-LacNAc, Gal-b1,3-GalNAc-b1,3-LacNAc, poly-LacNAc (Gal-b1,4-GlcNAc)n and GalNAc-ylated poly-LacNAc Structures with a Modified *B. subtilis* Strain A *B. subtilis* strain is first modified by genomic knock-out of the lacZ, nagB, gamA, glk, galE, galT, galK and galM genes and genomic knock-ins of constitutive transcriptional units comprising genes encoding the lactose permease (LacY) from *E. coli* (UniProt ID P02920), the native fructose-6-P-aminotransferase (UniProt ID P0CI73), the mutant L-glutamine-D-fructose-6-phosphate aminotransferase glmS*54 from *E. coli* (differing from the wild-type glmS (UniProt ID P17169) by an A39T, an R250C and an G472S mutation), GNA1 from *S. cerevisiae* (UniProt ID UniProt ID P43577), the phosphatase yqaB from *E. coli* (UniProt ID NP_417175.1), the galactoside beta-1,3-N-acetylglucosaminyltransferase (LgtA) from *N. meningitidis* (UniProt ID Q9JXQ6), LgtB from *N. meningitidis* (UniProt ID Q51116), the 4-epimerase (WbpP) of *Pseudomonas aeruginosa* (UniProt ID Q8KN66) and the β1,3-N-acetylgalactosaminyltransferase (LgtD) from *Haemophilus influenzae* (UniProt ID A0A2X4DBP3). The novel strain is evaluated for production of an oligosaccharide mixture comprising LacNAc, LN3, LNnT, GalNAc-b1,3-lactose, Gal-b1,3-GalNAc-b1,3-lactose, GalNAc-b1,3-Gal-b1,4-GlcNAc-b1,3-Gal-b1,4-Glc, GalNAc-b1,3-LacNAc, Gal-b1,3-GalNAc-b1,3-LacNAc, poly-LacNAc structures, i.e. (Gal-b1,4-GlcNAc)n and GalNAc-ylated poly-LacNAc structures, in a growth experiment on MMsf medium comprising lactose as precursor according to the culture conditions provided in Example 24.

Example 27. Material and Methods
*Corynebacterium glutamicum*

Media

Two different media are used, namely a rich tryptone-yeast extract (TY) medium and a minimal medium for shake flask (MMsf). The minimal medium uses a 1000× stock trace element mix.

Trace element mix consisted of 10 g/L CaCl2, 10 g/L FeSO4·7H2O, 10 g/L MnSO4·H2O, 1 g/L ZnSO4·7H2O, 0.2 g/L CuSO4, 0.02 g/L NiCl2·6H2O, 0.2 g/L biotin (pH 7.0) and 0.03 g/L protocatechuic acid.

The minimal medium for the shake flasks (MMsf) experiments contained 20 g/L (NH4)2SO4, 5 g/L urea, 1 g/L KH2PO4, 1 g/L K2HPO4, 0.25 g/L MgSO4·7H2O, 42 g/L MOPS, from 10 up to 30 g/L glucose or another carbon source including but not limited to fructose, maltose, sucrose, glycerol and maltotriose when specified in the examples and 1 ml/L trace element mix. Depending on the experiment lactose, LNB or LacNAc could be added as a precursor.

The TY medium consisted of 1.6% tryptone (Difco, Erembodegem, Belgium), 1% yeast extract (Difco) and 0.5% sodium chloride (VWR. Leuven, Belgium). TY agar (TYA) plates consisted of the TY media, with 12 g/L agar (Difco, Erembodegem, Belgium) added.

Complex medium, e.g., TY, was sterilized by autoclaving (121° C., 21') and minimal medium by filtration (0.22 µm Sartorius). When necessary, the medium was made selective by adding an antibiotic (e.g., kanamycin, ampicillin).

Strains and Mutations

*Corynebacterium glutamicum* ATCC 13032, available at the American Type Culture Collection.

Integrative plasmid vectors based on the Cre/loxP technique as described by Suzuki et al. (Appl. Microbiol. Biotechnol., 2005 April, 67(2):225-33) and temperature-sensitive shuttle vectors as described by Okibe et al. (Journal of Microbiological Methods 85, 2011, 155-163) are constructed for gene deletions, mutations and insertions. Suitable promoters for (heterologous) gene expression can be derived from Yim et al. (Biotechnol. Bioeng., 2013 November, 110(11):2959-69). Cloning can be performed using Gibson Assembly, Golden Gate assembly, Cliva assembly, LCR or restriction ligation.

In an example for the production of lactose-based oligosaccharides, *C. glutamicum* mutant strains are created to contain a gene coding for a lactose importer (such as the *E. coli* lacY with UniProt ID P02920).

In an example to produce lactose (Gal-b1,4-Glc), a *C. glutamicum* strain is modified with genomic knock-ins of constitutive transcriptional units for an N-acetylglucosamine beta-1,4-galactosyltransferase like, e.g., lgtB from *N. meningitidis* (UniProt ID Q51116) and a UDP-glucose 4-epimerase like, e.g., galE from *E. coli* (UniProt ID P09147).

In an example to produce lacto-N-triose (LN3, LNT-II, GlcNAc-b1,3-Gal-b1,4-Glc) and neutral non-fucosylated oligosaccharides originating thereof comprising lacto-N-tetraose (LNT) and lacto-N-neotetraose (LNnT), a *C. glutamicum* strain is modified with a genomic knock-in of a constitutive transcriptional unit for a galactoside beta-1,3-N-acetylglucosaminyltransferase like, e.g., LgtA from *N. meningitidis* (UniProt ID Q9JXQ6). For LNT or LNnT production, the mutant strain is further modified with constitutive transcriptional units for an N-acetylglucosamine beta-1,3-galactosyltransferase like, e.g., WbgO from *E. coli* O55:H7 (UniProt ID D3QY14) or an N-acetylglucosamine beta-1,4-galactosyltransferase like, e.g., LgtB from *N. men-*

*ingitidis* (UniProt ID Q51116), respectively, that can be delivered to the strain either via genomic knock-in or from an expression plasmid.

Heterologous and Homologous Expression

Genes that needed to be expressed, be it from a plasmid or from the genome were synthetically synthetized with one of the following companies: DNA2.0, Gen9, Twist Biosciences or IDT.

Expression could be further facilitated by optimizing the codon usage to the codon usage of the expression host. Genes were optimized using the tools of the supplier.

Cultivation Conditions

A preculture of 96-well microtiter plate experiments was started from a cryovial or a single colony from a TY plate, in 150 µL TY and was incubated overnight at 37° C. on an orbital shaker at 800 rpm. This culture was used as inoculum for a 96-well square microtiter plate, with 400 µL MMsf medium by diluting 400×. Each strain was grown in multiple wells of the 96-well plate as biological replicates. These final 96-well culture plates were then incubated at 37° C. on an orbital shaker at 800 rpm for 72 h, or shorter, or longer. At the end of the cultivation experiment samples were taken from each well to measure the supernatant concentration (extracellular sugar concentrations, after 5 min. spinning down the cells), or by boiling the culture broth for 15 min at 60° C. before spinning down the cells (=whole broth concentration, intra- and extracellular sugar concentrations, as defined herein).

Also, a dilution of the cultures was made to measure the optical density at 600 nm. The cell performance index or CPI was determined by dividing the oligosaccharide concentrations, e.g., sialyllactose concentrations, measured in the whole broth by the biomass, in relative percentages compared to the reference strain. The biomass is empirically determined to be approximately ⅓rd of the optical density measured at 600 nm.

Example 28. Production of an Oligosaccharide Mixture Comprising LNB, LN3, LNT, GalNAc-b1, 3-lactose, Gal-b1,3-GalNAc-b1,3-lactose, GalNAc-b1,3-LNB and Gal-b1,3-GalNAc-b1,3-GalNAc-b1, 3-LNB in Mutant *C. glutamicum* Strains A wild-type *C. glutamicum* strain is first modified with genomic knockouts of the *C. glutamicum* genes ldh, cg12645, nagB, gamA and nagA, together with genomic knock-ins of constitutive transcriptional units comprising genes encoding the phosphatase yqaB from *E. coli* (UniProt ID NP_417175.1), GNA1 from *S. cerevisiae* (UniProt ID P43577) and WbgO from *E. coli* O55:H7 (UniProt ID D3QY14) to produce LNB. In a next step, the LNB producing is further modified with knock-ins of constitutive expression units for the 4-epimerase (WbpP) of *P. aeruginosa* (UniProt ID Q8KN66), the galactoside beta-1,3-N-acetylglucosaminyltransferase (LgtA) from *N. meningitidis* (UniProt ID Q9JXQ6) and the β1,3-N-acetylgalactosaminyltransferase (LgtD) from *H. influenzae* (UniProt ID A0A2X4DBP3). The novel strain is evaluated for production of an oligosaccharide mixture comprising LNB, LN3, LNT, GalNAc-b1,3-lacto se, Gal-b1,3-GalNAc-b1,3-lactose, GalNAc-b1,3-Gal-b1,3-GlcNAc-b1,3-Gal-b1,4-Glc, GalNAc-b1,3-LNB and Gal-b1,3-GalNAc-b1,3-LNB in a growth experiment on MMsf medium comprising lactose as precursor according to the culture conditions provided in Example 27.

Example 29. Materials and Methods *Chlamydomonas reinhardtii*

Media

*C. reinhardtii* cells were cultured in Tris-acetate-phosphate (TAP) medium (pH 7.0). The TAP medium uses a 1000× stock Hutner's trace element mix. Hutner's trace element mix consisted of 50 g/L Na2EDTA·H2O (Titriplex III), 22 g/L ZnSO4·7H2O, 11.4 g/L H3B03, 5 g/L MnCl2·4H2O, 5 g/L FeSO4·7H2O, 1.6 g/L CoCl2·6H2O, 1.6 g/L CuSO4·5H2O and 1.1 g/L (NH4)6MoO3.

The TAP medium contained 2.42 g/L Tris (tris(hydroxymethyl)aminomethane), 25 mg/L salt stock solution, 0.108 g/L K2HPO4, 0.054 g/L KH2PO4 and 1.0 mL/L glacial acetic acid. The salt stock solution consisted of 15 g/L NH4CL, 4 g/L MgSO4·7H2O and 2 g/L CaCl2·2H2O. As precursor for saccharide synthesis, precursors like, e.g., galactose, glucose, fructose, fucose, GlcNAc could be added. Medium was sterilized by autoclaving (121° C., 21'). For stock cultures on agar slants TAP medium was used containing 1% agar (of purified high strength, 1000 g/cm2).

Strains, Plasmids and Mutations

*C. reinhardtii* wild-type strains 21 gr (CC-1690, wild-type, mt+), 6145C (CC-1691, wild-type, mt—), CC-125 (137c, wild-type, mt+), CC-124 (137c, wild-type, mt—) as available from *Chlamydomonas* Resource Center online, University of Minnesota, U.S.A.

Expression plasmids originated from pSI103, as available from *Chlamydomonas* Resource Center. Cloning can be performed using Gibson Assembly, Golden Gate assembly, Cliva assembly, LCR or restriction ligation. Suitable promoters for (heterologous) gene expression can be derived from, e.g., Scranton et al. (Algal Res. 2016, 15: 135-142). Targeted gene modification (like gene knock-out or gene replacement) can be carried using the Crispr-Cas technology as described, e.g., by Jiang et al. (Eukaryotic Cell 2014, 13(11): 1465-1469).

Transformation via electroporation was performed as described by Wang et al. (Biosci. Rep. 2019, 39: BSR2018210). Cells were grown in liquid TAP medium under constant aeration and continuous light with a light intensity of 8000 Lx until the cell density reached $1.0-2.0 \times 10^7$ cells/mL. Then, the cells were inoculated into fresh liquid TAP medium in a concentration of $1.0 \times 10^6$ cells/mL and grown under continuous light for 18-20 h until the cell density reached $4.0 \times 10^6$ cells/mL. Next, cells were collected by centrifugation at 1250 g for 5 min at room temperature, washed and resuspended with pre-chilled liquid TAP medium containing 60 mM sorbitol (Sigma, U.S.A.), and iced for 10 min. Then, 250 µL of cell suspension (corresponding to $5.0 \times 10^7$ cells) were placed into a pre-chilled 0.4 cm electroporation cuvette with 100 ng plasmid DNA (400 ng/mL). Electroporation was performed with 6 pulses of 500 V each having a pulse length of 4 ms and pulse interval time of 100 ms using a BTX ECM830 electroporation apparatus (1575Ω, 50 µFD). After electroporation, the cuvette was immediately placed on ice for 10 min. Finally, the cell suspension was transferred into a 50 ml conical centrifuge tube containing 10 mL of fresh liquid TAP medium with 60 mM sorbitol for overnight recovery at dim light by slowly shaking. After overnight recovery, cells were recollected and plated with starch embedding method onto selective 1.5% (w/v) agar-TAP plates containing ampicillin (100 mg/L) or chloramphenicol (100 mg/L). Plates were then incubated at 23+–0.5° C. under continuous illumination with a light intensity of 8000 Lx. Cells were analyzed 5-7 days later.

In an example for production of UDP-galactose, *C. reinhardtii* cells are modified with transcriptional units comprising the genes encoding a galactokinase like, e.g., from *Arabidopsis thaliana* (KIN, UniProt ID Q9SEE5) and a UDP-sugar pyrophosphorylase like, e.g., USP from *A. thaliana* (UniProt ID Q9C5I1).

In an example for LN3 production, a constitutive transcriptional unit comprising a galactoside beta-1,3-N-acetylglucosaminyltransferase like, e.g., lgtA from *N. meningitidis* (UniProt ID Q9JXQ6) is additionally added to the strain. In an example for LNT production, the LN3 producing strain is further modified with a constitutive transcriptional unit comprising an N-acetylglucosamine beta-1,3-galactosyltransferase like, e.g., WbgO from *E. coli* O55:H7 (UniProt ID D3QY14). In an example for LNnT production, the LN3 producing strain is further modified with a constitutive transcriptional unit comprising an N-acetylglucosamine beta-1,4-galactosyltransferase like, e.g., lgtB from *N. meningitidis* (UniProt ID Q51116).

Heterologous and Homologous Expression

Genes that needed to be expressed, be it from a plasmid or from the genome were synthetically synthetized with one of the following companies: DNA2.0, Gen9, Twist Biosciences or IDT.

Expression could be further facilitated by optimizing the codon usage to the codon usage of the expression host. Genes were optimized using the tools of the supplier.

Cultivation Conditions

Cells of *C. reinhardtii* were cultured in selective TAP-agar plates at 23+/−0.5° C. under 14/10 h light/dark cycles with a light intensity of 8000 Lx. Cells were analyzed after 5 to 7 days of cultivation.

For high-density cultures, cells could be cultivated in closed systems like, e.g., vertical or horizontal tube photobioreactors, stirred tank photobioreactors or flat panel photobioreactors as described by Chen et al. (Bioresour. Technol. 2011, 102: 71-81) and Johnson et al. (Biotechnol. Prog. 2018, 34: 811-827).

Example 30. Production of an Oligosaccharide Mixture Comprising GlcNAc-b1,3-Gal-b1,4-GlcNAc, beta-Gal-(1,4)-beta-GlcNAc-(1,3)-[beta-GlcNAc-(1,6)]-beta-Gal-(1,4)-GlcNAc and poly-LacNAc Structures in Mutant *C. reinhardtii* Cells

*C. reinhardtii* cells are engineered as described in Example 29, comprising genomic knock-ins of constitutive transcriptional units comprising the *Arabidopsis thaliana* genes encoding the galactokinase (KIN, UniProt ID Q9SEE5) and the UDP-sugar pyrophosphorylase (USP) (UniProt ID Q9C5I1), the mutant glmS*54 from *E. coli* (differing from the wild-type glmS (UniProt ID P17169) by an A39T, an R250C and an G472S mutation, the phosphatase yqaB from *E. coli* (UniProt ID NP_417175.1), galE from *E. coli* (UniProt ID P09147), LgtA from *N. meningitidis* (UniProt ID Q9JXQ6), LgtB from *N. meningitidis* (UniProt ID Q51116) and the human N-acetyllactosaminide beta-1,6-N-acetylglucosaminyltransferase GCNT2 (UniProt ID Q8NOV5). The novel strains are evaluated for production of an oligosaccharide mixture comprising GlcNAc-b1,3-Gal-b1,4-GlcNAc, beta-Gal-(1,4)-beta-GlcNAc-(1,3)-[beta-GlcNAc-(1,6)]-beta-Gal-(1,4)-GlcNAc and poly-LacNAc structures in a cultivation experiment on TAP-agar plates comprising galactose and GlcNAc as precursors according to the culture conditions provided in Example 29.

Example 31. Materials and Methods Animal Cells Isolation of Mesenchymal Stem Cells from Adipose Tissue of Different Mammals Fresh adipose tissue is obtained from slaughterhouses (e.g., cattle, pigs, sheep, chicken, ducks, catfish, snake, frogs) or liposuction (e.g., in case of humans, after informed consent) and kept in phosphate buffer saline supplemented with antibiotics. Enzymatic digestion of the adipose tissue is performed followed by centrifugation to isolate mesenchymal stem cells. The isolated mesenchymal stem cells are transferred to cell culture flasks and grown under standard growth conditions, e.g., 37° C., 5% CO2. The initial culture medium includes DMEM-F12, RPMI, and Alpha-MEM medium (supplemented with 15% fetal bovine serum), and 1% antibiotics. The culture medium is subsequently replaced with 10% FBS (fetal bovine serum)-supplemented media after the first passage. For example, Ahmad and Shakoori (2013, Stem Cell Regen. Med. 9(2): 29-36), which is incorporated herein by reference in its entirety for all purposes, describes certain variation(s) of the method(s) described herein in this example.

Isolation of Mesenchymal Stem Cells from Milk

This example illustrates isolation of mesenchymal stem cells from milk collected under aseptic conditions from human or any other mammal(s) such as described herein. An equal volume of phosphate buffer saline is added to diluted milk, followed by centrifugation for 20 min. The cell pellet is washed thrice with phosphate buffer saline and cells are seeded in cell culture flasks in DMEM-F12, RPMI, and Alpha-MEM medium supplemented with 10% fetal bovine serum and 1% antibiotics under standard culture conditions. For example, Hassiotou et al. (2012, Stem Cells. 30(10): 2164-2174), which is incorporated herein by reference in its entirety for all purposes, describes certain variation(s) of the method(s) described herein in this example.

Differentiation of Stem Cells Using 2D and 3D Culture Systems

The isolated mesenchymal cells can be differentiated into mammary-like epithelial and luminal cells in 2D and 3D culture systems. See, for example, Huynh et al. 1991. Exp. Cell Res. 197(2): 191-199; Gibson et al. 1991, In Vitro Cell Dev. Biol. Anim. 27(7): 585-594; Blatchford et al. 1999; Animal Cell Technology: Basic & Applied Aspects, Springer, Dordrecht. 141-145; Williams et al. 2009, Breast Cancer Res. 11(3): 26-43; and Arevalo et al. 2015, Am. J. Physiol. Cell Physiol. 310(5): C348-C356; each of which is incorporated herein by reference in their entireties for all purposes.

For 2D culture, the isolated cells were initially seeded in culture plates in growth media supplemented with 10 ng/ml epithelial growth factor and 5 pg/ml insulin. At confluence, cells were fed with growth medium supplemented with 2% fetal bovine serum, 1% penicillin-streptomycin (100 U/ml penicillin, 100 ug/ml streptomycin), and 5 pg/ml insulin for 48 h. To induce differentiation, the cells were fed with complete growth medium containing 5 pg/ml insulin, 1 pg/ml hydrocortisone, 0.65 ng/ml triiodothyronine, 100 nM dexamethasone, and 1 pg/ml prolactin. After 24 h, serum is removed from the complete induction medium.

For 3D culture, the isolated cells were trypsinized and cultured in Matrigel, hyaluronic acid, or ultra-low attachment surface culture plates for six days and induced to differentiate and lactate by adding growth media supplemented with 10 ng/ml epithelial growth factor and 5 pg/ml insulin. At confluence, cells were fed with growth medium supplemented with 2% fetal bovine serum, 1% penicillin-streptomycin (100 U/ml penicillin, 100 ug/ml streptomycin), and 5 pg/ml insulin for 48 h. To induce differentiation, the cells were fed with complete growth medium containing 5 pg/ml insulin, 1 pg/ml hydrocortisone, 0.65 ng/ml triiodothyronine, 100 nM dexamethasone, and 1 pg/ml prolactin. After 24 h, serum is removed from the complete induction medium.

Method of Making Mammary-Like Cells

Mammalian cells are brought to induced pluripotency by reprogramming with viral vectors encoding for Oct.4, Sox2, Klf4, and c-Myc. The resultant reprogrammed cells are then cultured in Mammocult media (available from Stem Cell Technologies), or mammary cell enrichment media (DMEM, 3% FBS, estrogen, progesterone, heparin, hydrocortisone, insulin, EGF) to make them mammary-like, from which expression of select milk components can be induced. Alternatively, epigenetic remodeling are performed using remodeling systems such as CRISPR/Cas9, to activate select genes of interest, such as casein, a-lactalbumin to be constitutively on, to allow for the expression of their respective proteins, and/or to down-regulate and/or knock-out select endogenous genes as described, e.g., in WO21067641, which is incorporated herein by reference in its entirety for all purposes.

Cultivation

Completed growth media includes high glucose DMEM/F12, 10% FBS, 1% NEAA, 1% pen/strep, 1% ITS-X, 1% F-Glu, 10 ng/ml EGF, and 5 pg/ml hydrocortisone. Completed lactation media includes high glucose DMEM/F12, 1% NEAA, 1% pen/strep, 1% ITS-X, 1% F-Glu, 10 ng/ml EGF, 5 pg/ml hydrocortisone, and 1 pg/ml prolactin (5 ug/ml in Hyunh 1991). Cells are seeded at a density of 20,000 cells/cm2 onto collagen coated flasks in completed growth media and left to adhere and expand for 48 hours in completed growth media, after which the media is switched out for completed lactation media. Upon exposure to the lactation media, the cells start to differentiate and stop growing. Within about a week, the cells start secreting lactation product(s) such as milk lipids, lactose, casein and whey into the media. A desired concentration of the lactation media can be achieved by concentration or dilution by ultrafiltration. A desired salt balance of the lactation media can be achieved by dialysis, for example, to remove unwanted metabolic products from the media. Hormones and other growth factors used can be selectively extracted by resin purification, for example the use of nickel resins to remove His-tagged growth factors, to further reduce the levels of contaminants in the lactated product.

Example 32. Evaluation of Production of an Oligosaccharide Mixture Comprising LNB, LN3, LNT, GalNAc-b1,3-lactose, Gal-b1,3-GalNAc-b1,3-lactose, GalNAc-b1,3-LNB and Gal-b1,3-GalNAc-b1, 3-LNB in a Non-Mammary Adult Stem Cell Isolated mesenchymal cells and re-programmed into mammary-like cells as described in Example 31 are modified via CRISPR-CAS to over-express the beta-1,4-galactosyltransferase 1 B4GalT1 from *Homo sapiens* (UniProt ID P15291), the phosphatase ScDOG1 from *S. cerevisiae* (UniProt ID P38774), GNA1 from *S. cerevisiae* (UniProt ID P43577) and WbgO from *E. coli* O55:H7 (UniProt ID D3QY14), the 4-epimerase (WbpP) of *P. aeruginosa* (UniProt ID Q8KN66), the galactoside beta-1,3-N-acetylglucosaminyltransferase (LgtA) from *N. meningitidis* (UniProt ID Q9JXQ6) and the β1,3-N-acetylgalactosaminyltransferase (LgtD) from *H. influenzae* (UniProt ID A0A2X4DBP3). All genes introduced in the cells are codon-optimized to the host. Cells are seeded at a density of 20,000 cells/cm2 onto collagen coated flasks in completed growth media and left to adhere and expand for 48 hours in completed growth media, after which the media is switched out for completed lactation media for about 7 days. After cultivation as described in Example 31, cells are subjected to UPLC and evaluated for production of an oligosaccharide mixture comprising LNB, LN3, LNT, GalNAc-b1,3-lactose, Gal-b1,3-GalNAc-b1,3-lacto se, GalNAc-b1,3-Gal-b1,3-GlcNAc-b1,3-Gal-b1,4-Glc, GalNAc-b1,3-LNB and Gal-b1,3-GalNAc-b1,3-LNB.

The invention claimed is:

1. A metabolically engineered cell that produces a mixture of at least four different neutral non-fucosylated mammalian milk oligosaccharides, wherein said cell:
   is metabolically engineered for production of said mixture,
   expresses at least two different glycosyltransferases involved in producing the mixture of at least four different neutral non-fucosylated mammalian milk oligosaccharides, wherein each of said at least two glycosyltransferases is selected from the group consisting of a galactosyltransferase, an N-acetylglucosaminyltransferase, and an N-acetylgalactosaminyltransferase, and
   is capable of synthesizing at least one nucleotide-sugar, wherein each nucleotide-sugar is a donor for at least one glycosyltransferase.

2. The cell according to claim 1, wherein said mixture comprises at least three different neutral non-fucosylated oligosaccharides differing in degree of polymerization.

3. The cell according to claim 1, wherein said cell produces five or more different neutral non-fucosylated oligosaccharides.

4. The cell according to claim 1, wherein said cell expresses at least three glycosyltransferases.

5. The cell according to claim 1, wherein at least one of said glycosyltransferases is an endogenous protein having a modified expression or activity in comparison to an unmodified cell.

6. The cell according to claim 1, wherein the cell synthesizes at least one nucleotide-sugar selected from the group consisting of UDP-N-acetylglucosamine (UDP-GlcNAc), UDP-galactose (UDP-Gal), UDP-N-acetylgalactosamine (UDP-GalNAc), UDP-N-acetylmannosamine (UDP-ManNAc), GDP-mannose (GDP-Man), UDP-glucose (UDP-Glc), GDP-rhamnose, UDP-xylose, UDP-2-acetamido-2,6-dideoxy--L-arabino-4-hexulose, UDP-2-acetamido-2,6-dideoxy--L-lyxo-4-hexulose, UDP-N-acetyl-L-rhamnosamine (UDP-L-RhaNAc or UDP-2-acetamido-2,6-dideoxy-L-mannose), dTDP-N-acetylfucosamine, UDP-N-acetylfucosamine (UDP-L-FucNAc or UDP-2-acetamido-2, 6-dideoxy-L-galactose), UDP-N-acetyl-L-pneumosamine (UDP-L-PneNAC or UDP-2-acetamido-2,6-dideoxy-L-talose), UDP-N-acetylmuramic acid, UDP-N-acetyl-L-quinovosamine (UDP-L-QuiNAc or UDP-2-acetamido-2,6-dideoxy-L-glucose), and GDP-L-quinovose.

7. The cell according to claim 1, wherein said cell is able to synthesize at least two nucleotide-sugars.

8. The cell according to claim 1, wherein said cell uses at least one precursor for producing any one or more of said at least four different neutral non-fucosylated mammalian milk oligosaccharides.

9. The cell according to claim 1, wherein said cell produces at least one precursor for the production of any one of said at least four different neutral non-fucosylated mammalian milk oligosaccharides.

10. The cell according to claim 1, wherein said cell produces said at least four different neutral non-fucosylated mammalian milk oligosaccharides intracellularly and wherein at least a fraction of said produced at least four different neutral non-fucosylated mammalian milk oligosaccharides is excreted outside said cell via active transport.

11. The cell according to claim 1, wherein said cell is further genetically modified for
i) modified expression of an endogenous membrane protein,
ii) modified activity of an endogenous membrane protein,
iii) expression of a homologous membrane protein, or
iv) expression of a heterologous membrane protein,
wherein said membrane protein is involved in
secretion of at least one of said at least four different neutral non-fucosylated mammalian milk oligosaccharides from said mixture outside said cell, or
uptake of a precursor or acceptor for synthesis of any one of the at least four different neutral non-fucosylated mammalian milk oligosaccharides of the mixture.

12. The cell according to claim 11, wherein said membrane protein is selected from the group consisting of porters, P-P-bond-hydrolysis-driven transporters, (β-barrel porins, auxiliary transport proteins, putative transport proteins and phosphotransfer-driven group translocators.

13. The cell according to claim 11, wherein said membrane protein improves production of any one of said at least four different neutral non-fucosylated mammalian milk oligosaccharides in comparison to a non-modified cell.

14. A method of producing a mixture of at least four different neutral non-fucosylated mammalian milk oligosaccharides by a cell, the method comprising the steps of:
i) providing the cell of claim 1, and
ii) cultivating said cell under conditions permissive to express said glycosyltransferases and
to synthesize said one or more nucleotide-sugar(s).

15. The method according to claim 14, wherein said cell is metabolically engineered for production of the mixture, expresses at least two glycosyltransferases, and
is able to synthesize two or more nucleotide-sugars, wherein the two or more nucleotide-sugars are donor(s) for the glycosyltransferases.

16. The method according to claim 14, wherein said cell produces five or more different neutral non-fucosylated mammalian milk oligosaccharides.

17. The method according to claim 14, wherein said cell expresses at least three glycosyltransferases.

18. The method according to claim 14, further comprising purification of any one of said at least four different neutral non-fucosylated mammalian milk oligosaccharides from said cell.

19. The method according to claim 18, wherein said purification comprises at least one of the following steps: use of activated charcoal or carbon, use of charcoal, nanofiltration, ultrafiltration, electrophoresis, enzymatic treatment or ion exchange, use of alcohols, use of aqueous alcohol mixtures, crystallization, evaporation, precipitation, drying, drying, lyophilization, spray freeze drying, freeze spray drying, band drying, belt drying, vacuum band drying, vacuum belt drying, drum drying, roller drying, vacuum drum drying, or vacuum roller drying.

20. The cell according to claim 1, wherein said cell is a bacterium, yeast, a plant cell, or an animal cell.

21. The cell of claim 4, wherein the at least three glycosyltransferases are involved in producing the mixture.

22. The cell of claim 1, wherein any one of the one or more nucleotide-sugar(s) is selected from the group consisting of UDP-N-acetylglucosamine (UDP-GlcNAc), UDP-galactose (UDP-Gal), UDP-N-acetylgalactosamine (UDP-GalNAc), UDP-N-acetylmannosamine (UDP-ManNAc), GDP-mannose (GDP-Man), UDP-glucose (UDP-Glc), GDP-rhamnose, and UDP-xylose.

23. The method according to claim 14, further comprising:
separating at least one of neutral non-fucosylated mammalian milk oligosaccharides from the cultivation.

24. The method according to claim 23, wherein separating comprises at least one of the following steps: clarification, ultrafiltration, nanofiltration, two-phase partitioning, reverse osmosis, microfiltration, activated charcoal or carbon treatment, treatment with non-ionic surfactants, enzymatic digestion, tangential flow high-performance filtration, tangential flow ultrafiltration, affinity chromatography, ion exchange chromatography, hydrophobic interaction chromatography, gel filtration, ligand exchange chromatography.

25. The cell of claim 1, wherein at least one of the glycosyltransferases is a heterologous protein.

26. The cell of claim 11, wherein the membrane protein enhances efflux of any one of the at least four different neutral non-fucosylated mammalian milk oligosaccharides in comparison to a non-modified cell.

27. The method according to claim 17, wherein the at least three glycosyltransferases are involved in producing the mixture.

* * * * *

UNITED STATES PATENT AND TRADEMARK OFFICE
CERTIFICATE OF CORRECTION

PATENT NO. : 12,077,788 B2
APPLICATION NO. : 18/040629
DATED : September 3, 2024
INVENTOR(S) : Sofie Aesaert et al.

It is certified that error appears in the above-identified patent and that said Letters Patent is hereby corrected as shown below:

In the Specification

| | | |
|---|---|---|
| Column 22, | Line 55, | change ""PDX," "poxB"" to --"POX," "poxB"-- |
| Column 25, | Line 20, | change "transporters (β-Barrel" to --transporters β-Barrel-- |
| Column 27, | Line 1, | change "transmembrane a-helical spanners" to --transmembrane α-helical spanners-- |
| Column 46, | Line 6, | change "the Enzyme 11 Man complex" to --the Enzyme II Man complex-- |
| Column 53, | Lines 15-16, | change "galactoside 0-acetyltransferase," to --galacteside O-acetyltransferase,-- |
| Column 54, | Line 24, | change "*K marxianus, K thermotolerans*)," to --*K. Marxianus, K. Thermotolerans*),-- |
| Column 63, | Line 51, | change "vitamins A, Bb, Bit, C and D)," to --vitamins A, B6, B12, C and D),-- |
| Column 68, | Line 1, | change "N-acetylgalactosaminyltransferase s," to --N-acetylgalactosaminyltransferases,-- |
| Column 70, | Line 49, | change "galactoside 0-acetyltransferase" to --galactoside O-acetyltransferase-- |
| Column 74, | Line 40, | change "galactoside 0-acetyltransferase" to --galactoside O-acetyltransferase-- |
| Column 82, | Line 25, | change "wcaE, wcal, wcaJ," to --wcaE, wcaI, wcaJ,-- |
| Column 87, | Line 45, | change "01,3-N-Acetyl-galactosaminyltransferase" to --β1,3-N-Acetyl-galactosaminyltransferase-- |
| Column 87, | Line 46, | change "01,3-galactosetransferase" to --β1,3-N-galactosetransferase-- |
| Column 87, | Line 52-53, | change "Gal-b 1,3-GalNAc-b 1,3-l acto se, GalNAc-b 1,3-Gal-a1,4-Gal-b 1, 4-Glc (gl ob o-N-tetrao se)" to --Gal-b1,3-GalNAc-b1,3-lactose, GalNAc-b1,3-Gal-a1,4-Gal-b1,4-Glc (globo-N-tetraose)-- |

Signed and Sealed this
Twenty-sixth Day of November, 2024

*Katherine Kelly Vidal*

Katherine Kelly Vidal
*Director of the United States Patent and Trademark Office*

|           | Column 88,  | Lines 26-27, | change "GalNAc-b1,3-lacto se" to --GalNAc-b1,3-lactose-- |
|           | Column 90,  | Lines 4-5,   | change "1GalNAc)-poly-LNnT" to --(GalNAc)-poly-LNnt-- |
|           | Column 94,  | Lines 63-64, | change "1GalNAc)-poly-LNnT" to --(GalNAc)-poly-LNnt-- |
|           | Column 98,  | Line 9,      | change "H3B03," to --H3BO3,-- |
|           | Column 99,  | Line 61,     | change "Q8NOV5)." to --Q8N0V5).-- |
|           | Column 103, | Lines 23-34, | change "(β-barrel porins," to --β-barrels porins,-- |

In the Claims

| Claim 12, | Column 193, | Lines 23-24, | change "(β-barrel porins," to --β-barrel porins,-- |